US012419976B2

(12) United States Patent
Van Leeuwen et al.

(10) Patent No.: US 12,419,976 B2
(45) Date of Patent: Sep. 23, 2025

(54) HYBRID TRACERS FOR TARGETED CANCER IMAGING AND TREATMENT

(71) Applicants: ACADEMISCH ZIEKENHUIS LEIDEN (H.O.D.N. LUMC), ZA Leiden (NL); TECHNISCHE UNIVERSITÄT MÜNCHEN, Munich (DE); SCINTOMICS GMBH, Fürstenfeldbruck (DE)

(72) Inventors: Fijs W. B. Van Leeuwen, ZA Leiden (NL); Hans-Jurgen Wester, Munich (DE); Tessa Buckle, ZA Leiden (NL); Danny Van Willigen, ZA Leiden (NL); Margret Schottelius, Munich (DE); Saskia Kropf, Fürstenfeldbruck (DE)

(73) Assignees: ACADEMISCH ZIEKENHUIS LEIDEN (H.O.D.N. LUMC) GMBH (NL); SCINTOMICS GMBH (DE); TECHNISCHE UNIVERSITÄT MÜNCHEN (DE)

( * ) Notice: Subject to any disclaimer, the term of this patent is extended or adjusted under 35 U.S.C. 154(b) by 772 days.

(21) Appl. No.: 17/283,761

(22) PCT Filed: Oct. 11, 2019

(86) PCT No.: PCT/EP2019/077600
§ 371 (c)(1),
(2) Date: Apr. 8, 2021

(87) PCT Pub. No.: WO2020/074705
PCT Pub. Date: Apr. 16, 2020

(65) Prior Publication Data
US 2021/0338841 A1 Nov. 4, 2021

(30) Foreign Application Priority Data
Oct. 11, 2018 (EP) .................................... 18199963

(51) Int. Cl.
A61K 49/10 (2006.01)
A61K 49/00 (2006.01)
(Continued)

(52) U.S. Cl.
CPC ........ *A61K 49/106* (2013.01); *A61K 49/0002* (2013.01); *A61K 51/0482* (2013.01); *C07D 403/06* (2013.01); *C07D 403/14* (2013.01)

(58) Field of Classification Search
None
See application file for complete search history.

(56) References Cited

U.S. PATENT DOCUMENTS 7,408,079 B2  8/2008 Pomper et al.
9,884,132 B2  2/2018 Pomper et al.
(Continued)

FOREIGN PATENT DOCUMENTS

CN  108752319 A  11/2018
WO  2010108125 A2  9/2010
(Continued)

OTHER PUBLICATIONS

Chen et al.,Synthesis and Biological Evaluation of Low Molecular Weight Fluorescent Imaging Agents for the Prostate-Specific Membrane Antigen, Nov. 19, 2012, Bioconjugate Chem, 23:2377-2385 (Year: 2012).*
(Continued)

*Primary Examiner* — Michael G. Hartley
*Assistant Examiner* — Kaila A Craig
(74) *Attorney, Agent, or Firm* — Natalie Salem; Chinh Pham; Greenberg Traurig, LLP

(57) ABSTRACT

This invention relates to compounds of formula I or Ia: (I) (Ia). Y is EuK, —EuAF, —EuPG, -L-EuE; Z is a chelating moiety; and the other substituents are as defined herein. Also provided are formulations comprising such a compound, as well as methods of imaging or methods for the treatment of cancer comprising use of such a compound or formulation.
(Continued)

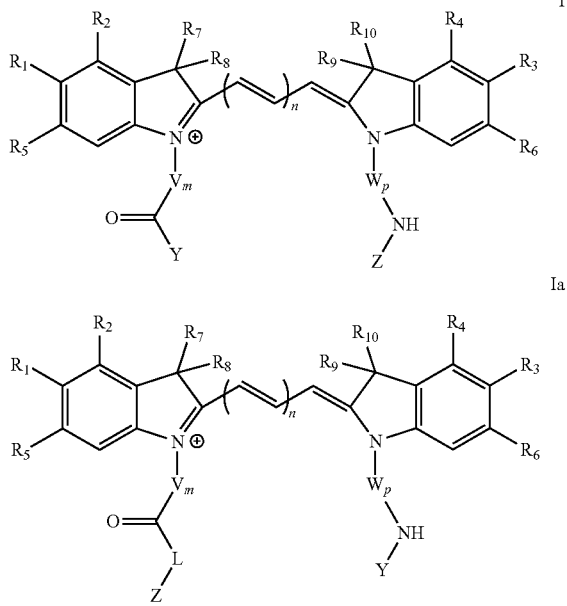

17 Claims, 7 Drawing Sheets

(51) Int. Cl.
 A61K 51/04 (2006.01)
 C07D 403/06 (2006.01)
 C07D 403/14 (2006.01)

(56) References Cited

U.S. PATENT DOCUMENTS

| | | | |
|---|---|---|---|
| 10,093,741 B1 * | 10/2018 | Burak | A61P 35/00 |
| 2012/0009121 A1 | 1/2012 | Pomper et al. | |
| 2013/0230466 A1 * | 9/2013 | Hermanson | C09B 23/06 435/7.1 |
| 2014/0178300 A1 | 6/2014 | Pomper et al. | |
| 2015/0110715 A1 | 4/2015 | Eder et al. | |
| 2015/0110814 A1 | 4/2015 | Olson et al. | |
| 2015/0147339 A1 | 5/2015 | Olson et al. | |
| 2017/0189568 A1 | 7/2017 | Kung et al. | |
| 2017/0333576 A1 | 11/2017 | Pomper et al. | |
| 2017/0369454 A1 | 12/2017 | Babich et al. | |
| 2018/0051039 A1 | 2/2018 | Pomper et al. | |

FOREIGN PATENT DOCUMENTS

| | | |
|---|---|---|
| WO | 2013082338 A1 | 6/2013 |
| WO | 2015171792 A1 | 11/2015 |
| WO | 2017059060 A1 | 4/2017 |
| WO | 2017070482 A2 | 4/2017 |
| WO | 2017082620 A1 | 5/2017 |
| WO | 2017220488 A1 | 12/2017 |

OTHER PUBLICATIONS

Xiao et al., Heptamethine cyanine based 64Cu-PET probe PC-1001 for cancer imaging: Synthesis and in vivo evaluation, Jan. 2, 2013, Nuclear Medicine and Biology, 40:351-360 (Year: 2013).*
Miki et al., pH-Responsive near-infrared fluorescent cyanine dyes for molecular imaging based on pH sensing, Jun. 19, 2017, Chemical Communications, 53:7792 (Year: 2017).*
Kommidi et al., 18F Positron Emitting/Trimethine Cyanine-Fluorescent Contrast forImage-Guided Prostate Cancer Management, Apr. 20, 2018, Journal of Medicinal Chemistry, 61:4256-4262 (Year: 2018).*
Stammes et al., Pre-clinical Evaluation of a Cyanine-Based SPECT Probe for Multimodal Tumor Necrosis Imaging, Jun. 8, 2016, Molecular Imaging and Biology, 18:905-915 (Year: 2016).*
Spa (The influence of systematic structure alterations on the photophysical properties and conjugation characteristics of asymmetric cyanine 5 dyes, Feb. 3, 2018, Dyes and Pigments, 152:19-28) (Year: 2018).*
Fragomeni et al., "Imaging of Nonprostate Cancers Using PSMA-Targeted Radiotracers: Rationale, Current State of the Field, and a Call to Arms" Journal of Nuclear Medicine, vol. 59, No. 6, pp. 871-877, Jun. 2018.
International Preliminary Report on Patentability in International Application No. PCT/EP2019/077600 mailed Apr. 8, 2021.
Eleni Gourni et al: Metal-Based PSMA Radioligands11 , Molecules, vol. 22, No. 4, Mar. 24, 2017, p. 523 (34 pages).
Ying Chen et al: Synthesis and Biological Evaluation of Low Molecular Weight Fluorescent Imaging Agents for the Prostate-Specific Membrane Antigen11 , Bioconjugate Chemistry, vol. 23, No. 12, Dec. 19, 2012, pp. 2377-2385.
International Search Report and Written Opinion in International Application No. PCT/EP2019/077600 mailed Nov. 29, 2019.
Banerjee et al., "Effect of Chelators on the Pharmacokinetics of 99mTc-Labeled Imaging Agents for the Prostate-Specific Membrane Antigen (PSMA)," Journal of Medicinal Chemistry, 2013, vol. 56, pp. 6108-6121.
Banerjee et al., "Synthesis and Evaluation of Technetium-99m- and Rhenium-Labeled Inhibitors of the Prostate-Specific Membrane Antigen (PSMA)," Journal of Medicinal Chemistry, 2008, vol. 51, No. 15, pp. 4504-4517.
Baranski et al., "Improving the Imaging Contrast of 68Ga-PSMA-11 by Targeted Linker Design: Charged Spacer Moieties Enhance the Pharmacokinetic Properties," Bioconjugate Chemistry, Aug. 8, 2017, vol. 28, No. 9, pp. 2485-2492.
Baranski et al., "PSMA-11 Derived Dual-labeled PSMA-Inhibitors for Preoperative PET Imaging and Precise Fluorescence-Guided Surgery of Prostate Cancer," Journal of Nuclear Medicine, 2018, vol. 59, No. 4, pp. 639-645.
Eder et al., "68Ga-Complex Lipophilicity and the Targeting Property of a Urea-Based PSMA Inhibitor for PET Imaging," Bioconjugate Chemistry, 2012, vol. 23, pp. 688-697.
Giglio et al., "Synthesis of an Al18F radiofluorinated GLU-UREA-LYS(AHX)-HBED-CC PSMA ligand in an automated synthesis platform," EJNMMI Radiopharmacy and Chemistry, 2018, vol. 3, Article No. 4, pp. 1-12.
Liolios et al., "Novel Bispecific PSMA/GRPr Targeting Radioligands with Optimized Pharmacokinetics for Improved PET Imaging of Prostate Cancer," Bioconjugate Chemistry, 2016, vol. 27, pp. 737-751.
Lutje et al., "PSMA Ligands for Radionuclide Imaging and Therapy of Prostate Cancer: Clinical Status," Theranostics, 2015, vol. 5, Iss. 12, pp. 1388-1401.
Maresca et al., "Small molecule inhibitors of PSMA incorporating technetium-99m for imaging prostate cancer: Effects of chelate design on pharmacokinetics," Inorganica Chimica Acta, Jul. 2012, vol. 389, pp. 168-175.
Shallal et al., "Heterobivalent Agents Targeting PSMA and Integrin-αvβ3," Bioconjugate Chemistry, 2014, vol. 25, pp. 393-405.

* cited by examiner

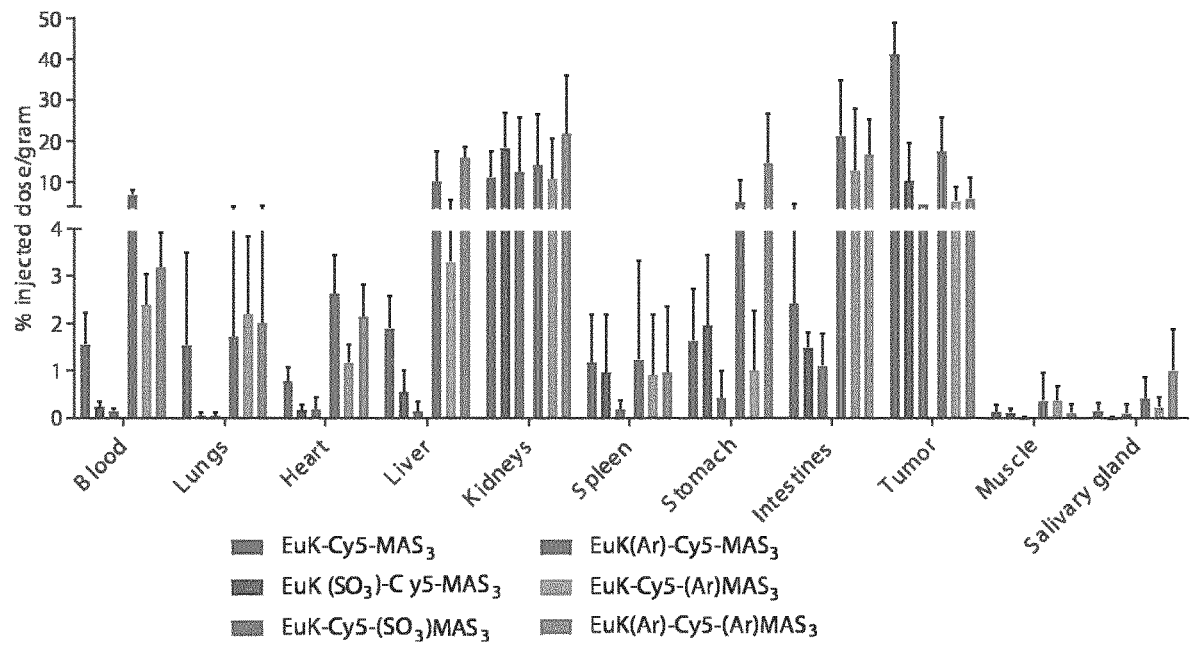
Figure 4 B)
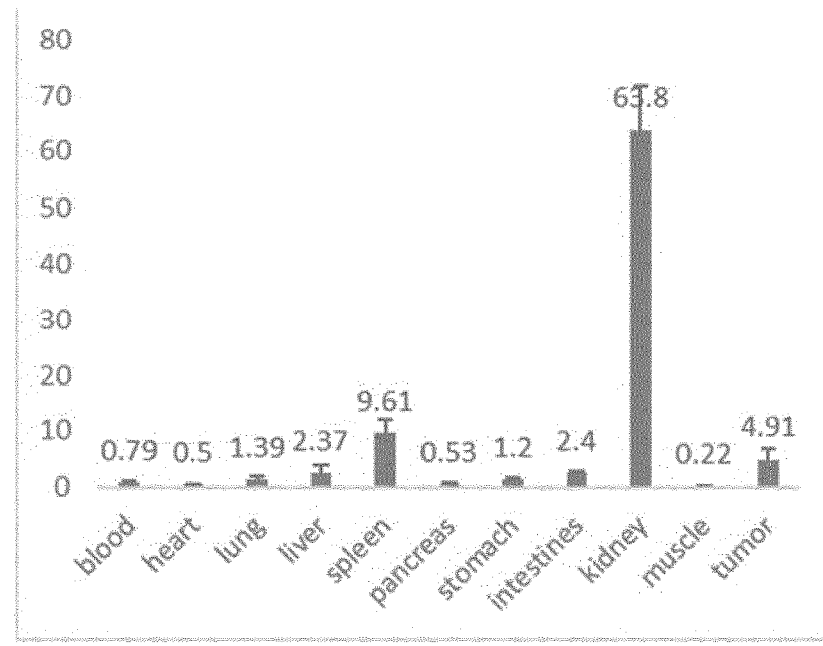
Figure 4 c) Biodistribution of MAS3(SO₃)-Cy5 -(SO₃)EuK, 1h p.i., SCID mice

HYBRID TRACERS FOR TARGETED CANCER IMAGING AND TREATMENT

CROSS REFERENCE TO RELATED APPLICATIONS

This application is a U.S. National Phase patent application of PCT International Application No. PCT/EP2019/077600, filed Oct. 11, 2019, which claims priority to and the benefit of European Application No. 18199963.2, filed on Oct. 11, 2018, the entire contents of each of which are hereby incorporated by reference in their entireties.

This invention relates to compounds that are useful as tracers, in particular as tracers that may be used in the targeting of cancer (e.g. prostate cancer). The tracers represent hybrid tracers comprising a probe, a dye moiety and a moiety that may include a radiolabel.

BACKGROUND

Interventional molecular imaging technologies are needed for the management of primary tumours and their metastases. Cancers such as prostate cancer have a relatively high prevalence and treatment of such cancers is technically difficult. Image guided resection of the primary tumour as well as lymphatic metastases is thought to enhance the surgical outcome.

One approach to providing image guided resection involves the provision of a molecule that can act as a labelled tracer. Prostate-specific membrane antigen (PSMA), a transmembrane protein expressed in prostatic tissue, represents a useful diagnostic and possible therapeutic target for prostate cancer. In addition, as reported by Fragomeni et al., *J. Nuc. Med., Jun.* 1, 2018, 59(6), 871-877, PSMA expression has been shown in the neovasculature of a wide array of nonprostate malignancies, raising the possibility of PSMA theranostic applications outside prostate cancer The glutamate-urea-lysine (EuK) vector is known to target prostate-specific membrane antigen (PSMA), allowing tracers that consist of suitably functionalized EuK vectors to be used to detect prostate cancer. Other EuX based vectors have been used in a similar manner. Exemplary molecules based on EuX vectors are disclosed in, for example, WO2010/108125 and WO 2013/082338. These molecules do, however, suffer from a number of disadvantages. For example, none of these molecules have been demonstrated to have high utility for hybrid imaging where a single tracer facilitates both general pre-operative detection and intraoperative fluorescence imaging.

Given the promise of a better oncological outcome following radical surgical resection of tumours there is thus a general need to develop further tracers for the purpose of surgical guidance. An object of the invention is therefore to provide compounds that are useful as tracers for the detection of cancer, e.g. prostate cancer and/or other cancers detectable with a PSMA probe. In particular, it is an object of the invention to provide hybrid compounds that allow non-invasive imaging and/or imaging during surgery by making combined used of fluorescent dyes and radiolabels. Another object of the invention is to provide compounds that have predictive and tunable pharmacokinetics which helps to usefully isolate cancer (e.g. prostate cancer and/or other cancers detectable with a PSMA probe) while preventing unwanted uptake in background organs.

BRIEF SUMMARY OF THE DISCLOSURE

The invention provides compounds that are useful as tracers. In particular, compounds of the invention combine a probe (e.g. a PSMA probe) with a fluorophore and moiety that may be radiolabeled, e.g. by chelating a radioactive nucleotide. These compounds, when they comprise a radiolabeled nucleotide, may be considered a hybrid tracer, as the probe portion is conjugated to two labels that can serve a complementary purpose: a fluorophore and a radiolabel.

In accordance with a first aspect the present invention provides a compound of formula I or formula Ia, or a pharmaceutically acceptable salt thereof:

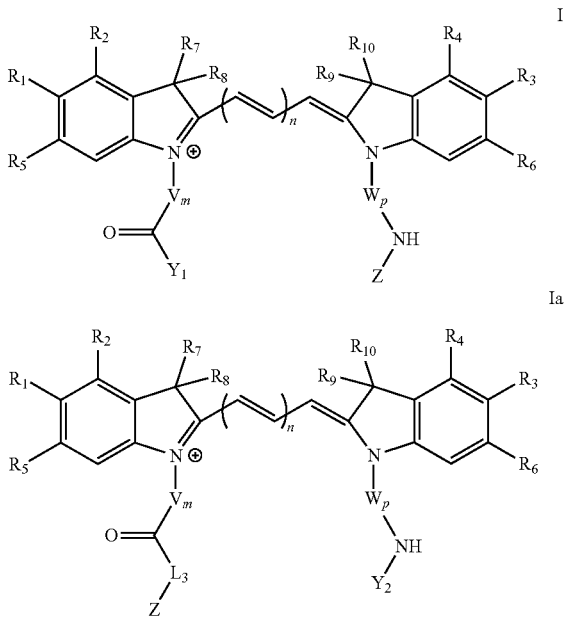

$R_1$ is selected from sulfonate, carboxyl, phosphonate, amine, azide, and H and $R_2$ is selected from sulfonate, carboxyl, phosphonate, amine, azide, and H; or $R_1$ and $R_2$ together form an aryl that is optionally substituted with one to four groups (e.g. one or two groups) each independently selected from sulfonate, carboxyl, phosphonate, amine and azide. $R_3$ is selected from sulfonate, carboxyl, phosphonate, amine, azide, and H and $R_4$ is selected from sulfonate, carboxyl, phosphonate, amine, azide, and H; or $R_3$ and $R_4$ together form an aryl that is optionally substituted with one to four groups (e.g. one or two groups) each independently selected from sulfonate, carboxyl, phosphonate, amine and azide. Each of $R_5$, $R_6$, $R_7$, $R_8$, $R_9$ and $R_{10}$ is independently selected from sulfonate, carboxyl, phosphonate, amine, azide, $CH_3$, $CH_2CH_3$ and H. V is —$CH_2$— or —$CH_2CH_2O$—. W is —$CH_2$— or —$CH_2CH_2O$—. $Y_1$ is —EuK, —EuFA, —EuPG, -$L_1$-EuK, -$L_1$-EuFA, -$L_1$-EuPG or -$L_3$-EuE. $Y_2$ is -$L_4$-EuK, -$L_4$-EuFA, -$L_4$-EuPG, —EuE, or -$L_2$-EuE. Z is a chelating moiety; for example Z may be -$MAS_3$, -$MAG_3$, -DOTA-GA, -DOTA, -DTPA, -$L_2$-$MAS_3$, -$L_2$-$MAG_3$, -$L_2$-DOTA-GA, -$L_2$-DOTA, -$L_2$-DTPA. $L_1$ is a linker of formula —NH—$R_{12}$—C(O)—, where $R_{12}$ is a bond, or a substituted or unsubstituted alkyl; for example $L_1$ may be a residue of lysine, a residue of ornithine, a residue of aspartic acid, a residue of glutamic acid, or —NH—($C_0$-$C_7$alkyl)-C(O)—. $L_2$ is a linker of formula —C(O)—$R_{13}$—NH—, where $R_{13}$ is a bond, or a substituted or unsubstituted alkyl; for example $L_2$ may be a bond, a residue of lysine, a residue of ornithine, a residue of aspartic acid, a residue of glutamic acid, or —NH—($C_0$-$C_7$alkyl)-C(O)—. $L_3$ is a linker of formula —NH—$R_{14}$—NH—, where $R_{14}$ is a substituted or unsubstituted alkyl; for example $L_3$ may be a residue of lysine, a residue of ornithine or —NH—($C_4$-$C_7$alkyl)-NH—. $L_4$ is a linker of formula —C(O)—$R_{15}$—C(O)—, where $R_{15}$ is a substituted or unsubstituted alkyl; for example $L_4$ may be a residue of aspartic acid, a residue of glutamic acid or —C(O)—($C_4$-$C_7$alkyl)-C(O)—. n is 2 or 3. m is 4, 5, 6, 7, 8, 9, 10, 11, 12, 13, 14, 15, 16, 17, 18, 19, 20, or 21. p is 3, 4, 5, 6, 7, 8, 9, 10, 11, 12, 13, 14, 15, 16, 17, 18, 19, 20, or 21.

Compounds of the first aspect may be useful as hybrid tracers, where "$Y_1$" or "$Y_2$" comprises a probe, "Z" may comprise a radiolabel (e.g. as chelated radionucleotide) and the portion therebetween comprises a fluorophore. The dye linker molecules have an amino-acid type structure, with formula I having "$Y_1$" attached to the C-terminus of the fluorophore and "Z" attached to the N-terminus end of the fluorophore; and formula Ia having "Z" attached to the C-terminus of the fluorophore and "$Y_2$" attached to the N-terminus end of the fluorophore. Using dye structures as linker molecules provides a number of advantages. For example, in such a molecular design the fluorophore is oriented in a predictable manner, which is highly advantageous where substituents $R^1$ to $R^{10}$ result in an asymmetric fluorophore. The latter feature allows the fluorophore to complement the EuX-vector and become part of the tracers pharmacophore. In particular the linker dye may be used to tune the interaction with the accessory hydrophobic pocket within PSMA.

A second aspect of the invention provides a compound of formula II or formula IIa, or a pharmaceutically acceptable salt thereof:

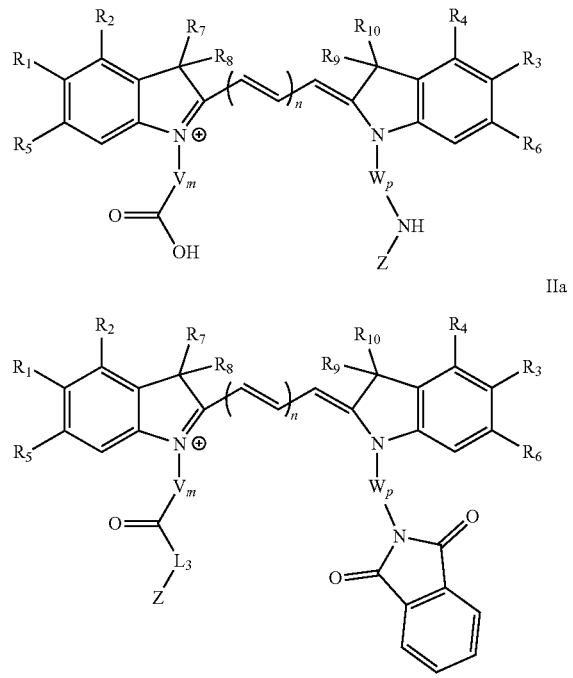

wherein $R_1$, $R_2$, $R_3$, $R_4$, $R_5$, $R_6$, $R_7$, $R_8$, $R_9$, $R_{10}$, V, W, Z, $L_3$, m, n and p are as defined for the first aspect. Compounds of the second aspect represent synthetic intermediates of compounds of the first aspect.

A third aspect of the invention provides a compound of formula III or formula IIIa, or a pharmaceutically acceptable salt thereof:

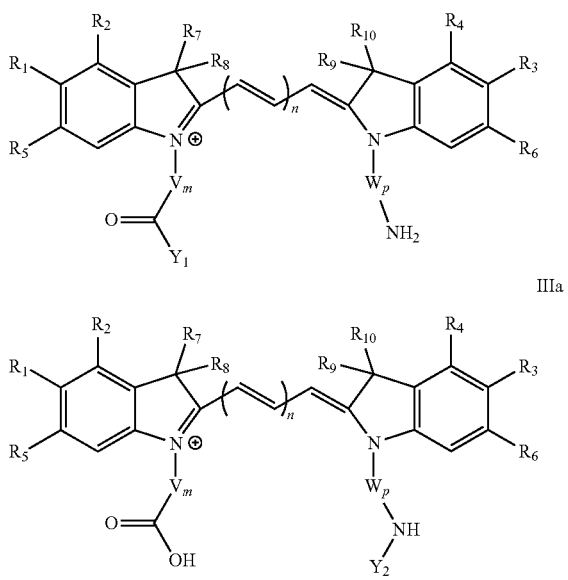

wherein $R_1$, $R_2$, $R_3$, $R_4$, $R_5$, $R_6$, $R_7$, $R_8$, $R_9$, $R_{10}$, V, W, $Y_1$, $Y_2$, m, n and p are as defined for the first aspect. Compounds of the second aspect represent synthetic intermediates of compounds of the first aspect.

A fourth aspect provides a formulation comprising a compound of the invention and optionally a pharmaceutically acceptable carrier. In an embodiment, the compound of the invention is a compound of the first aspect.

A fifth aspect provides a method for imaging a tumour, comprising administering to a subject a compound of the first aspect or formulation of the second aspect, and after a predetermined time imaging the tumour.

A sixth aspect provides a method for the treatment of cancer, comprising administering a compound of the first aspect or a formulation of the second aspect. In an embodiment, the compound comprises a chelated radiolabel.

A seventh aspect provides a use in imaging of a compound of the first aspect, or a formulation of the second aspect.

An eighth aspect provides a compound of the first aspect, or a formulation of the second aspect, for use as a medicament. In an embodiment, the compound comprises a chelated radiolabel.

A ninth aspect provides a compound of the first aspect, or a formulation of the second aspect, for use in the treatment of cancer. In an embodiment, the compound comprises a chelated radiolabel.

The invention will now be described further by reference to the following examples and figures. These are not intended to be limiting but merely exemplary of the invention.

BRIEF DESCRIPTION OF THE DRAWINGS

Embodiments of the invention are further described hereinafter with reference to the accompanying drawings, in which.

DETAILED DESCRIPTION

Figure 1:
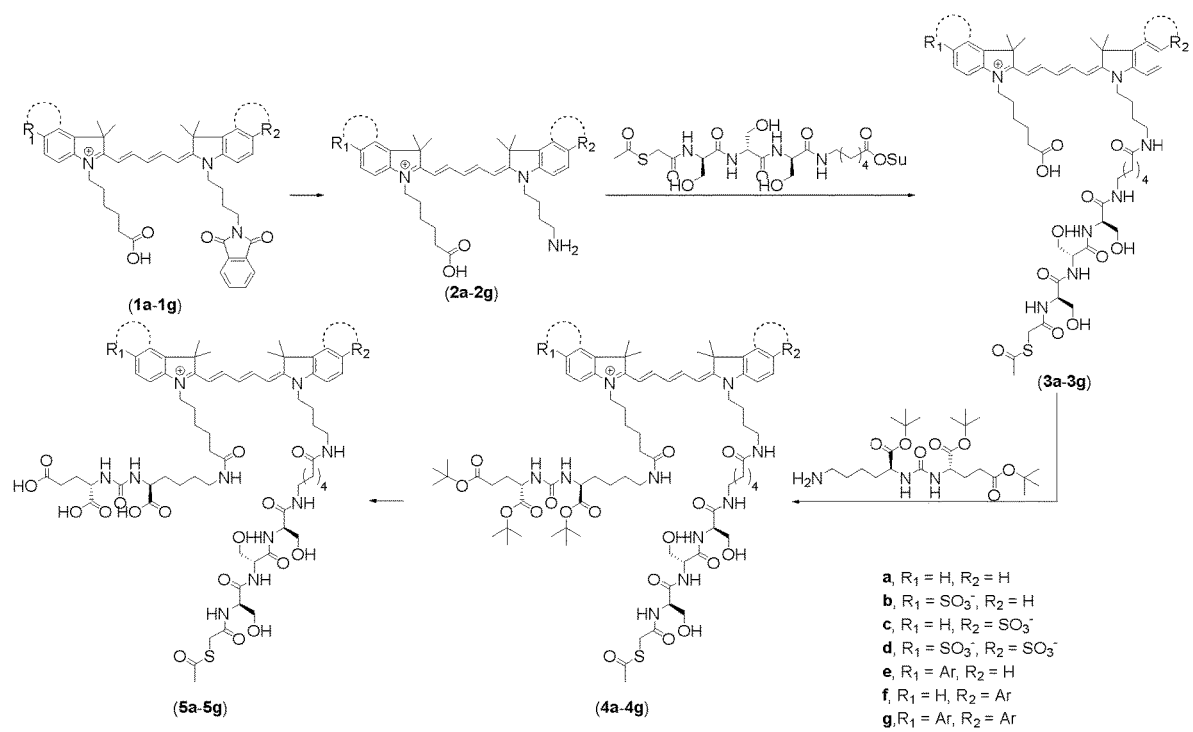
FIG. 1 illustrates a general reaction scheme 1 for synthesis of compounds of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

All publications, patent applications, patents, and other references mentioned herein are incorporated by reference in their entirety. In case of conflict, the present specification, including definitions, will control.

Definitions

The following explanations of terms and methods are provided to better describe the present disclosure and to guide those of ordinary skill in the art in the practice of the present disclosure.

The invention concerns amongst other things imaging. The term "imaging" includes providing a visual representation of a sample by detecting radiation. The radiation may be a product of radioactive decay of a radiolabel. The radiation may be a product of fluorescence. The visual representation may be provided by electronic processing of the detected radiation, for example by performing positron emission spectroscopy (PET), single photon emission computed tomography (SPECT), scintigraphy, (optionally intraoperative) gamma-tracing/imaging, (optionally intraoperative) beta-tracing. The visual representation may be provided by visual detection, for example by observing samples that fluoresce at visible wavelengths (e.g. from about 390 to 700 nm) on exposure to higher frequency electromagnetic radiation. The visual representation may be provided by fluorescence spectroscopy.

The invention concerns amongst other things the treatment of a disease. The term "treatment", and the therapies encompassed by this invention, include the following and combinations thereof: (1) hindering, e.g. delaying initiation and/or progression of, an event, state, disorder or condition, for example arresting, reducing or delaying the development of the event, state, disorder or condition, or a relapse thereof in case of maintenance treatment or secondary prophylaxis, or of at least one clinical or subclinical symptom thereof; (2) preventing or delaying the appearance of clinical symptoms of an event, state, disorder or condition developing in an animal (e.g. human) that may be afflicted with or predisposed to the state, disorder or condition but does not yet experience or display clinical or subclinical symptoms of the state, disorder or condition; and/or (3) relieving and/or curing an event, state, disorder or condition (e.g., causing regression of the event, state, disorder or condition or at least one of its clinical or subclinical symptoms, curing a patient or putting a patient into remission). The benefit to a patient to be treated may be either statistically significant or at least perceptible to the patient or to the physician. It will be understood that a medicament will not necessarily produce a clinical effect in each patient to whom it is administered; thus, in any individual patient or even in a particular patient population, a treatment may fail or be successful only in part, and the meanings of the terms "treatment", "prophylaxis" and "inhibitor" and of cognate terms are to be understood accordingly. The compositions and methods described herein are of use for therapy and/or prophylaxis of the mentioned conditions.

The term "prophylaxis" includes reference to treatment therapies for the purpose of preserving health or inhibiting or delaying the initiation and/or progression of an event, state, disorder or condition, for example for the purpose of reducing the chance of an event, state, disorder or condition occurring. The outcome of the prophylaxis may be, for example, preservation of health or delaying the initiation and/or progression of an event, state, disorder or condition. It will be recalled that, in any individual patient or even in a particular patient population, a treatment may fail, and this paragraph is to be understood accordingly.

The term "probe" or "targeting moiety" includes reference to a moiety or vector that targets PSMA via an affinity type interaction. Exemplary probes include moieties of formula EuX, namely glutamate linked to another amino acid or similar via a bridging urea, for example EuK, EuFA, EuPG, or EuE.

The term "tracer" includes reference to a molecule that comprises a targeting moiety and an imaging label. A tracer may comprise two imaging labels, e.g. as a hybrid tracer with two different types of imaging label. For example, in a hybrid tracer, a probe portion may be conjugated to two labels that can serve a complementary purpose: a fluorophore label and a radiolabel.

The term "inhibit" (and "inhibiting") includes reference to delaying, stopping, reducing the incidence of, reducing the risk of and/or reducing the severity of an event, state, disorder or condition. Inhibiting an event, state, disorder or condition may therefore include delaying or stopping initiation and/or progression of such, and reducing the risk of such occurring. A probe EuX may be considered an inhibitor of PSMA.

The term "chelating moiety" includes reference to a residue of a chelating agent such as bis(carboxymethyl)-1, 4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4, 8,11-tetraazabicyclo[6.6.2]-hexadecan (DO2A), 1,4,7,10-tetraazacyclododecan-N,N',N'',N'''-tetraacetic acid (DOTA), 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphat) (DPDP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis (hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2] hexadecane (TE2A), 1,4,8,11-tetraazacyclododecane-1,4,8, 11-tetraacetic acid (TETA), terpyridin-bis(methyleneamintetraacetic acid (TMT), 1,4,7,10-tetraazacyclo-tridecan-N,N', N'',N'''-tetraacetic acid (TRITA), triethylenetetraaminehexaacetic acid (TTHA), N,N'-bis[(6-carboxy-2-pyridyl)methyl]-4,13-diaza-18-crown-6 ($H_2$macropa), and 4-amino-4-{2-[(3-hydroxy-1,6-dimethyl-4-oxo-1,4-dihydro-pyridin-2-ylmethyl)-carbamoyl]-ethyl}heptanedioic acid bis-[(3-hydroxy-1,6-dimethyl-4-oxo-1,4-dihydro-pyridin-2-ylmethyl)-amide] (THP). Such a residue is obtainable by covalently binding a carboxyl group contained in the chelating agent to the remainder of the compound via an ester or an amide bond, preferably an amide bond.

The term "alkyl" as used herein include reference to a straight or branched chain alkyl moiety having 1, 2, 3, 4, 5, 6, 7, 8, 9 or 10 carbon atoms. The term includes reference to, for example, methyl, ethyl, propyl (n-propyl or isopropyl), butyl (n-butyl, sec-butyl or tert-butyl), pentyl, hexyl and the like. In particular, alkyl may be a "$C_1$-$C_4$ alkyl", i.e. an alkyl having 1, 2, 3 or 4 carbon atoms; or a "$C_1$-$C_6$ alkyl", i.e. an alkyl having 1, 2, 3, 4, 5 or 6 carbon atoms; or a "$C_1$-$C_3$ alkyl", i.e. an alkyl having 1, 2 or 3 carbon atoms. The term "lower alkyl" includes reference to alkyl groups having 1, 2, 3 or 4 carbon atoms.

The term "cycloalkyl" as used herein includes reference to an alicyclic moiety having 3, 4, 5 or 6 carbon atoms. The group may be a bridged or polycyclic ring system. More often cycloalkyl groups are monocyclic. This term includes reference to groups such as cyclopropyl, cyclobutyl, cyclopentyl, cyclohexyl and the like.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. For example, a heterocyclic may comprise 3, 4, or 5 ring carbon atoms and 1 or 2 ring heteroatoms selected from nitrogen and oxygen. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent radical derived from an aryl and heteroaryl, respectively.

The term "alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms, e.g. 1, 2 or 3 carbon atoms. This term includes reference to, for example, methoxy, ethoxy, propoxy, isopropoxy, butoxy, tert-butoxy, pentoxy, hexoxy and the like. The term "lower alkoxy" includes reference to alkoxy groups having 1, 2, 3 or 4 carbon atoms. An alkoxy group, in particular a lower alkoxy (e.g. an alkoxy having 2 carbon atoms), may be provided as a polyalkoxy, i.e. as a linear or branched (e.g. as a linear) chain of repeating alkoxy units.

The term "substituted" as used herein in reference to a moiety means that one or more, especially up to 5, more especially 1, 2 or 3, of the hydrogen atoms in said moiety are replaced independently of each other by the corresponding number of the described substituents. Unless otherwise specified, exemplary substituents include —OH, —CN, —NH$_2$, =O, -halo, —C$_1$-C$_6$ alkyl, —C$_2$-C$_6$ alkenyl, —C$_1$-C$_6$ haloalkyl, —C$_1$-C$_6$ haloalkoxy and —C$_2$-C$_6$ haloalkenyl, —C$_1$-C$_6$ alkylcarboxylic acid (e.g. —CH$_3$COOH or —COOH). Where the substituent is a —C$_1$-C$_6$ alkyl or —C$_1$-C$_6$ haloalkyl, the C$_1$-C$_6$ chain is optionally interrupted by an ether linkage (—O—) or an ester linkage (—C(O)O—). Exemplary substituents for a substituted alkyl may include —OH, —CN, —NH$_2$, =O, -halo, —CO$_2$H, —C$_1$-C$_6$ haloalkyl, —C$_1$-C$_6$ haloalkoxy and —C$_2$-C$_6$haloalkenyl, —C$_1$-C$_6$ alkylcarboxylic acid (e.g. —CH$_3$COOH or —COOH). For example, exemplary substituents for an alkyl may include —OH, —CN, —NH$_2$, =O, -halo.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled person.

Where steric issues determine placement of substituents on a group, the isomer having the lowest conformational energy may be preferred. For example, the preferred state for carbocyanines (e.g. Cy-dyes) may be the all-trans conformation, as this represents the ground state (see, e.g., A. M. Kolesnikov and E. A. Mikhailenko, *Russian Chemical Reviews*, (1987), 56, 275-287; W. West et al., *Journal of Physical Chemistry*, (1967), 71, 1316-1326; and P. J. Wheatley, *Journal of the Chemical Society*, (1959), 4096-4100).

Where a compound, moiety, process or product is described as "optionally" having a feature, the disclosure includes such a compound, moiety, process or product having that feature and also such a compound, moiety, process or product not having that feature. Thus, when a moiety is described as "optionally substituted", the disclosure comprises the unsubstituted moiety and the substituted moiety.

Where two or more moieties are described as being "independently" or "each independently" selected from a list of atoms or groups, this means that the moieties may be the same or different. The identity of each moiety is therefore independent of the identities of the one or more other moieties.

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

The term "pharmaceutically acceptable salts" is meant to include salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may have enriched levels (e.g. at least 50% or at least 75%) of stable isotopes, such as deuterium ($^2$H) or carbon-13 ($^{13}$C), at one or more atoms of the compound. For example, the compounds may comprise radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

The term "radiolabel" as used herein refers to a radioactive isotope that readily forms a cation. Exemplary radiolabels include $^{44}$Sc, $^{47}$Sc, $^{51}$Cr, $^{52m}$Mn, $^{58}$Co, $^{52}$Fe, $^{56}$Ni, $^{57}$Ni, $^{62}$Cu $^{64}$Cu $^{67}$Cu $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F, such as $^{18}$F—[AlF]$^{2+}$. Exemplary radiolabels also include $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th, or a cationic molecule comprising $^{18}$F. Preferred radiolabels may include $^{68}$Ga, $^{90}$Y, $^{177}$Lu, $^{212}$Bi, and $^{213}$Bi. A radiolabel may be a γ-emitter, i.e. a radiolabel that when it decays emits γ radiation; a β-emitter, i.e. a radiolabel that when it decays and emits a β particle; or and α-emitter, i.e. a radiolabel that when it decays emits an α particle. Exemplary γ-emitters include $^{99m}$Tc and $^{111}$In. Exemplary β-emitters include $^{90}$Y, $^{166}$Ho and $^{68}$Ga, $^{177}$Lu. Exemplary α-emitters include $^{225}$Ac, $^{224}$Ra and $^{213}$Bi. A "chelated radiolabel" represents a radiolabel (e.g. radioactive cation) that is complexed with a multidentate ligand. The chelating moieties described herein represent multidentate ligands of use in accordance with the present disclosure. Exemplary multidentate ligands of use in accordance with the present disclosure include -MAS$_3$, -MAG$_3$, -DOTA-GA, -DOTA, -DTPA.

The term "pharmaceutical formulation" as used herein includes reference to a formulation comprising at least one active compound and optionally one or more additional pharmaceutically acceptable ingredients, for example a pharmaceutically acceptable carrier. Where a pharmaceutical formulation comprises two or more active compounds, or comprises at least one active compound and one or more additional pharmaceutically acceptable ingredients, the pharmaceutical formulation is also a pharmaceutical composition. Unless the context indicates otherwise, all references to a "formulation" herein are references to a pharmaceutical formulation.

The term "product" or "product of the invention" as used herein includes reference to any product containing a compound of the present invention. In particular, the term product relates to compositions and formulations containing a compound of the present invention, such as a pharmaceutical composition, for example.

The term "therapeutically effective amount" as used herein refers to an amount of a drug, or pharmaceutical agent that, within the scope of sound pharmacological judgment, is calculated to (or will) provide a desired therapeutic response in a mammal (animal or human). The therapeutic response may for example serve to cure, delay the progression of or prevent a disease, disorder or condition.

The term "imaging effective amount" as used herein refers to an amount of a compound, or formulation, that within sound clinical or experimental experience, is calculated to (or will) provide a sufficient response for imaging, e.g. based on detection of radioactive decay or fluorescence. Compounds or formulations used for imaging may be provided in an imaging effective amount.

Compounds

Compounds of the invention may be useful as tracers. In particular, compounds of the invention combine a probe (e.g. a PSMA probe) with a fluorophore and moiety that may be radiolabeled, e.g. by chelating a radioactive isotope. These compounds, when they comprise a radiolabel, may be considered a hybrid tracer, as the probe portion is conjugated to two labels that can serve a complementary purpose: a fluorophore and a radiolabel.

The compounds may be considered small molecule hybrid PSMA tracers that benefit from a generic (targeting vector portion)-(hydrophobic dye portion)-(chelate portion) design. The efficacy of such a tracer can be optimized by fine-tuning individual portions of the compounds, as is demonstrated herein. At the same time, these findings also suggest that this design concept remains valid when e.g. the targeting vector, dye, or chelate is varied. For example, the dye portion may comprise a Cy5 or a Cy7 analogue and the chelate portion may comprise a chelating moiety as disclosed herein, such as a MAS3 or a DOTAGA. The choice of the dye influences the wavelength used for surgical guidance (far red for Cy5 or near-infrared for Cy7). Appropriate choice of the chelate portion accommodates the chelation of different radiolabels. For example, a chelator that may be used with an alpha emitter (e.g. $^{225}$Ac, $^{224}$Ra, $^{211}$Bi), may be suitable for use with therapeutic isotopes; while a chelator that may be used with a gamma emitter (e.g. $^{99m}$Tc, $^{111}$In), may be suitable for use with radiolabel imaging isotopes. Most chelates are able to coordinate different radiolabels. For example, DOTAGA may chelate $^{111}$In, $^{68}$Ga, $^{177}$Lu, etc.; and MAS3 may chelate $^{99m}$Tc, $^{188}$Re, etc.

Targeting vector: In order to create an optimally designed PSMA-targeting compound, the compound needs to be designed so that the targeting vector portion, e.g. —EuX (X is K, FA, PG or E), should be carefully positioned in the enzyme. The targeting-vector utilizes predominantly the aspartate (S1 position) and glutamate (S1' position) binding sites, while urea can coordinate to $Zn^{2+}$.

Hydrophobic dye unit: Appropriate hydrophobic (aromatic) substituents can bind into an accessory hydrophobic pocket that is located next to the S1 position, thereby improving the receptor affinity further. Hence many PSMA targeting radiotracers hold spacer molecules that facilitate secondary binding in this accessory hydrophobic pocket. Furthermore it has been demonstrated herein that appropriate placement of at least one anionic moiety (such as —SO$_3^-$) can further improve receptor affinity. Provided herein are PSMA targeting compounds that use bifunctional dye moieties as linker molecules, which represents a paradigm shift in fluorescent PSMA tracer design. This design concept is demonstrated for bifunctional Cy5 analogues and Cy7 analogues and thus seems generic for all bifunctional cyanine dye analogues.

Chelate unit: In small molecule PSMA-tracers, traditionally the radioisotope binding chelate is positioned outside the pharmacophore. Many different chelates have been used with various radioisotopes, as reported for applications ranging from diagnostics to therapeutics. The bifunction dyes replace traditional spacers in the compounds of the invention. The new hybrid tracer design of the compounds of the invention also accommodates the integration of different chelates e.g. MAS3 and DOTAGA. As the skilled person would appreciate, this teaching may be extended to accommodate other common chelates e.g. MAG3, DOTA, NOTA and matching isotopes.

In one aspect, the invention provides compounds of formula I (or formula Ia) as previously described or a pharmaceutically acceptable salt, stereoisomer, or prodrug thereof. In embodiments, one or more of $R_1$, $R_2$, $R_3$, $R_4$, $R_5$, $R_6$, $R_7$, $R_8$, $R_9$, $R_{10}$, V, W, $Y_1$, $Y_2$, Z, $L_1$, $L_2$, $L_3$, $L_4$, m, n and p are as described in the following paragraphs:

At least one of the substituents $R_1$, $R_2$, $R_5$, $R_7$, $R_8$ of the first indole moiety may differ from at least one of the substituents $R_3$, $R_4$, $R_6$, $R_9$, $R_{10}$ of the second indole moiety, thereby providing an asymmetric dye portion. For present purposes, the dye portion represents the first indole moiety, second indole moiety, the polymethine linker and substituents $R_1$-$R_{10}$. Asymmetric in the context of the dye portion means that, for at least one corresponding pair of substituents of the first and second indole moieties, the substituents are different. That is, in an asymmetric dye portion, at least one of the following conditions apply: $R_1$ differs from $R_3$, $R_2$ differs from $R_4$, $R_5$ differs from $R_6$, or $R_7$ and $R_8$ differ from $R_9$ and $R_{10}$. For example, $R_1$ may differ from $R_3$. For example, $R_2$ may differ from $R_4$.

We have determined that compounds of formula I or formula Ia that have an asymmetric dye portion demonstrate enhanced utility as tracers. For example, compounds where at least one of $R_1$ and $R_2$ (but not $R_3$ and $R_4$) have a charge (e.g. a negative charge, such as sulfonate) have demonstrated surprisingly good clearance and tumour specificity. Without wishing to be bound by any theory, it is believed that these advantages may be due to alterations in the binding activity, due to the role of the dye as part of the compounds pharmacophore, (evidence by, e.g., lower IC-50) as well as alterations in renal clearance, which has the potential to provide reduced toxicity.

$R_1$ may be selected from sulfonate, carboxyl, phosphonate, amine, azide and H. $R_1$ may be selected from sulfonate, carboxyl, phosphonate and H. $R_1$ may be selected from sulfonate, carboxyl and phosphonate. $R_1$ may be selected from amine, azide and H. $R_1$ may be selected from amine and azide. $R_1$ may be sulfonate. $R_1$ may be carboxyl. $R_1$ may phosphonate. $R_1$ may be amine. $R_1$ may be azide. $R_1$ may be H.

$R_2$ may be selected from sulfonate, carboxyl, phosphonate, amine, azide and H. $R_2$ may be selected from sulfonate, carboxyl, phosphonate and H. $R_2$ may be selected from sulfonate, carboxyl and phosphonate. $R_2$ may be selected from amine, azide and H. $R_2$ may be selected from amine and azide. $R_2$ may be sulfonate. $R_2$ may be carboxyl. $R_2$ may phosphonate. $R_2$ may be amine. $R_2$ may be azide. $R_2$ may be H.

$R_1$ and $R_2$ together may form an aryl that is substituted with one or two groups each independently selected from sulfonate, carboxyl, phosphonate, amine and azide. $R_1$ and $R_2$ together may form an aryl that is substituted with one group selected from sulfonate, carboxyl, phosphonate, amine and azide. $R_1$ and $R_2$ together may form an unsubstituted aryl. The aryl may be or comprise phenyl. The aryl may be or comprise napthyl.

$R_3$ may be selected from sulfonate, carboxyl, phosphonate, amine, azide and H. $R_3$ may be selected from sulfonate, carboxyl, phosphonate and H. $R_3$ may be selected from sulfonate, carboxyl and phosphonate. $R_3$ may be selected from amine, azide and H. $R_3$ may be selected from amine and azide. $R_3$ may be sulfonate. $R_3$ may be carboxyl. $R_3$ may phosphonate. $R_3$ may be amine. $R_3$ may be azide. $R_3$ may be H.

$R_4$ may be selected from sulfonate, carboxyl, phosphonate, amine, azide and H. $R_4$ may be selected from sulfonate, carboxyl, phosphonate and H. $R_4$ may be selected from sulfonate, carboxyl and phosphonate. $R_4$ may be selected from amine, azide and H. $R_4$ may be selected from amine and azide. $R_4$ may be sulfonate. $R_4$ may be carboxyl. $R_4$ may phosphonate. $R_4$ may be amine. $R_4$ may be azide. $R_4$ may be H.

$R_3$ and $R_4$ together may form an aryl that is substituted with one or two groups each independently selected from sulfonate, carboxyl, phosphonate, amine and azide. $R_3$ and $R_4$ together may form an aryl that is substituted with one group selected from sulfonate, carboxyl, phosphonate, amine and azide. $R_3$ and $R_4$ together may form an unsubstituted aryl. The aryl may be or comprise phenyl. The aryl may be or comprise naphthyl.

At least 1 of $R_1$ and $R_2$ may be other than H. At least 1 of $R_3$ and $R_4$ may be other than H. At least one of $R_1$, $R_2$, $R_3$ and $R_4$ may be other than H.

In particular, at least one of $R_1$ and $R_2$ (e.g. $R_1$) may be selected from sulfonate, carboxyl, phosphonate, amine and azide; and $R_3$ and $R_4$ may be H. For example, at least one of $R_1$ and $R_2$ (e.g. $R_1$) may be selected from sulfonate, carboxyl and phosphonate; and $R_3$ and $R_4$ may be H.

$R_5$ may be selected from sulfonate, carboxyl, phosphonate, amine, azide, $CH_3$, $CH_2CH_3$ and H. $R_5$ may be selected from sulfonate, carboxyl, phosphonate and H. $R_5$ may be selected from sulfonate, carboxyl and phosphonate. $R_5$ may be selected from amine, azide and H. $R_5$ may be selected from amine and azide. $R_5$ may be sulfonate. $R_5$ may be carboxyl. $R_5$ may phosphonate. $R_5$ may be amine. $R_5$ may be azide. $R_5$ may be H.

$R_6$ may be selected from sulfonate, carboxyl, phosphonate, amine, azide, $CH_3$, $CH_2CH_3$ and H. $R_6$ may be selected from sulfonate, carboxyl, phosphonate and H. Re may be selected from sulfonate, carboxyl and phosphonate. $R_6$ may be selected from amine, azide and H. $R_6$ may be selected from amine and azide. $R_6$ may be sulfonate. $R_6$ may be carboxyl. $R_6$ may phosphonate. $R_6$ may be amine. $R_6$ may be azide. $R_6$ may be H.

Each of $R_7$, $R_8$, $R_9$ and $R_{10}$ may be independently selected from sulfonate, carboxyl, phosphonate, amine, azide, $CH_3$, $CH_2CH_3$ and H. Each of $R_7$, $R_8$, $R_9$ and $R_{10}$ may be independently selected from, $CH_3$, $CH_2CH_3$ and H. Each of $R_7$, $R_8$, $R_9$ and $R_{10}$ may be independently selected from $CH_3$ and $CH_2CH_3$. Each of $R_7$, $R_8$, $R_9$ and $R_{10}$ may be $CH_3$. Each of $R_7$, $R_8$, $R_9$ and $R_{10}$ may be $CH_2CH_3$. Each of $R_7$, $R_8$, $R_9$ and $R_{10}$ may be H.

In an embodiment, not more than two of the substituents $R_1$, $R_2$, $R_5$, $R_7$, $R_8$ of the first indole moiety are sulfonate, carboxyl, or phosphonate; and/or not more than two of the substituents $R_3$, $R_4$, $R_6$, $R_9$, $R_{10}$ of the second indole moiety are sulfonate, carboxyl, or phosphonate. In an embodiment, at least three of $R_1$, $R_2$, $R_5$, $R_7$, $R_8$ are independently selected from $CH_3$, $CH_2CH_3$ and H; and/or at least three of $R_3$, $R_4$, $R_6$, $R_9$, $R_{10}$ are independently selected from $CH_3$, $CH_2CH_3$ and H.

n may be 2. n may be 3.

V may be —$CH_2$—. V may be —$CH_2CH_2O$—. m may be 4, 5, 6, 7, 8, 9, 10, 11 or 12. m may be 4, 5, 6, 7 or 8; e.g. m may be 4, 5 or 6. For example, m may be 5.

W may be —$CH_2$—. W may be —$CH_2CH_2O$—. p may be 4, 5, 6, 7, 8, 9, 10, 11 or 12. p may be 4, 5, 6, 7 or 8; e.g. p may be 4, 5 or 6. For example, p may be 5.

$Y_1$ may be —EuK, —EuFA, —EuPG, -$L_1$-EuK, -$L_1$-EuFA, -$L_1$-EuPG or -$L_3$-EuE; where EuK, EuFA, EuPG, EuE are as defined in Table 1. $Y_1$ may be —EuK, —EuFA, —EuPG, -$L_3$-EuE. $Y_1$ may be -$L_1$-EuK, -$L_1$-EuFA, -$L_1$-EuPG or -$L_3$-EuE. $Y_1$ may be —EuK. $Y_1$ may be -EuFA. $Y_1$ may be —EuPG. $Y_1$ may be -$L_1$-EuK. $Y_1$ may be -$L_1$-EuFA. $Y_1$ may be -$L_1$-EuPG. $Y_1$ may be -$L_3$-EuE.

$Y_2$ may be $-L_4$-EuK, $-L_4$-EuFA, $-L_4$-EuPG, —EuE, or $-L_2$-EuE; where EuK, EuFA, EuPG, EuE are as defined in Table 1. $Y_2$ may be $-L_4$-EuK, $-L_4$-EuAF, $-L_4$-EuPG. $Y_2$ may be —EuE or $-L_2$-EuE. $Y_2$ may be $-L_2$-EuK. $Y_2$ may be $-L_2$-EuFA. $Y_2$ may be $-L_2$-EuPG. $Y_2$ may be —EuE. $Y_2$ may be $-L_2$-EuE.

Z may be a chelating moiety that is a residue of a chelating agent as defined herein. For example, Z may be or comprise a residue of bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]-hexadecan (DO2A), 1,4,7,10-tetraazacyclododecan-N,N',N'',N'''-tetraacetic acid (DOTA), 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphat) (DPDP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclo-tridecan-N,N',N'',N'''-tetraacetic acid (TRITA), triethylenetetraaminehexaacetic acid (TTHA), N,N'-bis[(6-carboxy-2-pyridyl)methyl]-4,13-diaza-18-crown-6 ($H_2$macropa), and 4-amino-4-{2-[(3-hydroxy-1,6-dimethyl-4-oxo-1,4-dihydro-pyridin-2-ylmethyl)-carbamoyl]-ethyl}heptanedioic acid bis-[(3-hydroxy-1,6-dimethyl-4-oxo-1,4-dihydro-pyridin-2-ylmethyl)-amide] (THP). Z may be $-MAS_3$, $-MAG_3$, -DOTA-GA, -DOTA, -DTPA, $-L_2-MAS_3$, $-L_2-MAG_3$, $-L_2$-DOTA-GA, $-L_2$-DOTA, $-L_2$-DTPA; where $MAS_3$, $MAG_3$, DOTA-GA, DOTA, DTPA are as defined in Table 1. Z may be $-MAS_3$, $-MAG_3$, -DOTA-GA, -DOTA, -DTPA. Z may be $-L_2-MAS_3$, $-L_2-MAG_3$, $-L_2$-DOTA-GA, $-L_2$-DOTA, $-L_2$-DTPA, Z may be $-MAS_3$ or $-MAG_3$. Z may be -DOTA-GA or -DOTA. Z may be $-MAS_3$. Z may be $-MAG_3$. Z may be -DOTA-GA. Z may be -DOTA. Z may be -DTPA. Z may be $-L_2-MAS_3$. Z may $-L_2-MAG_3$. Z may be $-L_2$-DOTA-GA. Z may be $-L_2$-DOTA. Z may be $-L_2$-DTPA.

TABLE 1

Exemplary substituents $Y_1$, $Y_2$ and Z, where "~~" represents the point of attachment to the remainder of the compound.

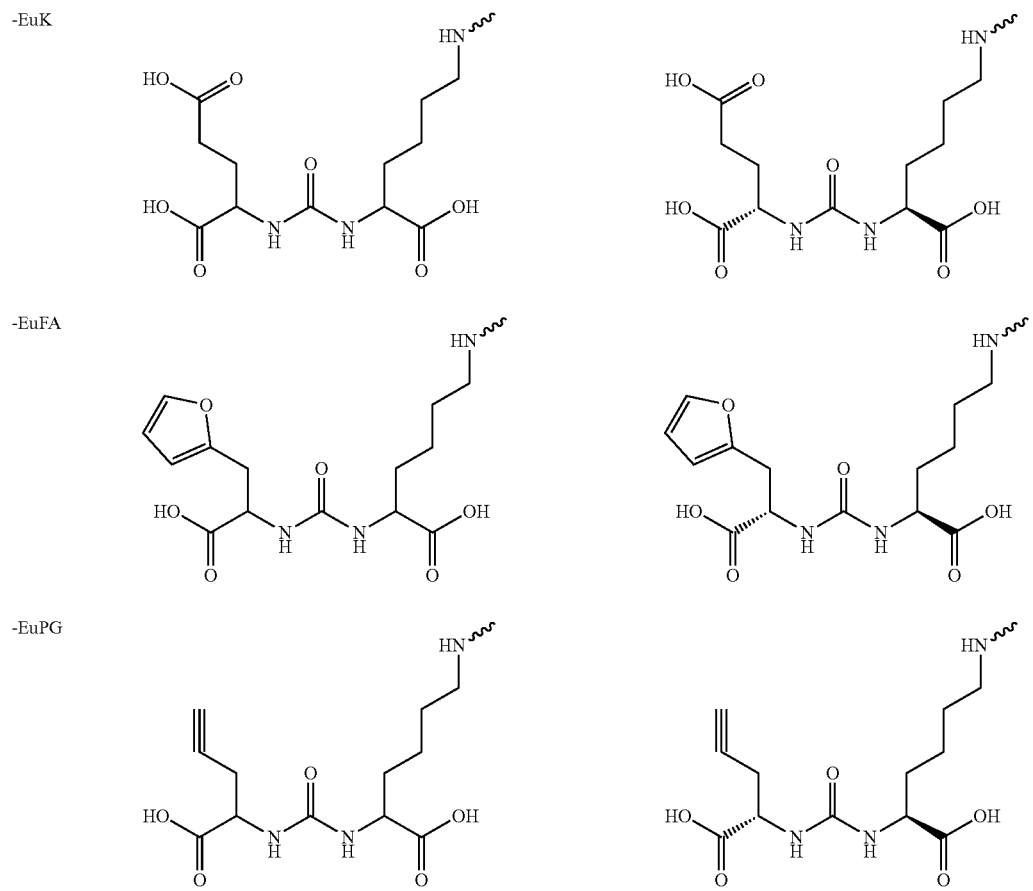

TABLE 1-continued
Exemplary substituents $Y_1$, $Y_2$ and Z, where "⌇" represents the point of attachment to the remainder of the compound.
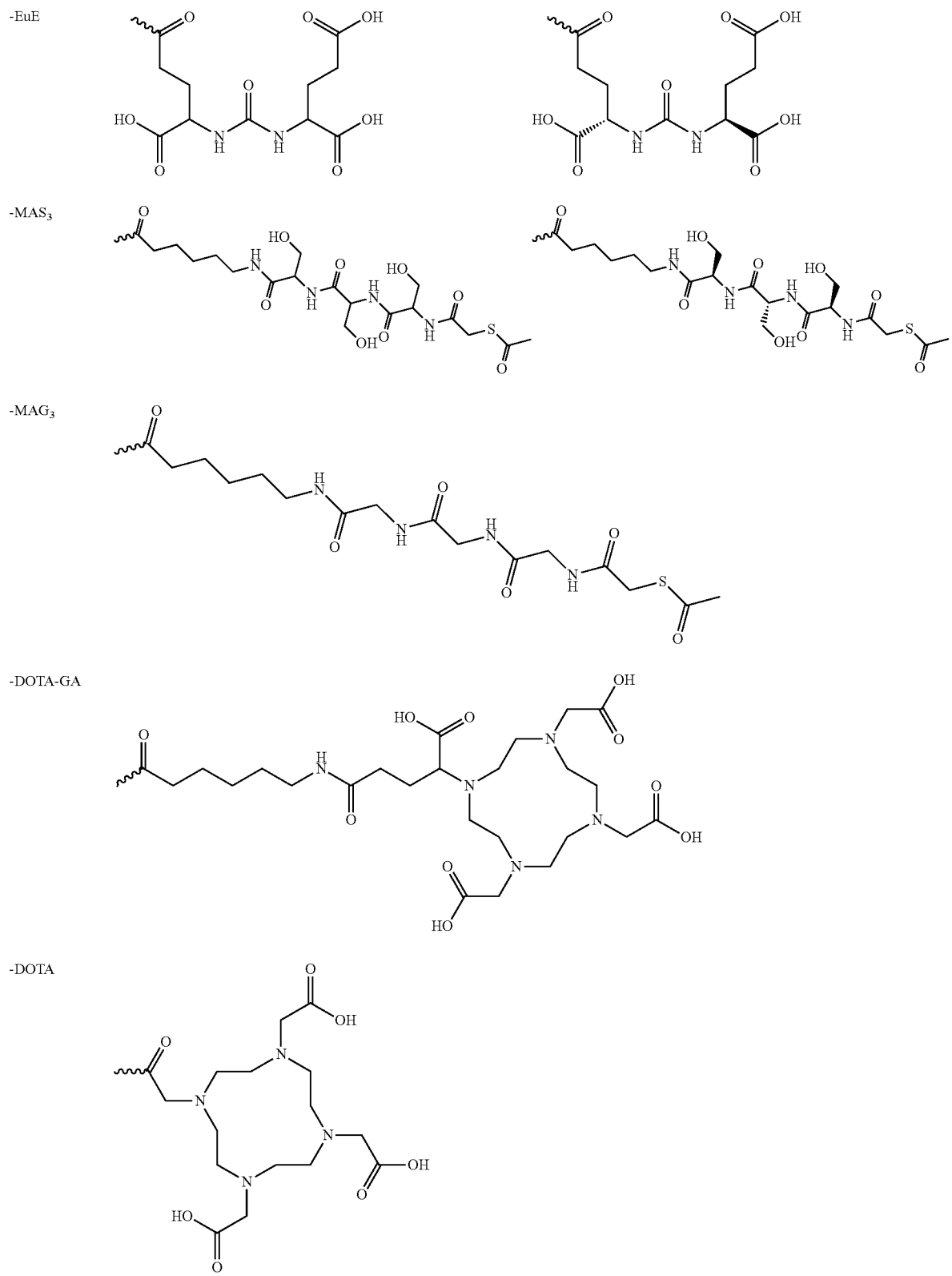

TABLE 1-continued

Exemplary substituents $Y_1$, $Y_2$ and Z, where "⌇" represents the point of attachment to the remainder of the compound.

--DTPA

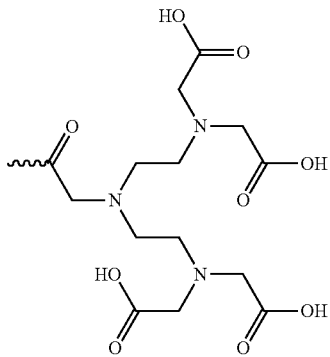

$L_1$ may be a linker of formula —NH—$R_{12}$—C(O)—, where $R_{12}$ is a bond, or a substituted or unsubstituted alkyl. For example, $R_{12}$ may be a bond. For example, $R_{12}$ may be a substituted or unsubstituted straight or branched alkyl moiety having 2, 3, 4, 5, 6, 7 or 8 carbon atoms. $L_1$ may be a residue of lysine, a residue of ornithine, a residue of aspartic acid, a residue of glutamic acid or —NH—($C_4$-$C_7$alkyl)-C(O)—. $L_1$ may be a residue of lysine. $L_1$ may be a residue of ornithine. $L_1$ may be a residue of aspartic acid. $L_1$ may be a residue of glutamic acid. $L_1$ may be —NH—($C_4$-$C_7$alkyl)-NH—, e.g. $L_1$ may be —NH—($C_5$alkyl)-NH—, or $L_1$ may be —NH—($C_6$alkyl)-NH—.

$L_2$ may be a linker of formula —C(O)—$R_{13}$—NH—, where $R_{13}$ is a bond, or a substituted or unsubstituted alkyl. For example, $R_{13}$ may be a bond. For example, $R_{13}$ may be a substituted or unsubstituted straight or branched alkyl moiety having 2, 3, 4, 5, 6, 7 or 8 carbon atoms. $L_2$ may be a residue of lysine, a residue of ornithine, a residue of aspartic acid, a residue of glutamic acid or —C(O)—($C_4$-$C_7$alkyl)-NH—. $L_2$ may be a residue of lysine. $L_2$ may be a residue of ornithine. $L_2$ may be a residue of aspartic acid. $L_2$ may be a residue of glutamic acid. $L_2$ may be —NH—($C_4$-$C_7$alkyl)-NH—, e.g. $L_2$ may be —NH—($C_5$alkyl)-NH—, or $L_2$ may be —NH—($C_6$alkyl)-NH—.

$L_3$ may be a linker of formula —NH—$R_{14}$—NH—, where $R_{14}$ is a substituted or unsubstituted alkyl. For example, $R_{14}$ may be a substituted or unsubstituted straight or branched alkyl moiety having 4, 5, 6, 7 or 8 carbon atoms. $L_3$ may be a residue of lysine, a residue of ornithine or —NH—($C_4$-$C_7$alkyl)-NH—. $L_3$ may be a residue of lysine. $L_3$ may be a residue of ornithine. $L_3$ may be —NH—($C_4$-$C_7$alkyl)-NH—, e.g. $L_3$ may be —NH—($C_5$alkyl)-NH—, or $L_3$ may be —NH—($C_6$alkyl)-NH—.

$L_4$ may be a linker of formula —C(O)—$R_{15}$—C(O)—, where $R_{13}$ is a substituted or unsubstituted alky. For example, $R_{13}$ may be a substituted or unsubstituted straight or branched alkyl moiety having 4, 5, 6, 7 or 8 carbon atoms. $L_4$ may be a residue of aspartic acid, a residue of glutamic acid or —C(O)—($C_4$-$C_7$alkyl)-C(O)—. $L_4$ may be a residue of aspartic acid. $L_4$ may be a residue of glutamic acid. $L_4$ may be —C(O)—($C_4$-$C_7$alkyl)-(CO)—, e.g. $L_4$ may be —C(O)—($C_5$alkyl)-(CO)—, or $L_4$ may be —C(O)—($C_6$alkyl)-C(O)—.

The compound may be a compound selected from:

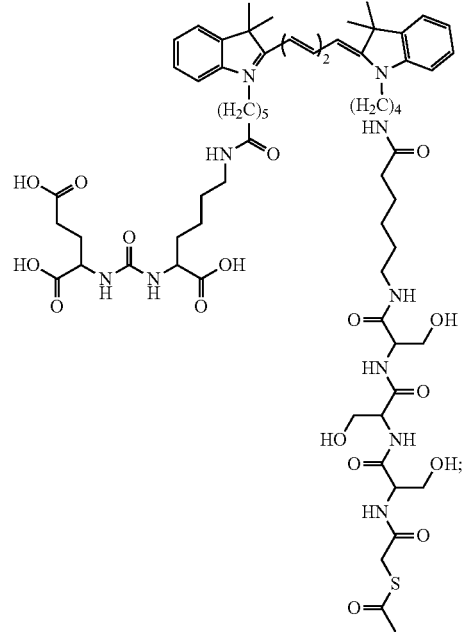

21
-continued
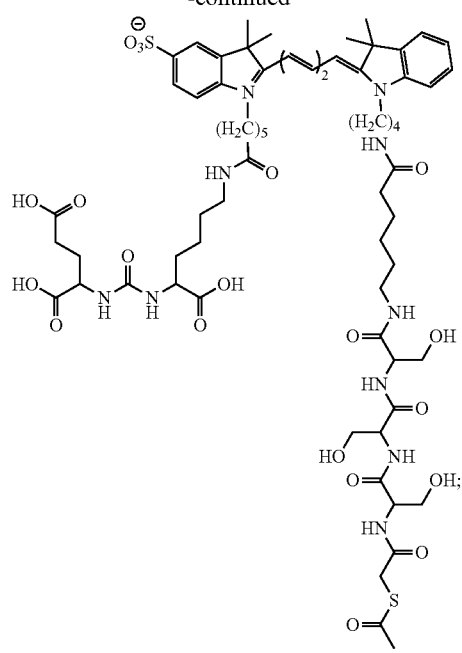
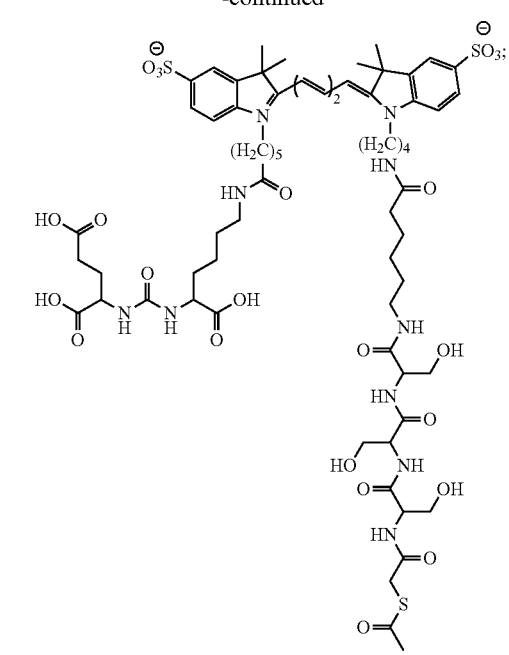
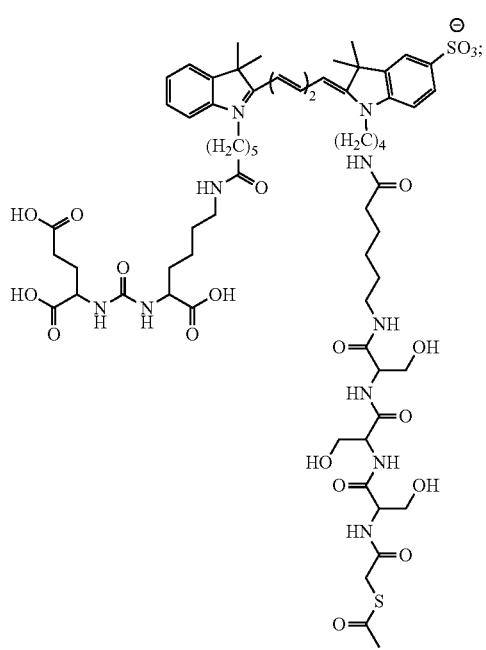
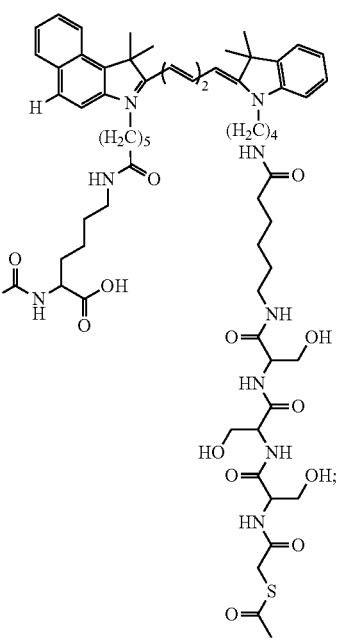

23
-continued
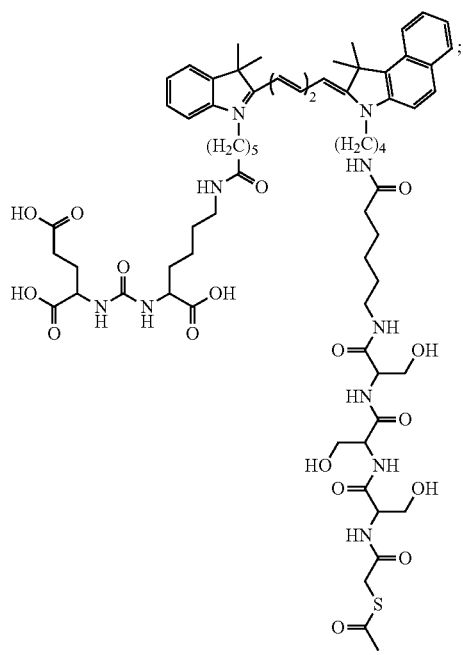
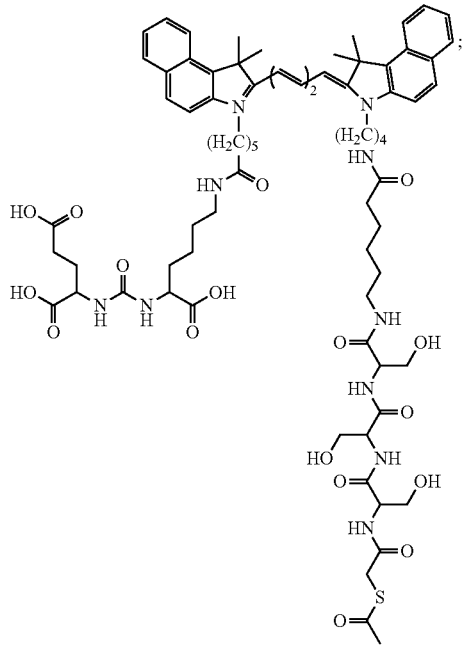
24
-continued
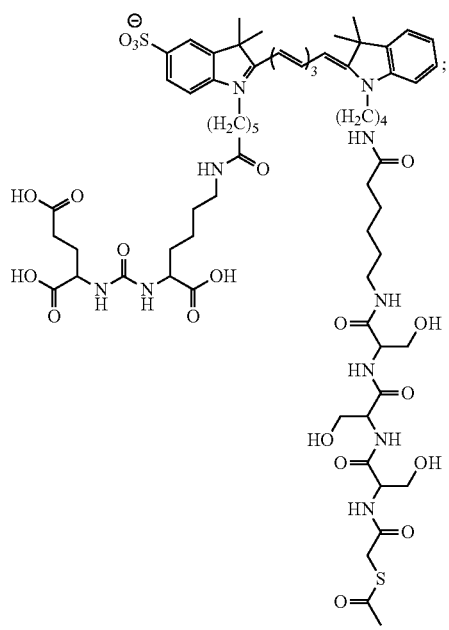
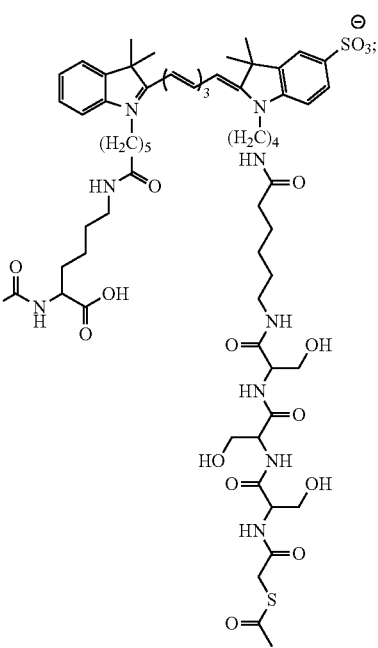

25
-continued
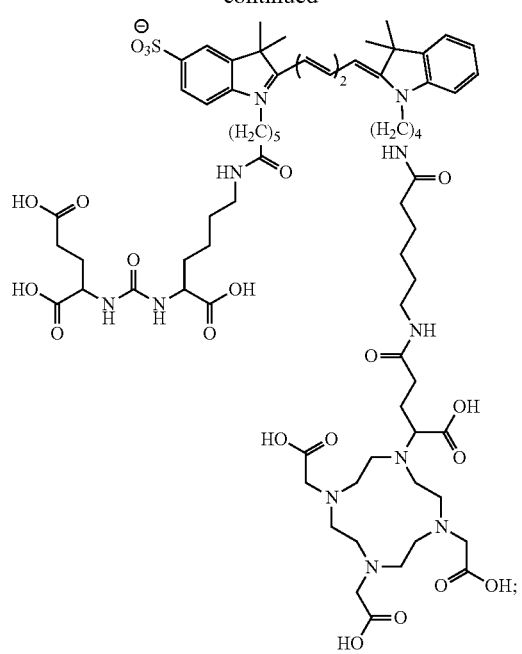
26
-continued
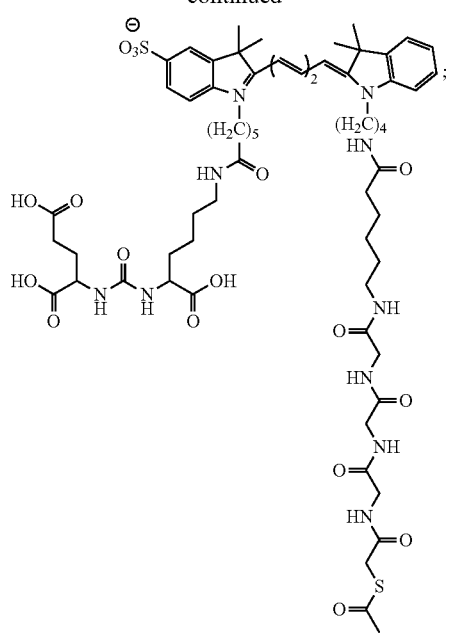
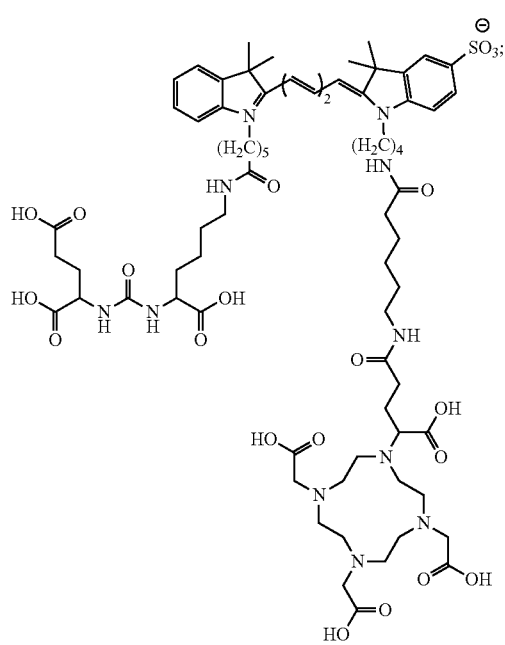

27
-continued
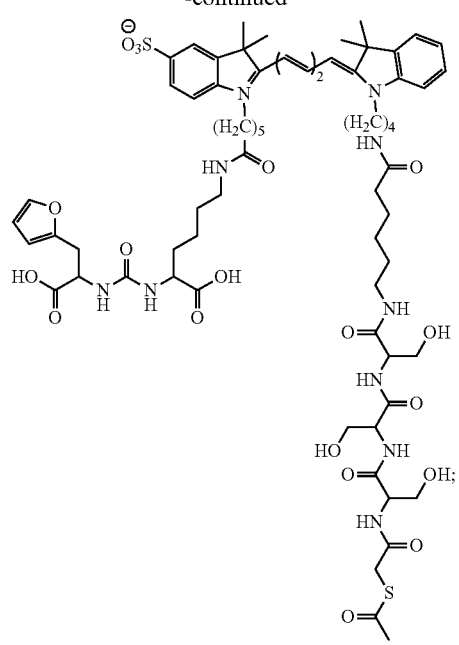
28
-continued
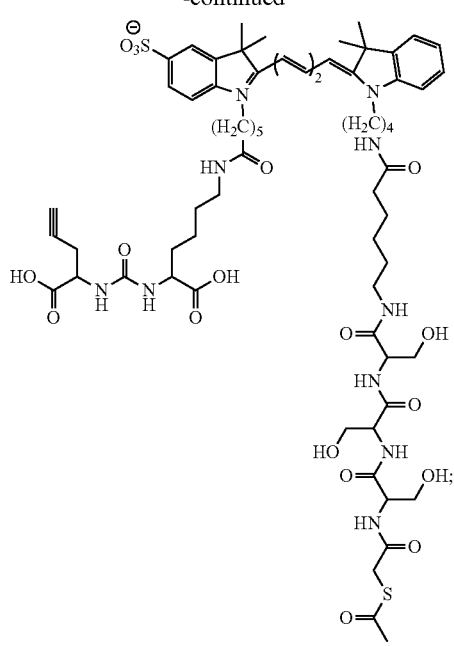
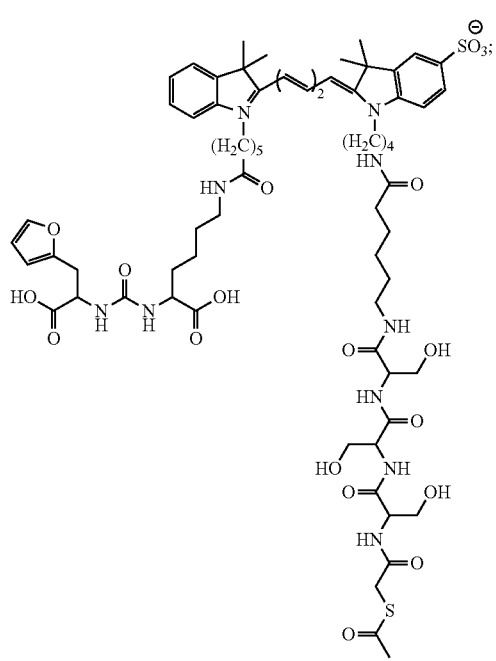
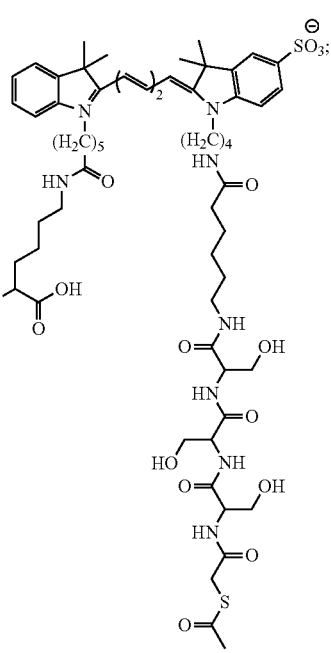

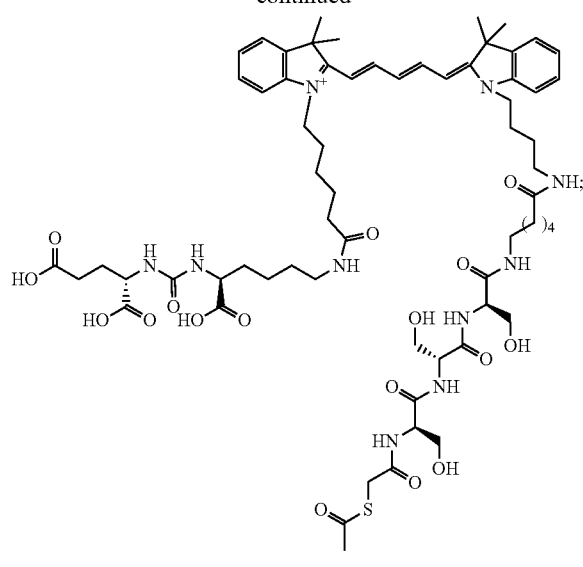
EuK-Cy5-MAS₃
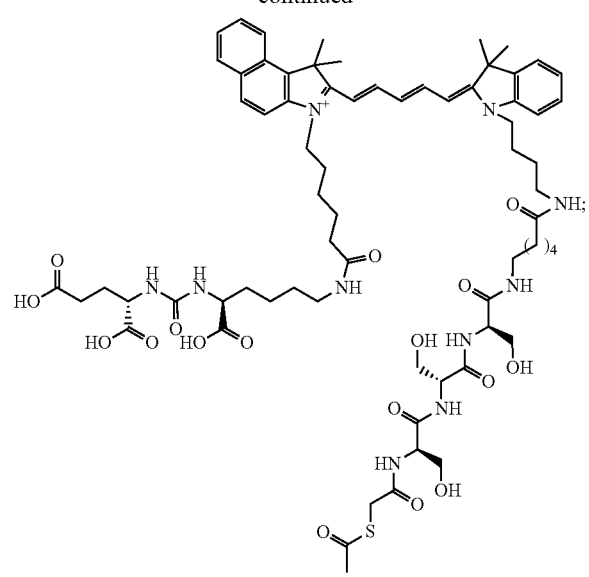
EuK(Ar)-Cy5-MAS₃
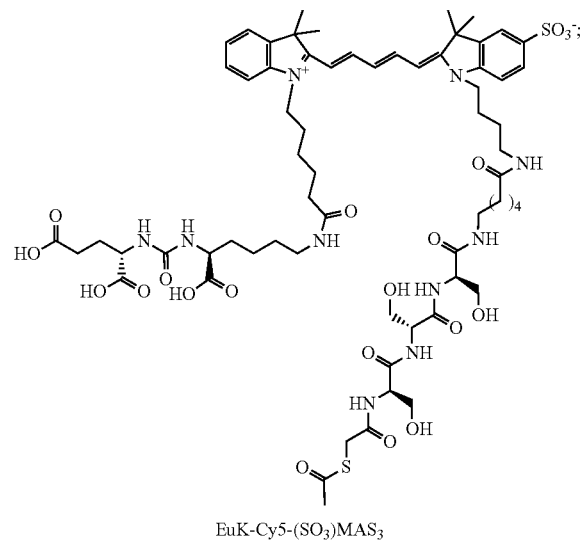
EuK(SO₃)-Cy5-MAS₃
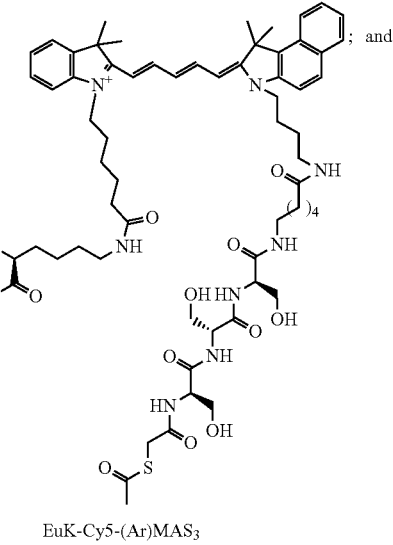
EuK-Cy5-(SO₃)MAS₃
EuK-Cy5-(Ar)MAS₃

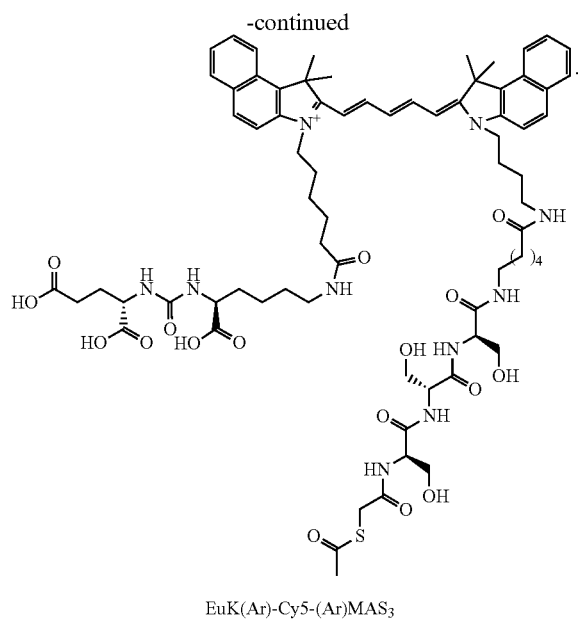

EuK(Ar)-Cy5-(Ar)MAS₃

The compound may comprise a chelated radiolabel. The chelated radiolabel may be selected from a γ-emitter (e.g. $^{99m}$Tc, $^{111}$In), a β-emitter (e.g. $^{90}$Y $^{166}$Ho, $^{68}$Ga, $^{177}$Lu), and an α-emitter (e.g. $^{225}$Ac, $^{224}$Ra, $^{213}$Bi), or a combination thereof. The chelated radiolabel may be a γ-emitter; e.g. $^{99m}$Tc, $^{111}$In, or a combination thereof. The chelated radiolabel may be a R-emitter; e.g. $^{90}$Y, $^{166}$Ho, $^{68}$Ga, $^{177}$Lu, or a combination thereof. The chelated radiolabel may be an α-emitter; e.g. $^{225}$Ac, $^{224}$Ra, $^{213}$Bi, or a combination thereof.

In another aspect, the invention provides compounds of formula II (or formula IIa) as previously described or a pharmaceutically acceptable salt, stereoisomer, or prodrug thereof. In embodiments, one or more of $R_1$, $R_2$, $R_3$, $R_4$, $R_5$, $R_6$, $R_7$, $R_8$, $R_9$, $R_{10}$, V, W, Z, n and p are as defined herein. Compounds of this aspect that are compounds of formula II represent intermediates for the compound of formula I. Compounds of this aspect that are compounds of formula IIa represent intermediates for the compound of formula Ia. In addition, such compounds may be bound to probes (e.g. forming —$V_m$—C(O)-probe) other than —EuK, —EuFA or —EuPG. Thus compounds of formula II may represent useful intermediates for other hybrid probes. Compounds of formula II may comprise a chelated radiolabel as defined herein.

In another aspect, the invention provides compounds of formula III (or formula IIIa) as previously described or a pharmaceutically acceptable salt, stereoisomer, or prodrug thereof. In embodiments, one or more of $R_1$, $R_2$, $R_3$, $R_4$, $R_5$, $R_6$, $R_7$, $R_8$, $R^9$, $R_{10}$, V, W, Y, n and p are as defined herein. Such compounds may be attached to a moiety —Z utilising chemistry known to the skilled person, e.g. providing a compound of formula I (or formula Ia). Thus compounds of formula III represent intermediates of compounds of formula I, while compounds of formula IIIa represent intermediates of compounds of formula Ia.

Formulations and Administration

Compounds of the invention may be administered parenterally, for example the compounds may be administered intravenously or intraprostatically. Compounds of the invention may be administered intravenously. Compounds of the invention may be administered intraprostatically. The compounds may be administered in the form of pharmaceutical preparations comprising the compound either as a free compound or, for example, a pharmaceutically acceptable non-toxic organic or inorganic acid or base addition salt, in a pharmaceutically acceptable dosage form. Depending upon the disorder and imaging requirements, the compositions may be administered at varying doses.

According to a further aspect of the invention there is thus provided a pharmaceutical formulation or composition including a compound of the invention, optionally in admixture with a pharmaceutically acceptable adjuvant, diluents or carrier. The formulation or composition may also comprise a compound that influences in vivo kinetics the compound of the invention. The formulation may also comprise at least one compound that blocks or reduces the uptake of the compound of the invention in an organ (or in multiple organs). For example, the formulation may also comprise a compound that 30 blocks or reduces the uptake of the compound in kidneys and/or salivary glands. Examples of such compounds include mannitol, 2-(phosphonomethyl) pentanedioic acid, monosodium glutamate, succinylated gelatin and albumin fragments.

Pharmaceutical formulations or compositions of this invention for injection may comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters, such as ethyl oleate.

These compositions may also contain adjuvants such as preservative, wetting agents, emulsifying agents and dispersing agents. Inhibition of the action of microorganisms may be ensured by the inclusion of various antibacterial and antifungal agents, for example, paraben, chlorobutanol or phenol sorbic acid. It may also be desirable to include isotonic agents, such as sugars or sodium chloride, for example.

The formulations according to the present subject matter may also contain inactive components. Suitable inactive components are well known in the art and are described in standard textbooks, such as Goodman and Gillman's: The Pharmacological Bases of Therapeutics, 8$^{th}$Ed., Gilman et al, Eds. Pergamon Press (1990), and Remington's Pharmaceutical Sciences, 17$^{th}$ Ed., Mack Publishing Co., Easton, Pa. (1990), both of which are incorporated by reference herein in their entirety.

The formulations may be used in combination with an additional pharmaceutical dosage form to enhance their effectiveness in treating any of the disorders described herein. In this regard, the present formulations may be administered as part of a regimen additionally including any other pharmaceutical and/or pharmaceutical dosage form known in the art as effective for the treatment of any of these disorders. The additional pharmaceutical dosage form may comprise at least one compound that blocks or reduces the uptake of the compound of the invention in an organ (or in multiple organs). For example, the additional pharmaceutical dosage form may comprise a compound that blocks or reduces the uptake of the compound in kidneys and/or salivary glands. Examples of such compounds include mannitol, 2-(phosphonomethyl)pentanedioic acid, monosodium glutamate, succinylated gelatin and albumin fragments. These compounds are also discussed in the following paragraphs.

Manitol. In the kidneys, PSMA is only expressed in the proximal tubules (*Urology* (2007) 70:385-90), where osmotic diuretics such as mannitol exert their pharmacological action. Given that it is not reabsorbed by the renal tubules, mannitol is used to promote diuresis, and thereby increases osmolarity, facilitating water excretion and inhibiting tubular reabsorption of sodium, chloride, and other solutes. Mannitol has therefore been used to reduce the dose of radiolabeled PSMA delivered to the kidneys. (*EJNMMI* (2017) 44:2189-2194).

2-(phosphonomethyl)pentanedioic acid (2-PMPA). 2-PMPA is a PSMA inhibitor has been used by Kratochwil et al. to reduce renal accumulation as a result of subsequent administration. They concluded that PMPA blocks the PSMA receptor, as they hypothesise that "subsequent administration of high-dose PSMA competitor PMPA may no longer block tumor uptake but can still displace the "non-" or "not yet" internalized PSMA ligand from the renal tubular cells, thus improving the projected tumor-to-kidney dose ratio." (*J Nucl Med* (2015) 56:293-298). Later research has found that 2-PMPA is useful for coinjection with PSMA I&T, but that it might reduce the efficient dose since tumour uptake is also significantly reduced. (*Theranostics* (2016) 12:849-861).

Monosodium glutamate (MSG). MSG is a well-studied food additive and can stimulate salivary flow. Rousseau et al used this to block salivary gland uptake of 68GaPSMA-11. (*J Nucl Med* August 2018). They also observed a significant decrease in kidney uptake of this tracer for MSG-treated mice compared to control. Notably, tumour uptake was not significantly decreased (as opposed to coinjection with PMPA).

Succinylated gelatin. Studies have indicated that the coadministration of basic compounds, especially amino acids such as lysine and arginine, significantly reduces the radioactivity concentrations in the kidneys, in some cases up to 60% (*J Nucl Med* (1997) 38:1929-1933; *J Nucl Med* (2002) 46:181-194; *Scand J Clin Lab Invest* (1977) 37:477-486; *Eur J Nucl Med* (1998) 25:201-212). By exploiting this mechanism, researchers have managed to decrease renal accumulation by coadministration of polypeptide-based succinylated gelatin (GELO) plasma expander Gelofusine (*J Nucl Med* (2006) 47:528-533; *J Nucl Med* (2006) 47:432-436).

Albumin fragments. It is known that megalin is involved in the binding and uptake of hydrophilic (radiolabeled) peptides. (*EJNMMI* (2011) 38: 623-632) Albumin is a natural ligand of megalin, but only a small fraction of circulating albumin is filtered in the glomeruli. This small fraction is reabsorbed by, e.g., megalin-mediated endocytosis. Albumin-derived peptide fragments reach higher concentrations in the proximal tubules than intact albumin and are efficient inhibitors of renal reabsorption of different radiolabeled peptides. (*J Nucl Med* (2008) 49:1506-1511; *EJNMMI* (2010) 37:226-234).

Imaging and Other Uses

Compounds of the invention are tracers that are useful for imaging. In particular, compounds of the invention, e.g. of formula I or formula Ia, are useful for imaging tumours expressing PMSA, e.g. prostate cancer tumours. Such tumours include prostate cancer tumours, renal tumours, breast cancer tumours, gliomas, colorectal adenocarcinoma, transitional cell carcinoma, pancreatic ductal adenocarcinoma, gastric adenocarcinoma.

Radiolabelled tracers comprising a PSMA probe have been used in PSMA-targeted diagnostic imaging of prostate cancer. For example, Eder et al, *Bioconjug. Chem.*, 2012, 23(4), 688-697, describes [$^{68}$Ga]PSMA-11 PSMA PET, which utilises a $^{68}$Ga-complex associated with a urea-based PSMA inhibitor to provide PET imaging to image prostate cancer. In another example, 99mTc-PSMA I&S has been successfully used for image guided surgery, but this compound does not allow high-resolution visualisation of tumor or margins thereof. While these types of approaches are useful for identifying metastases, PET and other imaging techniques based on detection of γ-rays lack sufficient resolution to visualise the fine margins of tumours in vivo.

Compounds of the invention, in particular compounds of formula I (or of formula Ia), comprise the structure Y-F-Z, where Y comprises a targeting vector, Z comprises a radiolabel (such as a chelated radionucleotide), F comprises a fluorophore (such as a cyanine dye (Cy5 or Cy7) analogue) and each "-" represents a bond or a linker. The probe may target PSMA, in particular as expressed in tumour. The radiolabel may be detected via gamma-/beta-tracing/imaging and is useful for imaging in presurgical planning, intraoperative and postsurgical evaluation. The fluorophore may be detected by fluorescence imaging/tracing, an approach that provides a superior resolution and may be used to more clearly define the margins of tumours. This may be beneficial, for example during tumour excision surgery, as it may assist guiding removal of all diseased tissue, while preserving healthy tissue.

The specific structure of the compound may also be advantageous for imaging and other uses, in particular for compounds that target PSMA. Exemplary compounds of the disclosure that target PMSA may advantageously have relatively low uptake in background organs compared to existing PMSA targeting compounds. For example, compounds of formula I (or formula Ia) that have an asymmetric dye portion (e.g. asymmetric fluorophore F) may demonstrate enhanced utility as tracers. Without wishing to be bound by any theory, it is believed that these advantages may be due to alterations in the binding affinity (e.g. lower IC-50) as well as alterations in renal clearance and uptake in the salivary glands due to the structure of the compounds, which has the potential to provide reduced background and toxicity.

The probes (Y) typically target PSMA. For example, EuK and related probes provide a vector that targets the aspartate (S1 position) and glutamate (S1' position) binding sites of PSMA. PSMA also comprises an accessory hydrophobic pocket (Barinka et al., *J. Med. Chem.*, 2008, 51, 7737-43; the content of which is incorporated herein by reference in its entirety) and it is believed that hydrophobic substituents of the dye portion (fluorophore F) may bind into the accessory hydrophobic binding pocket. Thus changing the hydrophobic substituents of the dye portion may be used to tune receptor affinity. Charged substituents of the dye portion, such as sulfonate, may also interact with the accessory pocket. Thus changing the charged substituents of the dye portion may also be used to tune receptor affinity.

An aspect provides a method for imaging a tumour, comprising administering to a subject a compound of the invention or formulation of the invention, and after a predetermined time imaging the tumour. A related aspect provides use in imaging of a compound or formulation of the invention.

The compound of the invention may be a compound of formula I and/or a compound of formula Ia. The predetermined time may be a predetermined time prior to intraoperative imaging. In some instances, the imaging could be dynamic, in which case the predetermined time may be as low as 0 hours. The predetermined time, e.g. prior to intraoperative imaging may be at least 0 hours, at least 0.25 hours, at least 0.5 hours, or at least 1 hour. The predetermined time may be not more than 48 hours. For example, the 15 predetermined time may be not more than 24 hours. The predetermined time, e.g. prior to intraoperative imaging is at least about 0.5 and not more than about 48 hours. For example, the predetermined time may be at least about 1 (or about 2) and not more than about 36 hours; e.g. the predetermined time may be at least about 3 and not more than about 24 hours.

The compound (e.g. compound of formula I or compound of formula Ia) may comprise a chelated radiolabel and the imaging may comprise imaging of radioactive decay. The imaging of radioactive decay may comprise at least one of positron emission tomography (PET), single photon emission computed tomography (SPECT), scintigraphy, gamma-tracing/imaging, beta-tracing, intraoperative gamma-tracing/imaging, or intraoperative beta-tracing. The imaging may comprise positron emission spectroscopy (PET), single photon emission computed tomography (SPECT), scintigraphy, (intraoperative) gamma-tracing/imaging, or (intraoperative) beta-tracing. For example, the imaging may comprise PET or SPECT. The imaging may comprise PET. The imaging may comprise SPECT.

The imaging may comprise fluorescence imaging. The imaging may comprise fluorescence spectroscopy.

The imaging may comprise imaging of radioactive decay and fluorescence imaging. The imaging may comprise imaging of radioactive decay prior to fluorescence imaging. For example, the imaging of radioactive decay may be performed before surgery and the fluorescence imaging may be performed during surgery.

The method of imaging may further comprise administering to said subject at least one compound that blocks or reduces the uptake of the compound of the invention in an organ (or in multiple organs). This may reduce the background signal of the compound of the invention in the relevant organ(s). For example, the at least one compound may block or reduce the uptake of the compound of the invention in kidneys and/or salivary glands. Examples of such compounds include mannitol, 2-(phosphonomethyl) pentanedioic acid, monosodium glutamate, succinylated gelatin and albumin fragments. The at least one blocking compound may be co-administered with the compound of the invention (e.g. as a single dosage form), or the at least one blocking compound may be administered separately to the compound of the invention Compounds of the invention and formulations of the invention may also be used for the treatment of a disease, in particular cancer (e.g. prostate cancer and/or other cancers expressing PSMA; such as renal cancer, breast cancer, gliomas, colorectal adenocarcinoma, transitional cell carcinoma, pancreatic ductal adenocarcinoma, or gastric adenocarcinoma). Such compounds (or formulations comprising such compounds) may comprise a radiolabel as disclosed herein. For example, the radiolabel may be selected from a β-emitter (e.g. $^{90}$Y, $^{166}$Ho, $^{68}$Ga, $^{177}$Lu), and an α-emitter (e.g. $^{225}$Ac, $^{224}$Ra, $^{213}$Bi). The compounds provide hybrid tracers that may target PMSA and when said compounds comprise a radiolabel that is a β-emitter and/or an α-emitter, the compound may be useful in radiotherapy. In such therapeutic applications, the main role of the dye portion may be to provide favourable pharmacokinetics (e.g. by extending the circulation half-life of the compound, prolonging the time window for binding to PSMA).

An aspect provides a compound of the invention or formulation of the invention for use as a medicament. A related aspect a compound of the invention or formulation of the invention for use in the treatment of cancer. The cancer may be a cancer comprising cells that express PSMA. For example, the cancer may be prostrate cancer, renal cancer, breast cancer, gliomas, colorectal adenocarcinoma, transitional cell carcinoma, pancreatic ductal adenocarcinoma, or gastric adenocarcinoma; e.g. the cancer may be prostate cancer.

An aspect provides a method for the treatment of cancer, comprising administering a compound of the invention or formulation of the invention to a patient in need of treatment. The cancer may be a cancer comprising cells that express PSMA. For example, the cancer may be prostrate cancer, renal cancer, breast cancer, gliomas, colorectal adenocarcinoma, transitional cell carcinoma, pancreatic ductal adenocarcinoma, or gastric adenocarcinoma; e.g. the cancer may be prostate cancer.

The methods of treatment disclosed herein may further comprise administering at least one compound that blocks or reduces the uptake of the compound of the invention in an organ (or in multiple organs). This may reduce the background signal of the compound of the invention in the relevant organ(s). For example, the at least one compound may block or reduces the uptake of the compound of the invention in kidneys and/or salivary glands. Examples of such compounds include mannitol, 2-(phosphonomethyl) pentanedioic acid, monosodium glutamate, succinylated gelatin and albumin fragments. The at least one blocking compound may be co-administered with the compound of the invention (e.g. as a single dosage form), or the at least one blocking compound may be administered separately to the compound of the invention.

ADDITIONAL EMBODIMENTS

The invention and disclosure also includes the subject matter of the following numbered clauses:

1. A compound of formula I or Ia:

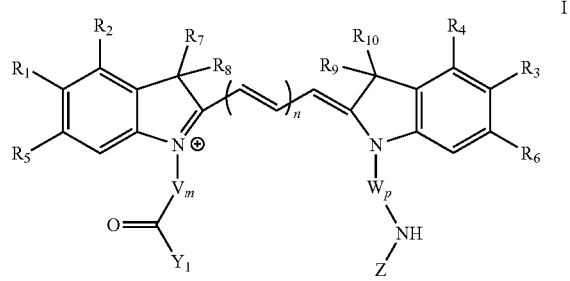

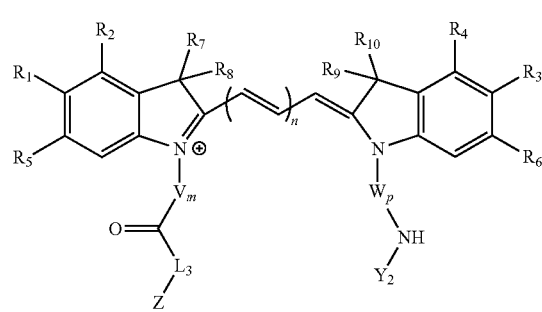

wherein:
$R_1$ is selected from sulfonate, carboxyl, phosphonate, amine, azide, and H and $R_2$ is selected from sulfonate, carboxyl, phosphonate, amine, azide, and H; or $R_1$ and $R_2$ together form an aryl that is optionally substituted with one to four groups (e.g. one or two groups) each independently selected from sulfonate, carboxyl, phosphonate, amine and azide;
$R_3$ is selected from sulfonate, carboxyl, phosphonate, amine, azide, and H and $R_4$ is selected from sulfonate, carboxyl, phosphonate, amine, azide, and H; or $R_3$ and $R_4$ together form an aryl that is optionally substituted with one to four groups (e.g. one or two groups) each independently selected from sulfonate, carboxyl, phosphonate, amine and azide;
each of $R_5$, $R_6$, $R_7$, $R_8$, $R_9$ and $R_{10}$ is independently selected from sulfonate, carboxyl, phosphonate, amine, azide, $CH_3$, $CH_2CH_3$ and H;
V is —$CH_2$— or —$CH_2CH_2O$—;
W is —$CH_2$— or —$CH_2CH_2O$—;
$Y_1$ is —EuK, —EuFA, —EuPG, -$L_1$-EuK, -$L_1$-EuFA, -$L_1$-EuPG or -$L_3$-EuE;
$Y_2$ is -$L_4$-EuK, -$L_4$-EuFA, -$L_4$-EuPG, -EuE, or -$L_2$-EuE;
Z is a chelating moiety;
$L_1$ is a linker of formula —NH—$R_{12}$—C(O)—, where $R_{12}$ is a bond, or a substituted or unsubstituted alkyl;
$L_2$ is a linker of formula —C(O)—$R_{13}$—NH—, where $R_{13}$ is a bond, or a substituted or unsubstituted alkyl;
$L_3$ is a linker of formula —NH—$R_{14}$—NH—, where $R_{14}$ is a substituted or unsubstituted alkyl;
$L_4$ is a linker of formula —C(O)—$R_{15}$—C(O)—, where $R_{15}$ is a substituted or unsubstituted alkyl;
n is 2 or 3;
m is 4-21; and
p is 3-21,
or a pharmaceutically acceptable salt thereof.
2. The compound of clause 1, wherein at least one of the substituents $R_1$, $R_2$, $R_5$, $R_7$, $R_8$ of the first indole moiety differs from at least one of the substituents $R_3$, $R_4$, $R_6$, $R_9$, $R_{10}$ of the second indole moiety, thereby providing an asymmetric dye portion.
3. The compound of clause 1 or clause 2, wherein $R_1$ is selected from sulfonate and H and $R_2$ is selected from sulfonate and H.
4. The compound of clause 1 or clause 2, wherein $R_1$ is sulfonate and $R_2$ is H.
5. The compound of clause 1 or clause 2, wherein $R_1$ and $R_2$ together form an optionally substituted aryl.
6. The compound of any preceding clause, wherein $R_3$ is selected from sulfonate and H and $R_4$ is selected from sulfonate and H.
7. The compound of any of clauses 1 to 4, wherein $R_3$ and $R_4$ together form an optionally substituted aryl.
8. The compound of any preceding clause, wherein $R_5$ is H and/or $R_6$ is H.
9. The compound of any preceding clause, wherein each of $R_7$, $R_8$, $R_9$ and $R_{10}$ are —$CH_3$ or —H; optionally wherein each of $R_7$, $R_8$, $R_9$ and $R_{10}$ are —$CH_3$.
10. The compound of any preceding clause, wherein V is —$CH_2$— and/or W is —$CH_2$—.
11. The compound of any preceding clause, wherein m is 4-12; optionally wherein m is 4, 5 or 6; further optionally wherein m is 5.
12. The compound of any preceding clause, wherein p is 3-12; optionally wherein p is 3, 4, or 5; further optionally wherein p is 4.
13. The compound of any preceding clause, wherein n is 2.
14. The compound of any preceding clause, wherein n is 3.
15. The compound of any preceding clause, wherein $Y_1$ is —EuK.
16. The compound of any preceding clause, wherein Z is a residue of a residue of bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]-hexadecan (DO2A), 1,4,7,10-tetraazacyclododecan-N,N',N'',N'''-tetraacetic acid (DOTA), 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphat) (DPDP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclo-tridecan-N,N',N'',N'''-tetraacetic acid (TRITA), triethylenetetraaminehexaacetic acid (TTHA), N,N'-bis[(6-carboxy-2-pyridyl)methyl]-4,13-diaza-18-crown-6 ($H_2$macropa), or 4-amino-4-{2-[(3-hydroxy-1,6-dimethyl-4-oxo-1,4-dihydro-pyridin-2-yl-methyl)-carbamoyl]-ethyl}heptanedioic acid bis-[(3-hydroxy-1,6-dimethyl-4-oxo-1,4-dihydro-pyridin-2-ylmethyl)-amide] (THP).
17. The compound of any preceding clause, wherein Z is -$MAS_3$, -$MAG_3$, -DOTA-GA, -DOTA, or -DTPA; optionally Z is -$MAS_3$.
18. The compound of any of clauses 1 to 17, wherein the compound is selected from:

39
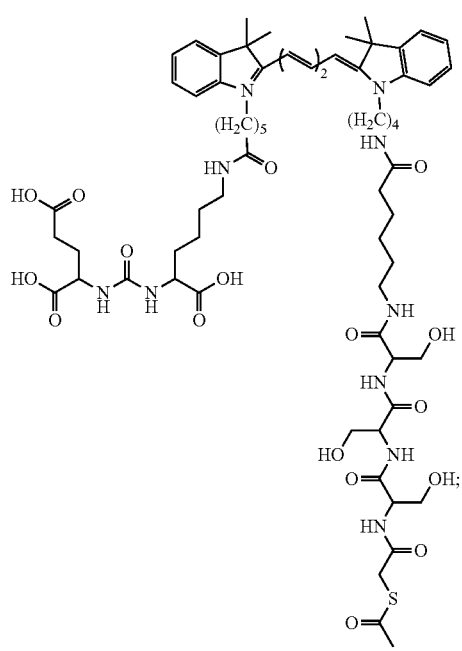
40
-continued
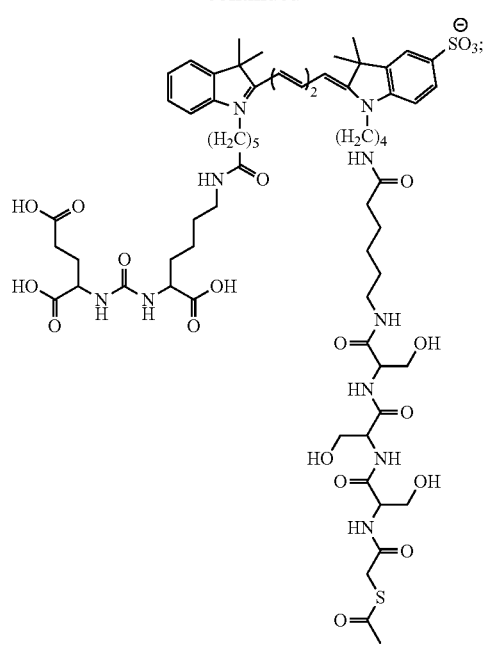
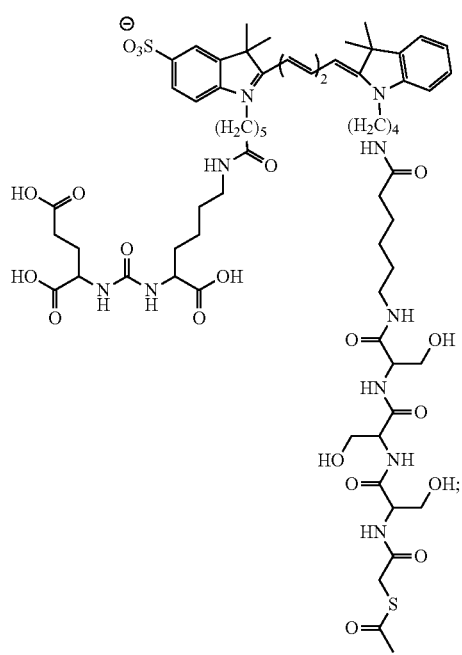
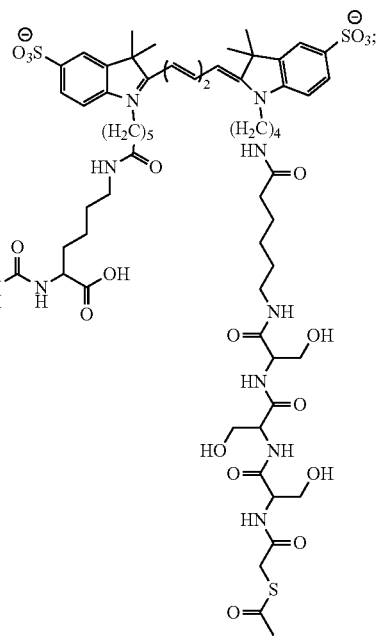

41
-continued
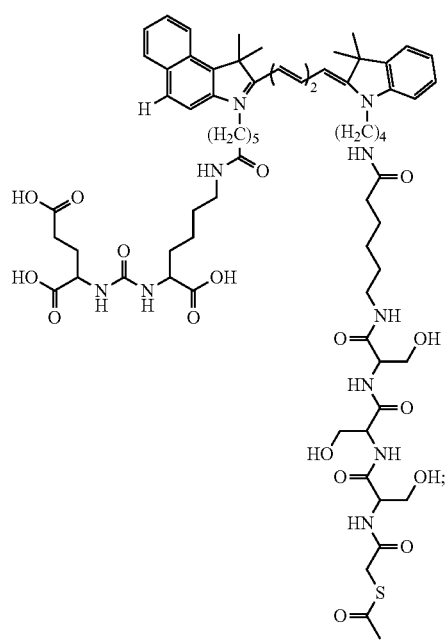
42
-continued
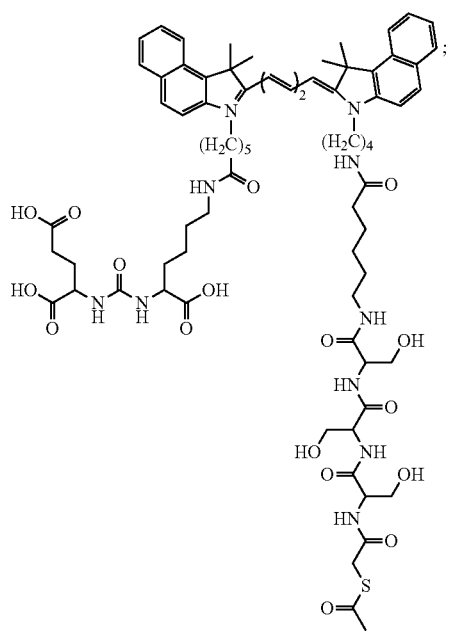
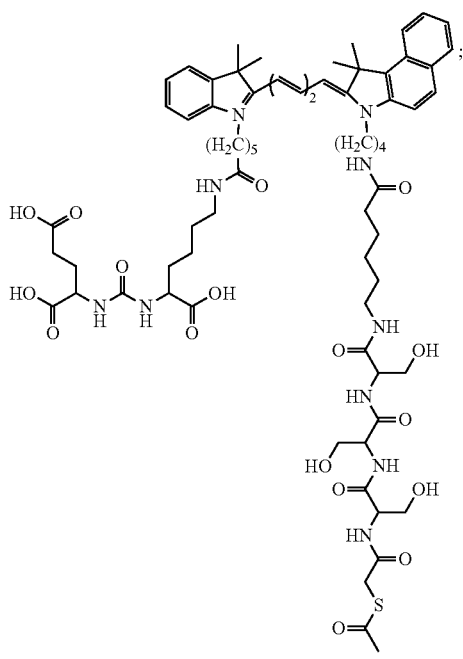
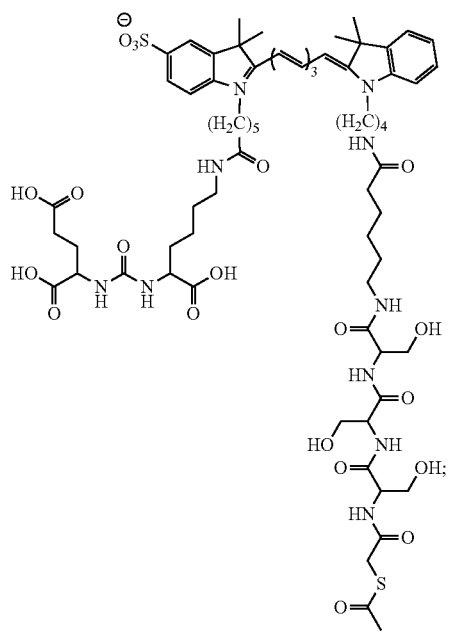

43
-continued
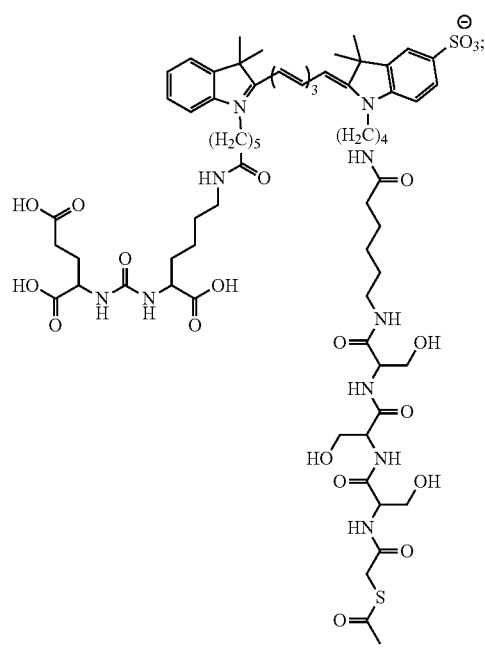
44
-continued
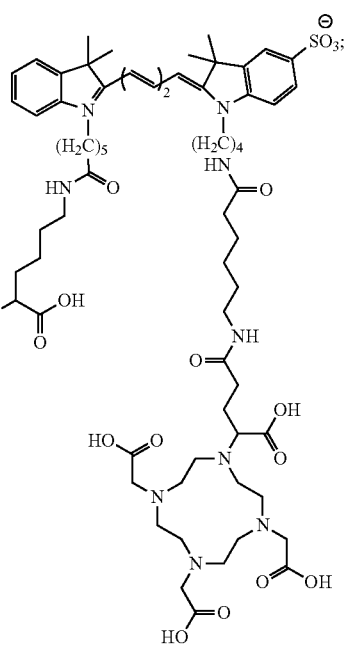
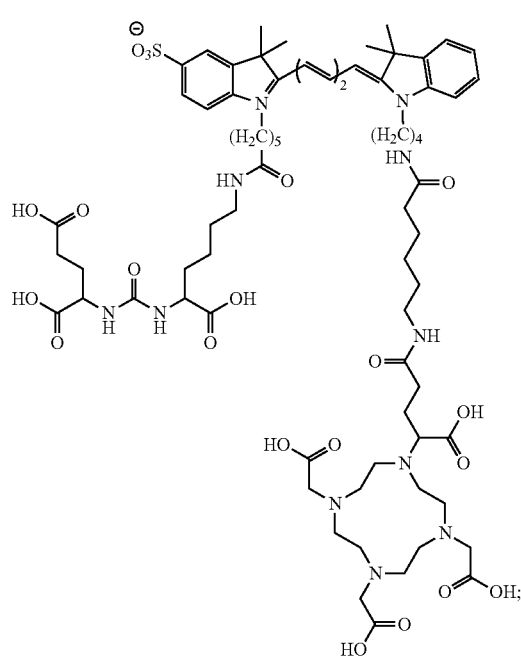
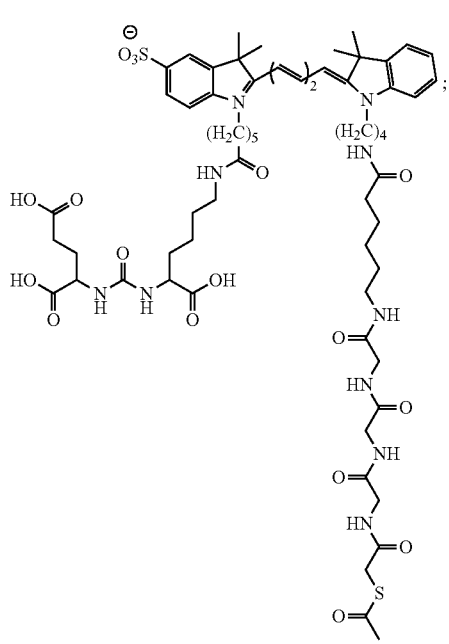

45
-continued
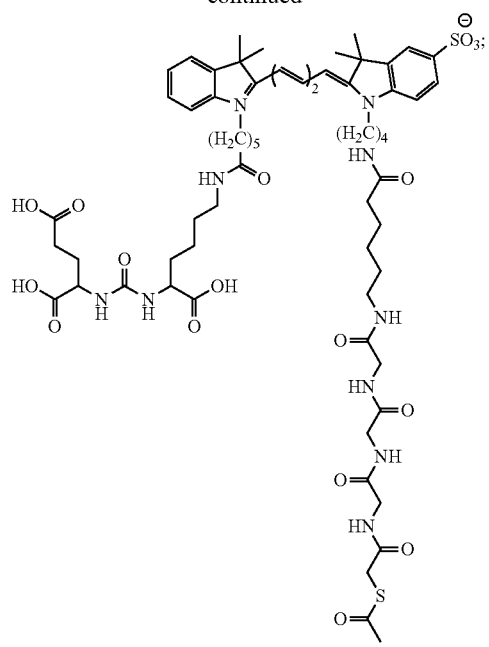
46
-continued
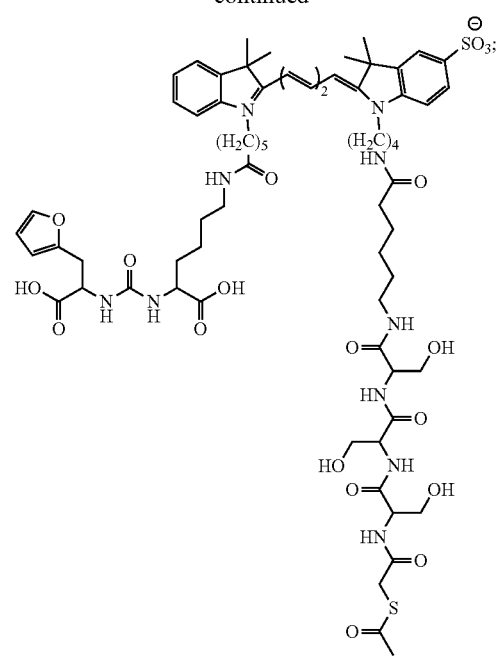
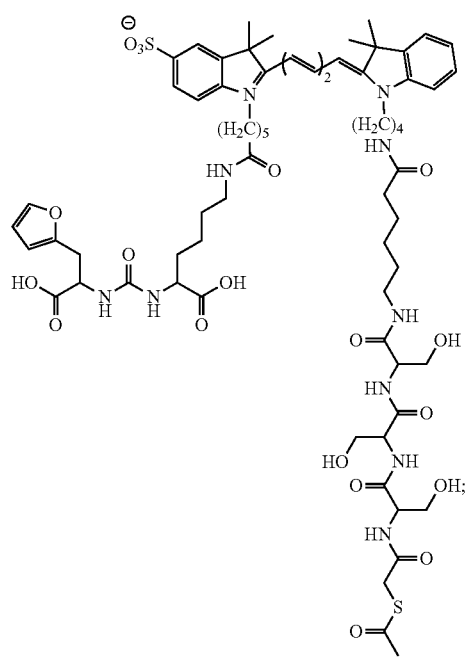
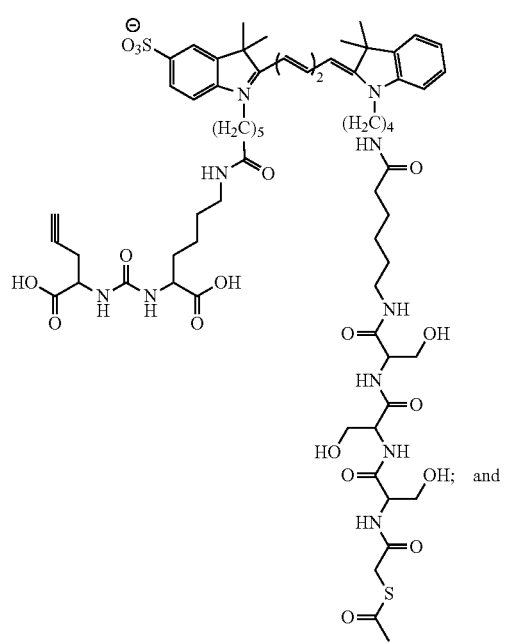
and

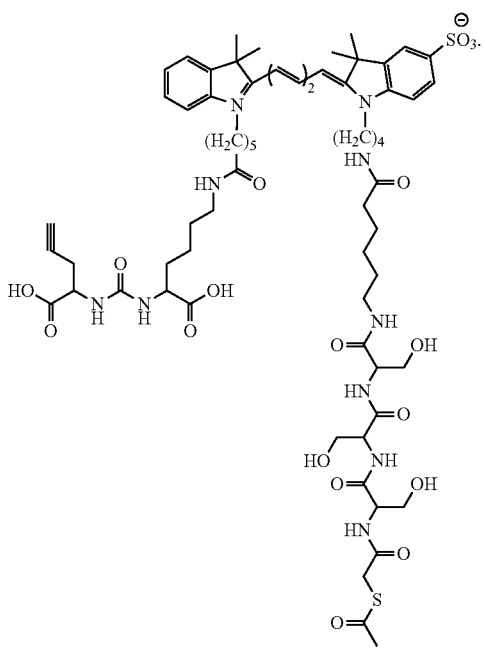

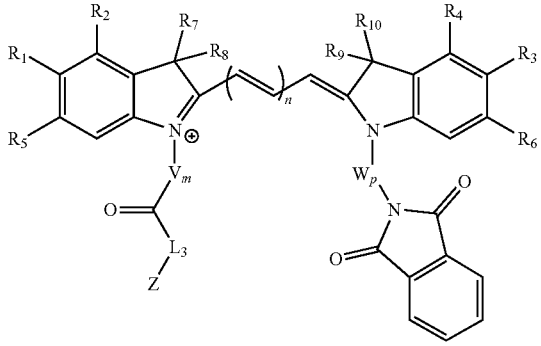

wherein:
$R_1, R_2, R_3, R_4, R_5, R_6, R_7, R_8, R_9, R_{10}, V, W, Z, L_3, m, n$ and p are as defined in any of claims 1 to 14, 16 or 17.

23. The compound of clause 22, further comprising a chelated radiolabel as defined in any of clauses 19 to 21.

24. A compound of formula III or formula IIa, or a pharmaceutically acceptable salt thereof:

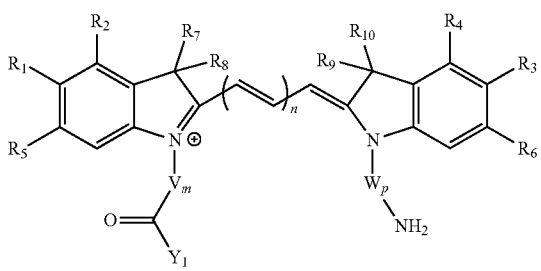

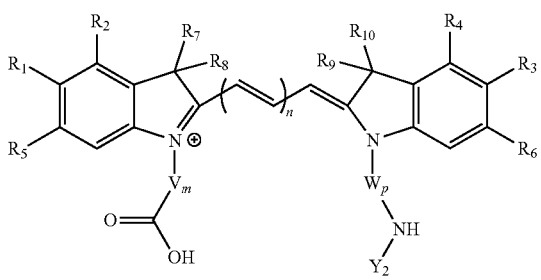

wherein:
$R_1, R_2, R_3, R_4, R_5, R_6, R_7, R_8, R_9, R_{10}, V, W, Y_1, Y_2, m, n$ and p are as defined in any of claims 1 to 15.

19. The compound of any proceeding clause, further comprising a chelated radiolabel, optionally selected from $^{44}$Sc, $^{47}$Sc, $^{51}$Cr, $^{52m}$Mn, $^{58}$CO, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F, such as $^{18}$F—[AlF]$^{2+}$. Exemplary radiolabels also include $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th, or a cationic molecule comprising $^{18}$F.

20. The compound of clause 19, wherein the chelated radiolabel is selected from a γ-emitter, a β-emitter, and an α-emitter, or a combination thereof.

21. The compound of clause 19 or clause 20, wherein the chelated radiolabel is selected from $^{68}$Ga, $^{177}$Lu and $^{99m}$Tc, or a combination thereof.

22. A compound of formula II or formula IIa, or a pharmaceutically acceptable salt thereof:

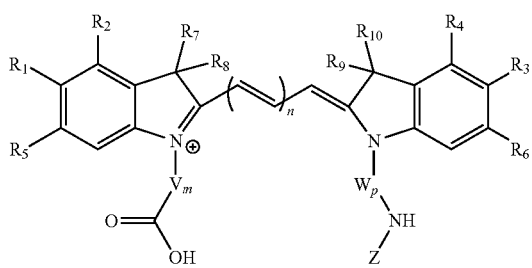

25. A formulation, comprising the compound of any of clauses 1 to 21 and optionally a pharmaceutically acceptable carrier.

26. A formulation of clause 25, further comprising at least one other anticancer compound.

27. A formulation of clause 25 or clause 25, further comprising a compound that influences in vivo kinetics the compound of any of clauses 1 to 21, optionally wherein said compound reduces kidney retention of the compound of any of clauses 1 to 21.

28. A method for imaging a tumour, comprising administering to a subject a compound of any of clauses 1 to 21 or formulation of any of clauses 25 to 27, and after a predetermined time imaging the tumour.
29. The method of clause 28, wherein the predetermined time is at least about 1 and not more than about 48 hours.
30. The method of clause 28 or clause 29, wherein the tumour is a prostate cancer tumour, renal tumour, breast cancer tumour, glioma, colorectal adenocarcinoma, transitional cell carcinoma, pancreatic ductal adenocarcinoma, or gastric adenocarcinoma; optionally wherein the tumour is a prostate cancer tumour.
31. The method of any of clauses 28 to 30, wherein the compound comprises a chelated radiolabel and the imaging comprises positron emission spectroscopy (PET), single photon emission computed tomography (SPECT), scintigraphy, (intraoperative)gamma-tracing/imaging, or (intraoperative)beta-tracing.
32. The method of clause 31, wherein the imaging comprises PET or SPECT.
33. The method of any of clauses 28 to 32, wherein the imaging comprises fluorescence imaging, optionally wherein the imaging comprises fluorescence spectroscopy.
34. A method for the treatment of cancer, comprising administering a compound of any of clauses 1 to 21 or formulation of any of clauses 25 to 27.
35. The method of clause 34, wherein the cancer is prostate cancer, renal cancer, breast cancer, gliomas, colorectal adenocarcinoma, transitional cell carcinoma, pancreatic ductal adenocarcinoma, or gastric adenocarcinoma, optionally wherein the cancer is prostate cancer.
36. Use in imaging of a compound of any of clauses 1 to 21, or a formulation of any of clauses 25 to 27.
37. A compound of any of clauses 1 to 21, or a formulation of any of clauses 25 to 27, for use as a medicament.
38. A compound of any of clauses 1 to 21, or a formulation of any of clauses 25 to 27, for use in the treatment of cancer.
39. The compound or formulation of clause 38, wherein the cancer is prostate cancer, renal cancer, breast cancer, gliomas, colorectal adenocarcinoma, transitional cell carcinoma, pancreatic ductal adenocarcinoma, or gastric adenocarcinoma, optionally wherein the cancer is prostate cancer.

EXAMPLES

Example 1: Synthesis of Exemplary Compounds

Compounds were synthesised in accordance with the reaction scheme illustrated in FIG. 1. In this reaction scheme, Phthalimide-containing cyanine fluorophores in 1) the amine liberation resulted in 2) Amine-containing cyanine fluorophores. Conjugation with EuK leads to 3) fluorescence-only targeting precursors. Subsequent addition of an MAS3-NHS chelate resulted in 4) hybrid tracer precursors that contained both a fluorescent and a chelate for radiolabelling. 5) Deprotection of the EuK moiety leads to activation of the targeting EuK. a-g provide an overview of the different indole substituents for the dyes used within the matrix. While this synthesis is demonstrated for the probe EuK and chelate $MAS_3$, as the skilled person will appreciate, the synthesis may be readily adapted to other probes (e.g. EuAF or EuPG) and other chelates (e.g. $MAG_3$, DOTA-GA, DOTA, DTPA).

Using standard solid-phase synthetic strategies, asymmetrical Cy5 dyes were synthesised with slight structural alterations (1a-1g; hereafter named Phth-Cy5-COOH (1a); Phth(SO3)-Cy5-COOH (1b); Phth-Cy5-(SO3)COOH (1c); Phth(SO3)-Cy5-(SO3)COOH (1d); Phth(Ar)-Cy5-COOH (1e); Phth-Cy5-(Ar)COOH (1f); Phth(Ar)-Cy5-(Ar)COOH (1g)) to investigate the characteristics of each cyanine fluorophore. Hybrid tracer analogues were formed from these dyes. In order to do so, several synthetic steps were carried out: conversion the phthalimide moiety to a free amine, a slightly adapted version of the Gabriel synthesis is utilised on these dyes yielding 2a-2g. Consequently, the MAS3 chelate (including a six-carbon spacer with activated carboxylic acid) is coupled using NHS-activation to form a simple amide bond yielding 3a-3g. Consecutive addition of the KuE(tBu)3 targeting moiety to the carboxylic acid group utilising PyBOP yields compounds 4a-4g. To finalise the hybrid tracer, three tert-butyl esters on the KuE moiety were removed by stirring in TFA:$H_2O$ 95:5, yielding tracers 5a-5g and 5a-5g (hereafter named EuK-Cy5-MAS3 (5a); EuK—(SO3)Cy5-MAS3 (5b); EuK-Cy5-(SO3)MAS3 (5c); EuK(SO3)-Cy5-(SO3)MAS3 (5d); EuK(Ar)-Cy5-MAS3 (5e); EuK-Cy5-(Ar)MAS3 (5f); EuK(Ar)-Cy5-(Ar)MAS3) (5g) (Scheme 1). The above resulted in a matrix of hybrid tracers with slight structural alterations to tune chemical, photophysical, in vitro and in vivo characteristics.

Example 2: Additional Synthesis

EuK(Z)-(OtBu)$_3$

Synthesized as inspired by Khan et al. *J Medl Chem* 42 (6), 951-956, the content of which is incorporated herein by reference in its entirety. H-Glu(OtBu)-OtBu·HCl (1.0 g, 3.38 mmol), 4-nitrophenyl chloroformate (682 mg, 3.38 mmol) and triethylamine (943 µL, 6.76 mmol) were dissolved in dry DCM (20 ml). The mixture was refluxed under a $N_2$ atmosphere for 25 minutes followed by stirring at r.t. for 60 minutes. A white precipitate was formed which disappeared when H-Lys(Z)-OtBu·HCl (1387 mg, 3.72 mmol) and triethylamine (943 µL, 6.76 mmol) were added. The solution turned yellow and was refluxed for 10 minutes before stirring at r.t. for 90 minutes. TLC showed full conversion of the starting material and thus the mixture was concentrated in vacuo to a small volume. Ethyl acetate (80 ml) was added and the suspension was stirred for 16 hours at r.t. after which it was filtered using a glass filter (P3). The white precipitate was washed with ethyl acetate, the filtrate was combined with the supernatant and concentrated in vacuo to obtain a yellow oil. Column chromatography was performed using a gradient of ethyl acetate/hexane 1:5 to 1:2 over 6 column volumes, followed by 100% ethyl acetate for 1 column volume. The correct fractions were pooled and lyophilization yielded the title compound as a slightly yellow oil. MALDI-TOF m/z [M+Na]$^+$ calcd. 644.8, found 644.6.

EuK(NH2)-(OtBu)$_3$

Synthesized as inspired Makowski et al., *Liebigs Ann. Chem.*, 1985, 1451-1464, the content of which is incorporated herein by reference in its entirety. EuK(Z)-(OtBu)$_3$ (1.9 g, 3.06 mmol), ammonium formate (385 mg, 6.11 mmol) and Pd/C (19 mg) were refluxed (100° C.) in absolute ethanol (40 ml) under a $N_2$ atmosphere for 120 minutes. The reaction mixture was allowed to cool down to r.t. before filtering the suspension over celite. The celite was subsequently rinsed with absolute ethanol (50 ml). The solvent was removed in vacuo resulting in a yellow oil. Purification by HPLC yielded the title compound in quantitative yield as a yellowish oil. MALDI-TOF m/z [M+H]$^+$ calcd. 487.6, found 488.1 [M+Na]$^+$ calcd. 510.6, found 510.2.

DOTAGA-Ahx-COOH

DOTA-GA(OtBu)$_4$ (50 mg, 71.34 µmol) was dissolved in DMSO (2 mL) after which HSPyU (26.4 mg, 64.20.54 µmol) and DiPEA (62 µL, 356.38 µmol) were added and the solution was stirred at room temperature for 15 minutes. Subsequently, a suspension of 6-Aminohexanoic acid (9.4 mg, 71.34 µmol) and additional DiPEA (12.4 µL, 71.34 µmol) were added and the solution was stirred for 105 minutes. Acetonitrile/H$_2$O 9:11 were added and the mixture was purified by preparative HPLC. After pooling the correct fractions, lyophilizing yielded a white solid. MALDI-TOF m/z [M+H]$^+$ calcd. 815.1, found 814.3.

MAS3-Ahx-COOH

Synthesised according to standard SPPS, starting with Fmoc-Ahx-WANG resin (1.0 g). After subsequent deprotection- and coupling steps, the product was cleaved off of the resin by gently shaking the resin in 100% TFA for 180 min at r.t. The filtrate was collected and the solvent was evaporated. The crude compound was purified by HPLC and lyophilised. MALDI-TOF [M+H]$^+$ calcd. 508.5, found 508.9.

MAG3-Ahx-COOH

Synthesised according to standard SPPS, starting with Fmoc-Ahx-WANG resin (1.48 g). After subsequent deprotection- and coupling steps, the product was cleaved off of the resin by gently shaking the resin in 100% TFA for 120 min at r.t. The filtrate was collected and the solvent was evaporated. The crude compound was used without further purification. MALDI-TOF [M+H]$^+$ calcd. 418.5, found 418.5.

Merrifield Resin

As performed by Lopalco et al. Org Biomol Chem., 2009, 7(5), 856-9, Chloromethyl polystyrene resin (8.3 g, 15.0 mmol), N-Boc-aminophenol (9.4 g, 45.0 mmol), tetrabutylammonium iodide (1.7 g, 4.5 mmol) and CSCO$_3$ (14.7, 45.0 mmol) were dissolved in acetone and refluxed at 70° C. overnight under N$_2$ atmosphere. Resin was then washed extensively with DMF (100 mL), H$_2$O (100 mL), DMF (100 mL), DCM (100 mL) and Et$_2$O (100 mL) and dried in vacuo. 4-(4-nitrobenzyl)pyridine test was used to determine reaction completion.

Indole-COOH 2,3,3-trimethylindolenine (5.3 g, 33 mmol) and 6-bromohexanoic acid (5.9 g, 30 mmol) were heated at 95-120° C. in 75 mL 1,2-dichlorobenzene for 72 h. Et$_2$O (75 mL) was added and the mixture was filtered. The residue was washed with Et$_2$O and dried in vacuo, by which the title compound was obtained. The crude product was used directly in the next reaction without any further purification.

Sulfoindole-COOH 2,3,3-trimethyl-3H-indole-5-sulfonate potassium salt (6.9 g, 25 mmol) and 6-bromohexanoic acid (7.3 g, 37.5 mmol) in 1,2-dichlorobenzene (40 mL) was stirred at 95° C. for 72 h. The solid compound formed was collected and crushed. After washing with Et$_2$O, the crude product was obtained and directly used in the next reaction.

Indole-C$_4$Phth 2,3,3-trimethylindolenine (1.9 mL, 11.8 mmol) and 1-(4-bromobutyl)pyrrolidine-2,5-dione (10.0 g, 35.4 mmol) were heated at 90° C. in sulfolane (20.0 mL) under N$_2$ atmosphere for 48 hours. The reaction mixture was precipitated in EtOAc and the suspension was filtered. The residue was washed with Et2O and EtOAc twice. In vacuo drying resulted in the title compound as a slight yellow solid. This product was used in the next reaction without any further purification.

Sulfoindole-Phth

Sulfoindole (BB3) (6.925 g, 25.0 mmol) and 1-(4-bromobutyl)pyrrolidine-2,5-dione (17.6 g, 75.0 mmol) were heated at 90° C. in sulfolane (40.0 mL) under N$_2$ atmosphere for 24 hours. The reaction mixture was precipitated by the addition of MeOH (5 mL) after which the suspension was filtered. The residue was washed with Et2O and EtOAc twice. In vacuo drying resulted in the title compound as a pink solid which was used without any further purification.

Phth(SO$_3$)-Cy7-COOH

Indole-COOH (1771 mg, 5.00 mmol) and glutaconaldehydedianil HCl (1566 mg, 5.50 mmol) were dissolved in a mixture of Ac$_2$O/AcOH (1:1; 50 mL) and stirred at 60° C. overnight. The following morning, the mixture was heated to 120° C. for 1 h. Subsequently, the mixture was allowed to cool down to r.t. After cooling, the prepared hemicyanine precipitated in ice cold MTBE/Hexane (1:1; 1000 mL). The precipitate was washed twice with MTBE/Hexane. Meanwhile, the Merrifield resin (1590 mg, 2.65 mmol) was prepared by adding a TFA/DCM mixture (20:80; 40 mL) and bubbling through N$_2$ for 1 h. The resin was hereafter washed with DCM (40 mL) thrice before adding a DiPEA/DCM (25:75; 40 mL) mixture. N$_2$ was bubbled through for 20 min. prior to washing with DCM (40 mL) thrice. The precipitated hemicyanine was then dissolved in DMF/DCM (1:1; 40 mL) before adding to the resin. N$_2$ was bubbled through for 1 h before washing the resin with various DMF/DCM compositions. Sulfoindole-Phth (550 mg, 1.25 mmol) was dissolved in pyridine/Ac$_2$O (3:1; 40 mL) and added to the resin and the mixture was shaken overnight. The liquids were obtained and the resin was washed with various DMF/DCM mixtures. The obtained dye-containing mixture was concentrated in vacuo before purifying by DCVC (EtOAc/MeOH 0-60%). Relevant fractions were combined, concentrated and further purification by means of HPLC was employed. This purification obtained the title compound as a green solid. MALDI-TOF m/z [M+H]$^+$ calcd. 777.0 found 776.7.

Phth(SO$_3$)-Cy7-EuK(OtBu)$_3$

Phth(SO$_3$)-Cy7-COOH (10.0 mg, 12.89 µmol) was dissolved in DMF (500 µL) before adding DiPEA (38.31 mg, 296.41 µmol) and PyBOP (60.36 mg, 115.99 µmol). After stirring for 2 minutes, EuK(OtBu)$_3$ (56.56 mg, 115.99 µmol), dissolved in 500 µL DMF, was added. The mixture was allowed to stir for 60 minutes at r.t. under a N$_2$ atmosphere. Hereafter, H$_2$O was added and the crude was purified by HPLC. Relevant fractions were combined and the obtained mixture was concentrated in vacuo, yielding the title compound as a green solid. MALDI-TOF m/z [M+H]$^+$ calcd. 1246.6 found 1246.5.

Amine(SO$_3$)-Cy7-EuK(OtBu)$_3$

Phth(SO$_3$)-Cy7-EuK(OtBu)$_3$ (7.0 mg, 5.62 µmol) was dissolved in methylamine (33 wt % in EtOH; 10 mL) and stirred at r.t. for 1.5 h. After this time, remaining methylamine and EtOH were removed in vacuo. A mixture of H$_2$O/MeCN was added before purifying the crude by means of HPLC. Relevant fractions were combined and concentrated in vacuo, yielding the title compound as a green solid. MALDI-TOF m/z [M+H]$^+$ calcd. 1116.6 found 1116.3.

MAS3(SO$_3$)-Cy7-EuK(OtBu)$_3$

MAS3-Ahx-COOH (3.14 mg, 6.18 µmol) was dissolved in DMSO (500 µL) before adding DiPEA (7.26 mg, 56.20 µmol) and PyBOP (14.6 mg, 28.10 µmol). After stirring for 5 minutes, Amine(SO$_3$)-Cy7-EuK(OtBu)$_3$ (6.27 mg, 5.62 µmol), dissolved in DMSO (500 µL) was added to the mixture. The resulting reaction mixture was stirred at r.t. for 1 h before adding H$_2$O and purifying by means of HPLC. Relevant fractions were combined and concentrated in vacuo, yielding the title compound as a green solid. MALDI-TOF m/z [M+H]$^+$ calcd. 1607.0 found 1606.8.

MAS3(SO$_3$)-Cy7-EuK

MAS3(SO$_3$)-Cy7-EuK(OtBu)$_3$ (2.0 mg, 1.24 µmol) was dissolved in TFA/H$_2$O (95:5; 3.0 mL) and stirred at r.t. for 1 h. Hereafter, remaining TFA and H$_2$O were removed in vacuo and the crude was purified by means of HPLC. This led to the acquiring of the title compound as a green solid. MALDI-TOF m/z [M+H]$^+$ calcd. 1438.7 found 1438.6.

Phth-Cy7-(SO$_3$)COOH

Sulfoindole-COOH (2166.69 mg, 5.00 mmol) and glutaconaldehydedianil HCl (1566 mg, 5.50 mmol) were dissolved in a mixture of Ac$_2$O/AcOH (1:1; 50 mL) and stirred at 60° C. overnight. The following morning, the mixture was heated to 120° C. for 1 h. Subsequently, the mixture was allowed to cool down to r.t. After cooling, the prepared hemicyanine was precipitated in Et2O (1000 mL). The precipitate was washed twice with Et2O (300 mL). Meanwhile, the Merrifield resin (1590 mg, 2.65 mmol) was prepared by adding a TFA/DCM mixture (20:80; 40 mL) and bubbling through N$_2$ for 1 h. The resin was hereafter washed with DCM (40 mL) thrice before adding a DiPEA/DCM (25:75; 40 mL) mixture. N$_2$ was bubbled through for 20 min. prior to washing with DCM (40 mL) thrice. The precipitated hemicyanine was then dissolved in DMF/DCM (1:1; 40 mL) before adding to the resin. N$_2$ was bubbled through for 1 h before washing the resin with various DMF/DCM compositions. Indole-Phth (451.83 mg, 1.25 mmol) was dissolved in pyridine/Ac$_2$O (3:1; 40 mL) and added to the resin and the mixture was shaken overnight. The liquids were obtained and the resin was washed with various DMF/DCM mixtures. The obtained dye-containing mixture was concentrated in vacuo before precipitation in Et2O (400 mL) and washing with Et2O (200 mL) twice. Solvents were then removed in vacuo and purified by means of HPLC. This purification obtained the title compound as a green solid. MALDI-TOF m/z [M+H]$^+$ calcd. 777.0 found 776.6.

Phth-Cy7-(SO$_3$)EuK(OtBu)$_3$

Phth-Cy7-(SO$_3$)COOH (10.0 mg, 12.89 µmol) was dissolved in DMF (500 µL) before adding DiPEA (38.31 mg, 296.41 µmol) and PyBOP (60.36 mg, 115.99 µmol). After stirring for 2 minutes, EuK(OtBu)$_3$ (56.56 mg, 115.99 µmol), dissolved in 500 µL DMF, was added. The mixture was allowed to stir for 60 minutes at r.t. under a N$_2$ atmosphere. Hereafter, H$_2$O was added and the crude was purified by HPLC. Relevant fractions were combined and the obtained mixture was concentrated in vacuo, yielding the title compound as a green solid. MALDI-TOF m/z [M+H]$^+$ calcd. 1246.6 found 1246.5.

Amine-Cy7-(SO$_3$)EuK(OtBu)$_3$

Phth-Cy7-(SO$_3$)EuK(OtBu)$_3$ (15.8 mg, 12.68 µmol) was dissolved in methylamine (33 wt % in EtOH; 10 mL) and stirred at r.t. for 2 h. After this time, remaining methylamine and EtOH were removed in vacuo. A mixture of H$_2$O/MeCN was added before purifying the crude by means of HPLC. Relevant fractions were combined and concentrated in vacuo, yielding the title compound as a green solid. MALDI-TOF m/z [M+H]$^+$ calcd. 1116.5 found 1116.3.

MAS3-Cy7-(SO$_3$)EuK(OtBu)$_3$

MAS3-Ahx-COOH (7.77 mg, 15.28 µmol) was dissolved in DMSO (100 µL) before adding DiPEA (17.96 mg, 138.95 µmol) and PyBOP (36.17 mg, 69.48 µmol). After stirring for 5 minutes, Amine-Cy7-(SO$_3$)EuK(OtBu)$_3$ (15.5 mg, 13.90 µmol), dissolved in DMSO (900 µL) was added to the mixture. The resulting reaction mixture was stirred at r.t. for 75 min. before adding H$_2$O and purifying by means of HPLC. Relevant fractions were combined and concentrated in vacuo, yielding the title compound as a green solid. MALDI-TOF m/z [M+H]$^+$ calcd. 1607.0 found 1606.9.

MAS3-Cy7-(SO$_3$)EuK

MAS3-Cy7-(SO$_3$)EuK(OtBu)$_3$ (22.3 mg, 13.90 µmol) was dissolved in TFA/H$_2$O (95:5; 3.0 mL) and stirred at r.t. for 1 h. Hereafter, remaining TFA and H$_2$O were removed in vacuo and the crude was purified by means of HPLC. This led to the acquiring of the title compound as a green solid. MALDI-TOF m/z [M+H]$^+$ calcd. 1438.7 found 1438.6.

Phth(SO$_3$)-Cy5-COOH

In short, indole-COOH (1.1 g, 4.0 mmol) and malonaldehyde dianilide hydrochloride (1.2 g, 4.4 mmol) were dissolved in AcOH/Ac$_2$OH (1:1, 30.0 mL) and left to stir at 60-120° C. under N$_2$ atmosphere for 12 hours. Crude product was dissolved in DMF:DCM (1:1, 70.0 mL). Merrifield resin (1.2 g, 2.0 mmol) was swelled in DCM for 5 minutes and was then left to bubble in 20% TFA in DCM (50.0 mL) for one hour to deprotect the amine of the resin and in 20% DiPEA in DCM (50.0 mL) for 15 minutes to remove excess TFA. Sulfoindole-Phth (440.0 mg, 1.0 mmol) was dissolved in pyridine/Ac$_2$O (3:1, 40.0 mL). The dye was precipitated from the mixture in diethyl ether and purified by column chromatography (DCM:MeOH, 20-100% MeOH, 8 CVs). After pooling the correct fractions, the solvent removed in vacuo and the remaining solid was further purified by preparative reversed-phase HPLC, the title compound as a blue solid. m/z [M+H]$^+$ calcd. 750.93, found 750.60.

Phth(SO$_3$)-Cy5-EuK(OtBu)$_3$

Phth(SO$_3$)-Cy5-COOH (3.0 mg, 4.00 µmol), EuK (NH$_2$)—(OtBu)$_3$ (23.4 mg in 249.2 µL in MeOH, 48 µmol), PyBOP (47.8 mg, 92.00 µmol) and DiPEA (16.0 µL, 122.67 µmol) were stirred in DMF (800 µL) for 90 minutes at r.t. after which the mixture was kept overnight at −21° C. The mixture was purified using HPLC. MALDI-TOF m/z [M+H]$^+$ calcd. 1220.6, found 1219.6.

Amine(SO$_3$)-Cy5-EuK(OtBu)$_3$

Phth(SO$_3$)-Cy5-CONH.EuK(OtBu)$_3$ (10 mg,) was dissolved in methylamine (33 wt % in EtOH; 10 mL) and stirred at r.t. for 2 h. After this time, remaining methylamine and EtOH were removed in vacuo. A mixture of H$_2$O/MeCN was added before purifying the crude by means of HPLC. Relevant fractions were combined and concentrated in vacuo, yielding the title compound as a blue solid. MALDI-TOF m/z [M+H]$^+$ calcd. 1090.5 found 1090.2.

Phth-Cy5-(SO$_3$)COOH

Sulfoindole-COOH (1.1 g, 2.4 mmol) and malonaldehyde dianilide hydrochloride (678.0 mg, 2.6 mmol) were dissolved in AcOH/Ac$_2$OH (1:1, 15.0 mL) and left to stir at 60-120° C. under nitrogen atmosphere for 12 hours. Crude product was dissolved in DMF (70.0 mL). Merrifield resin (720.0 mg, 1.2 mmol) was swelled in DCM for 5 minutes and was then left to bubble in DCM (20% TFA; 25.0 mL) for 1 h and in DCM (20% DiPEA; 25.0 mL) for 15 minutes. Indole-Phth (264.0 mg, 0.6 mmol) was dissolved in pyridine/Ac$_2$O (3:1, 20.0 mL). The dye was precipitated from the mixture in diethyl ether and purified by DCVC (EtOAc: MeOH, 0-100% MeOH, 25 fractions, 100.0 mL each). After pooling the correct fractions, the solvent was removed in vacuo and the remaining solid was further purified by preparative reversed-phase HPLC, yielding the title compound as a blue solid. m/z [M+H]$^+$ calcd. 750.93, found 750.78.

Phth-Cy5-(SO$_3$)EuK(OtBu)$_3$

Phth-Cy5-(SO$_3$)COOH (4.0 mg, 5.33 µmol), EuK(NH$_2$)—(OtBu)$_3$ (23.4 mg in 249.2 µL in MeOH, 48 µmol), PyBOP (25.0 mg, 48 µmol) and DiPEA (21.3 µL, 122.67 µmol) were stirred in DMF (800 µL) for 90 minutes at r.t. after which the mixture was kept overnight at −21° C. The mixture was purified using HPLC. MALDI-TOF m/z [M+H]$^+$ calcd. 1220.6, found 1219.6.

Amine-Cy5-(SO$_3$)EuK(OtBu)$_3$

Phth-Cy5-(SO$_3$)CONH.EuK(OtBu)$_3$ (6 mg, 4.92 µmol) was dissolved in methylamine (33 wt % in EtOH; 10 mL) and stirred at r.t. for 2 h. After this time, remaining methylamine and EtOH were removed in vacuo. A mixture of H$_2$O/MeCN was added before purifying the crude by means of HPLC. Relevant fractions were combined and concentrated in vacuo, yielding the title compound as a blue solid. MALDI-TOF m/z [M+H]$^+$ calcd. 1089.4, found 1089.6.

DOTAGA(OtBu)$_4$(SO$_3$)-Cy5-EuK(OtBu)$_3$

Amine(SO$_3$)-Cy5-EuK(OtBu)$_3$ (1.7 mg, 1.56 µmol) was dissolved in DMSO (500 uL). PyBOP (1.6 mg, 3.12 µmol, 100 µg/µL stock in DMSO) was added to DOTAGA(OtBu)$_4$-Ahx-COOH (1.8 mg, 2.19 µmol), supplemented with DMSO to 100 µL and added to the Amine(SO$_3$)-Cy5-EuK(OtBu)$_3$ solution. Then DiPEA (2.7 µL 15.61 µmol) was added and this mixture was stirred at r.t. for 30 minutes. The mixture was diluted with CH$_3$CN and H$_2$O (0.1% TFA v/v) and purified by HPLC. MALDI-TOF m/z [M+H]$^+$ calcd. 1885.5, found 1885.2.

DOTAGA(SO$_3$)-Cy5-EuK

DOTAGA(OtBu)$_4$(SO$_3$)-Cy5-EuK(OtBu)$_3$ was dissolved in TFA/TIPS/H$_2$O 95/2.5/2.5 (5 mL). After 2 h of stirring the solvent was evaporated and the residue was purified by HPLC. MALDI-TOF m/z [M+H]$^+$ calcd. 1492.8 found 1492.7.

DOTAGA(OtBu)$_4$-Cy5-(SO$_3$)EuK(OtBu)$_3$

Amine-Cy5-(SO$_3$)EuK(OtBu)$_3$ (2.4 mg, 2.20 µmol) was dissolved in DMSO (500 uL). PyBOP (2.3 mg, 4.41 µmol, 100 µg/µL stock in DMSO) was added to DOTAGA(OtBu)$_4$-Ahx-COOH (2.5 mg, 3.09 µmol), supplemented with DMSO to 100 µL and added to the Amine-Cy5-(SO$_3$)—EuK(OtBu)$_3$ solution. Then DiPEA (3.9 µL 22.04 µmol) was added and this mixture was stirred at r.t. for 30 minutes. The mixture was diluted with CH$_3$CN and H$_2$O (0.1% TFA v/v) and purified by HPLC. MALDI-TOF m/z [M+H]$^+$ calcd. 1885.5, found 1885.2.

DOTAGA-Cy5-(SO$_3$)EuK

DOTAGA(OtBu)$_4$(SO$_3$)-Cy5-EuK(OtBu)$_3$ was dissolved in TFA/TIPS/H$_2$O 95/2.5/2.5 (5 mL). After 2 h of stirring the solvent was evaporated and the residue was purified by HPLC. MALDI-TOF m/z [M+H]$^+$ calcd. 1492.8 found 1492.7.

MAG3(SO$_3$)-Cy5-EuK(OtBu)$_3$

Amine(SO$_3$)-Cy5-EuK(OtBu)$_3$ (10 mg, 9.18 µmol), MAG3-Ahx-COOH (15 mg, 36.73 µmol), PyBOP (19 mg, 36.73 µmol) and DiPEA (16 µL, 91.83) were dissolved in DMF (1 mL). The mixture was stirred at r.t. for 30 min after which it was kept overnight at −21° C. The crude was purified using HPLC, after which the correct fractions were pooled and lyphilized yielding a blue solid. MALDI-TOF m/z [M+H]$^+$ calcd. 1489.9, found 1489.8.

MAG3(SO$_3$)-Cy5-EuK

MAG3(SO$_3$)-Cy5-EuK(OtBu)$_3$ was dissolved in TFA/H$_2$O (95:5; 2.0 mL) and stirred at r.t. for 1 h. Hereafter, remaining TFA and H$_2$O were removed and the crude was purified by means of HPLC. This led to the acquiring of the title compound as a blue solid. MALDI-TOF m/z [M+H]$^+$ calcd. 1321.6, found 1321.6.

MAG3-Cy5-(SO$_3$)EuK(OtBu)$_3$

Amine-Cy5-(SO$_3$)EuK(OtBu)$_3$ (1.4 mg, 1.24 µmol), MAG3-Ahx-COOH (2.1 mg, 4.96 µmol), PyBOP (2.6 mg, 4.96 µmol) and DiPEA (2.2 µL, 12.40 µmol) were dissolved in DMF (250 µL) and the mixture was stirred at r.t. After 60 minutes the product was found and the reaction mixture was stored at −21° C. MALDI-TOF m/z [M+H]$^+$ calcd. 1489.9, found 1489.8.

MAG3-Cy5-(SO$_3$)EuK

MAG3-Cy5-(SO$_3$)EuK(OtBu)$_3$ was dissolved in TFA/H$_2$O. After 1 h of stirring this led to the formation of the title compound. MALDI-TOF m/z [M+H]$^+$ calcd. 1322.6, found 1322.4.

Phth(SO$_3$)-Cy5-(SO$_3$)EuK(OtBu)$_3$

Phth(SO$_3$)-Cy5-(SO$_3$)COOH (10.0 mg, 12.06 µmol) and EuK(OtBu)$_3$ (64 mg, 120.63) were dissolved in DMSO. PyBOP (63 mg, 120.63 µmol), DiPEA (53 µL, 301.57 µmol) and DMSO (300 µL) were added and the mixture was stirred for 1 h at r.t. After dilution by CH$_3$CN and H$_2$O (0.1% TFA v/v) the mixture was purified by HPLC whereafter the correct fractions were pooled and lyophilised. MALDI-TOF m/z [M+2H]$^+$ calcd. 1298.6, found 1300.3.

Amine(S0)-Cy5-(SO$_3$)EuK(OtBu)$_3$

Phth(SO$_3$)-Cy5-(SO$_3$)EuK(OtBu)$_3$ was dissolved in methylamine (33 wt % in EtOH; 20 mL) and stirred for 3.5 h. After this time, remaining methylamine and EtOH were removed in vacuo. A mixture of H$_2$O/MeCN was added before purifying the crude by means of HPLC. Relevant fractions were combined and concentrated in vacuo, yielding the title compound as a blue solid. MALDI-TOF m/z [M+2H]$^+$ calcd. 1170.5, found 1169.9.

MAS3(SO$_3$)-Cy5-(SO$_3$)EuK(OtBu)$_3$

Amine(SO$_3$)-Cy5-(SO$_3$)EuK(OtBu)$_3$ (4.0 mg, 3.42 µmol), MAS3-Ahx-COOH (21 mg, 41.07 µmol), PyBOP (21.3 mg, 41.07 µmol) and DIPEA 11.8 µL, 68.44 µmol) were dissolved in DMSO (1.5 mL) and stirred for 2.5 h. After dilution by CH$_3$CN and H$_2$O (0.1% TFA v/v) the mixture was purified by HPLC whereafter the correct fractions were pooled and lyophilised. MALDI-TOF m/z [M+H]$^+$ calcd. 1660.0, found 1660.6.

MAS3(SO$_3$)-Cy5-(SO$_3$)EuK$_3$

MAS3(SO$_3$)-Cy5-(SO$_3$)EuK(OtBu)$_3$ was stirred in TFA/H$_2$O 95:5 (2 mL) for 1 h. The solvent was evaporated and the crude purified by HPLC and lyophilised. MALDI-TOF m/z [M+2H]$^+$ calcd. 1492.7, found 1492.4.

Example 3: Photophysical Properties of Exemplary Compounds

The photophysical characteristics of a fluorophore are important for a fluorophore that is used in hybrid tracers, such as a compound of the invention. These photophysical properties are influences by the structure of the compound.

The brightness of a dye—one of the most important photophysical characteristics in a clinical setting—is the product of its molar extinction coefficient (e) and quantum yield (φF). We therefore set out to determine the e of each fluorophore by creating a linear concentration range (7.5-0.25 µM) in PBS and measuring the corresponding absorbance (Table 1). The addition of a sulfonate on the carboxylic-acid-containing indoline moiety diminishes the epsilon and the use of extra aryl moieties on the cyanine backbone greatly diminishes the dyes' solvability and thus their epsilon is greatly diminished as well. This is not surprising, as it has been previously determined that benzo[e]indole-containing dyes do not dissolve in H2O or PBS due to the relatively planar and hydrophobic core, resulting in dye-dye stacking (by forming J-aggregates) through van der Waal's forces.

The ϕF of a fluorophore is the relation between the number of photons emitted divided by the number of photons absorbed by a single molecule. It is therefore also called the emission efficiency. These data were measured in PBS, which portrays significantly lower values compared to ϕF in DMSO but is more representative for an in vivo setting. From this data (Table 2), it can be derived that adding the electron-withdrawing sulfonate group on one indole moiety can negatively influence the fluorophore's emission efficiency. Perhaps an asymmetrical cyanine core, with its significant electron density imbalance, is an inefficient fluorophore. In line with our expectations-since the benzo[e]indole caused J-aggregate formation, the ϕF of benzo[e]indole-containing fluorophores were diminished. Ordinarily enough, Phth(Ar)-Cy5-(Ar)COOH, containing two benzo[e]indole moieties, did not portray the lowest ϕF of the three benzo[e]indole-containing fluorophores. The only trend derived from the abovementioned data is that the free fluorophore benefits (when optimising emission efficiency) from symmetrical substituents on the cyanine structure. Hybrid tracers, however, do not portray this trend. As seen in Table 2, EuK(SO$_3$)-Cy5-MAS$_3$ possesses the highest ϕF of the matrix.

mining factor in a compound's absorption, distribution, metabolism and excretion (ADME properties). Hence, this criterion is widely used as an early indicator in pre-clinical evaluation. We calculated the log D values at pH 7.4 (c log D) as EuK-Cy5-MAS3 −7.15, EuK(SO3)-Cy5-MAS3 −10.31, EuK-Cy5-(SO3)MAS3 −10.31, EuK(Ar)-Cy5-MAS3 −6.16, EuK-Cy5-(Ar)MAS3 −6.16, EuK(Ar)-Cy5-(Ar)MAS3 −5.17.

Figure 2:
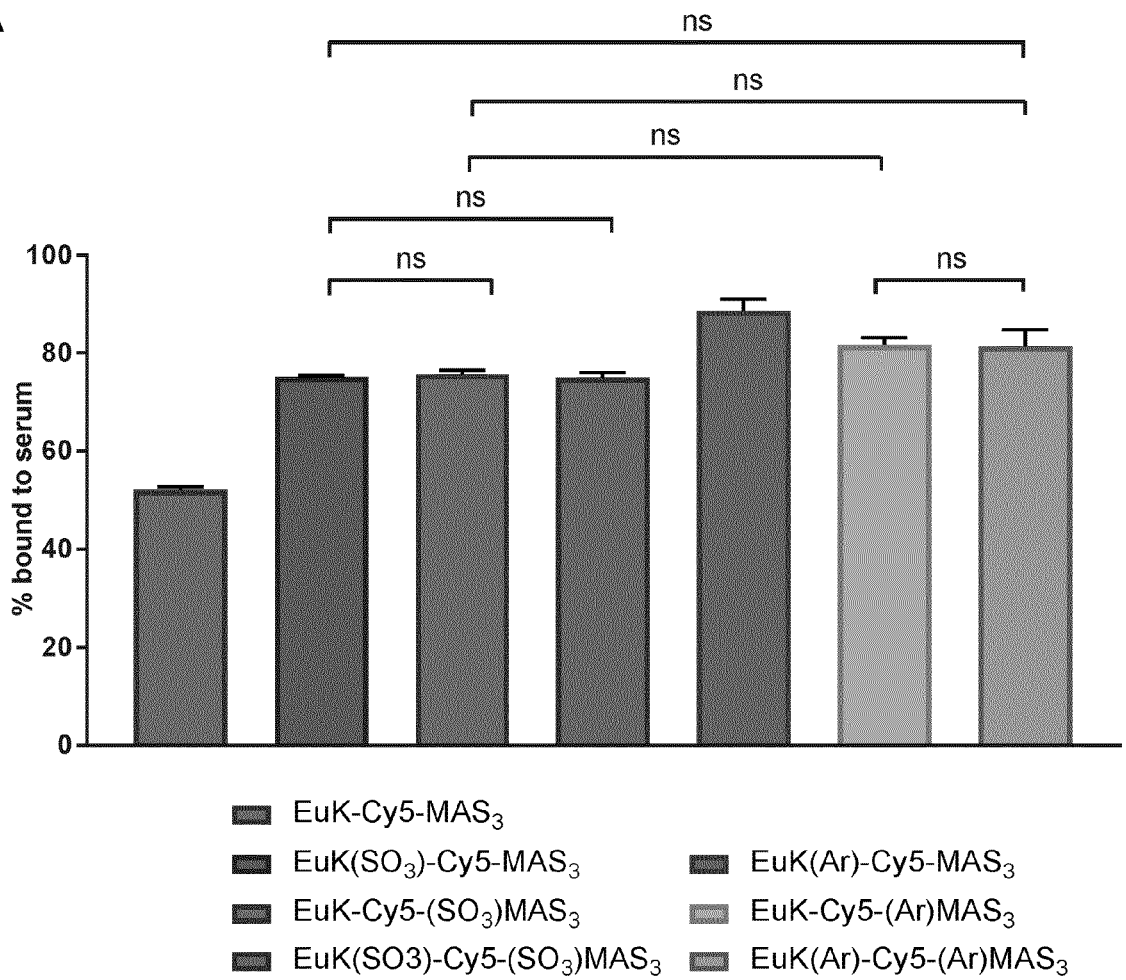
FIG. 2 illustrates the results for plasma protein interaction assays for exemplary hybrid tracer compounds. A) Plasma protein binding as a percentage of the indicated hybrid tracers bound to serum albumin. All hybrid tracers portray significant differences (p<0.05) except when noted (ns). B) and C) demonstrate the stability of hybrid tracers in serum albumin as a function of time based on B) absorbance and C) fluorescence.

Serum binding, or rather plasma protein binding (PPB) is a useful pharmacokinetic characteristic for the initial assessment of tracer candidates prior to in vivo use as PPB is directly related to, e.g., blood retention and clearance rates. All hybrid tracers have PPB with values between 52-89% with an average of 76±12% (FIG. 2A). The benzo[e]indole-containing hybrid tracers (EuK(Ar)-Cy5-MAS3, EuK-Cy5-(Ar)MAS3 and EuK(Ar)Cy5-(Ar)MAS3) tend to have the highest PPB. It is interesting to note that even though lipophilicity was decreased by adding a sulfonate group, the PPB of EuK(SO3)-Cy5-MAS3 and EuK-Cy5-(SO3)MAS3 are significantly higher than the PPB of EuK-Cy5-MAS3. This can be explained by Sudlow's site, a binding pocket in albumin's subdomain IIA, which binds bulky heterocyclic anions. No clear correlation could be found between c log D and serum binding. Even though PPB has a relation to the lipophilicity, it was expected that we could not predict the

TABLE 2

Selected photophysical properties of exemplary Cy5 dyes and hybrid tracer analogues

| Compound | ε (·10$^3$ M$^{-1}$ · cm$^{-1}$ in PBS) | $\lambda_{ex}/\lambda_{em}$ (Stokes shift in PBS; nm) | $\Phi_F$ (% in PBS) | Brightness (10$^3$ M$^{-1}$ · cm$^{-1}$ in PBS) |
|---|---|---|---|---|
| Phth-Cy5-COOH | 93 | 644/660 (16) | 12 | 11 |
| Phth(SO$_3$)-Cy5-COOH | 146 | 643/662 (19) | 7 | 6 |
| Phth-Cy5-(SO$_3$)COOH | 95 | 646/664 (18) | 9 | 12 |
| Phth(SO3)-Cy5-(SO3)COOH | 286 | 649/666 (17) | 14 | 39 |
| Phth(Ar)-Cy5-COOH | 60 | 662/680 (18) | 2 | 1 |
| Phth-Cy5-(Ar)COOH | 37 | 662/679 (17) | 10 | 6 |
| Phth(Ar)-Cy5-(Ar)COOH | 50 | 663/694 (31) | 7 | 4 |
| EuK-Cy5-MAS$_3$ |  | 644/663 (18) | 16 | $^1$5‡ |
| EuK(SO$_3$)-Cy5-MAS$_3$ |  | 648/664 (16) | 18 | 17‡ |
| EuK-Cy5-(SO$_3$)MAS$_3$ |  | 648/664 (16) | 7 | 10‡ |
| EuK(Ar)-Cy5-MAS$_3$ |  | 664/682 (18) | 9 | 3‡ |
| EuK-Cy5-(Ar)MAS$_3$ |  | 663/680 (17) | 9 | 5‡ |
| EuK(Ar)-Cy5-(Ar)MAS$_3$ |  | 682/700 (18) | 14 | 7‡ |

* $\lambda_{ex}/\lambda_{em}$ could not be measured due to severe stacking

‡Brightness is determined by using the ε of the hybrid's tracer corresponding fluorophore As the brightness of a fluorophore (or hybrid tracer) is one of its most important photophysical traits, we calculated the brightness for all fluorophores. In order to give insight in the hybrid tracer's optical performance, the brightness was determined by using the ε of its corresponding fluorophore in PBS. These approximations on tracer performance render it clear that, in line with the ϕF measurements, the highest observed brightness was depicted by tracers EuK(SO3)-Cy5-MAS3 and EuK-Cy5-MAS3, respectively. EuK(SO3)-Cy5-MAS3 thus contains the most favourable photophysical characteristics out of these 6 exemplary hybrid tracers.

Example 4: Lipophilicity and Serum Interaction of Exemplary Compounds

The lipophilicity of a compound can be expressed as the partition coefficient (log P) and affects both the pharmacodynamics and pharmacokinetics since it is a major deter- PPB based on the c log D as the PPB cannot be explained by a single physiochemical characteristic.

Not only serum binding, but also the stability in serum is valuable. This characteristic is another brick in the wall for the preclinical evaluation of hybrid tracers since this indicates a compound's in vivo stability. Clearly, any compound degrading in an in vivo environment is not suited for clinical use. All hybrid tracers were incubated in serum at 37° C. and their absorbance and fluorescence were measured after 24 h.

The time course data indicated (FIGS. 2B and 2C) a slight decrease in absorbance signal for most hybrid tracers (74.6±0.4-84.6±2.7% remaining absorbance after 24 h). Fluorescence signal was diminished to 67.1±7.3-88.7±5.6% after 24 h. The only significantly lower serum stability was observed for EuK(Ar)-Cy5-(Ar)MAS3 (p<0.05). All other exemplary tracers differed insignificantly.

Lipophilicity, plasma protein binding and serum stability results for five exemplary compounds are summarised in Table 3.

TABLE 3

Characteristics of exemplary hybrid tracers

| Compound | Lipophilicity (logP$_{(o/w)}$; n = 6)* | Plasma protein binding (n = 3) | Serum stability after 24 h (% remaining; absorbance/ fluorescence; n = 2) |
|---|---|---|---|
| EuK-Cy5-MAS$_3$ | −2.13 ± 0.10 | 88.3 ± 1.6 | 80 ± 6/86 ± 5 |
| EuK(SO$_3$)-Cy5-MAS$_3$ | −2.86 ± 0.05 | 85.0 ± 2.3 | 97 ± 2/89 ± 6 |
| EuK-Cy5-(SO$_3$)MAS$_3$ | −2.70 ± 0.01 | 87.4 ± 2.0 | 82 ± 7/85 ± 1 |
| EuK(Ar)-Cy5-MAS$_3$ | −1.75 ± 0.10 | 90.7 ± 1.3 | 85 ± 3/79 ± 1 |
| EuK-Cy5-(Ar)MAS$_3$ | −1.84 ± 0.06 | 89.0 ± 2.5 | 75 ± 0/76 ± 0 |

* *Measured using $^{99m}$Tc-labeled hybrid tracers

Figure 3:
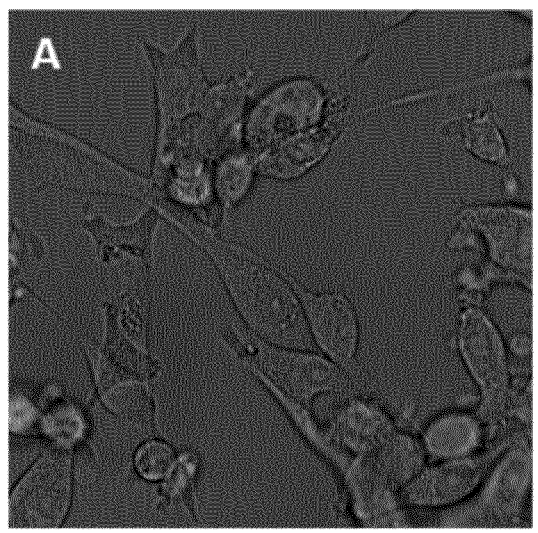
FIG. 3 illustrates PSMA-related staining of LNCaP cells after incubation with hybrid tracer EuK($SO_3$)-Cy5-$MAS_3$. A) provides a brightfield image of incubated cells. B) provides an overlay of confocal images of incubated cells with Cy5-related signal of the PSMA-targeting tracer in red, the nucleus in blue and lysosomes in the cytoplasm in green. C) provides an overlay of the confocal and brightfield images.
Figure 3:
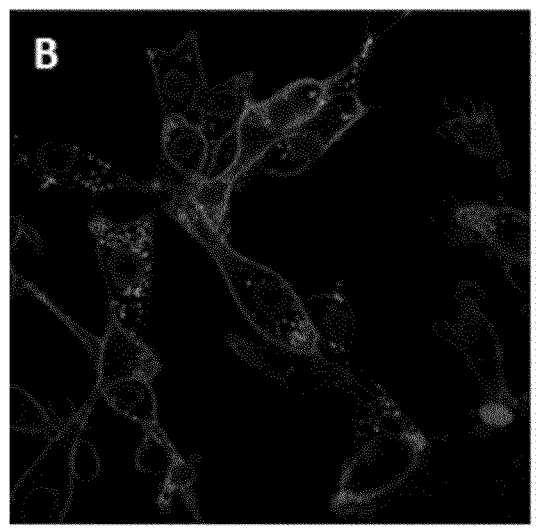
Figure 3:
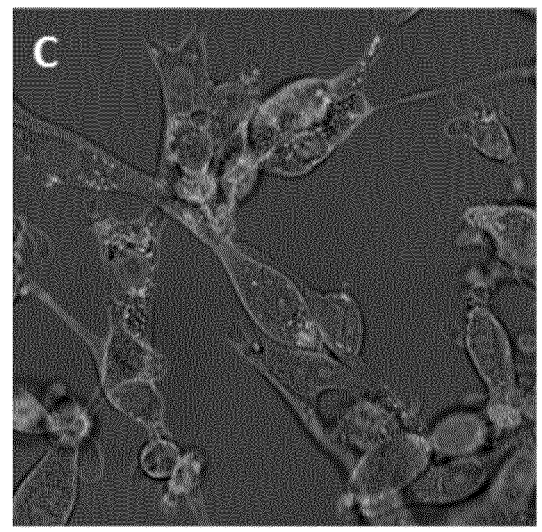

Example 5: Serum Confocal Microscopy and Receptor Affinity of Exemplary Compounds Fluorescence confocal microscopy was utilised as a tool for receptor localisation. As depicted in FIG. 3, a typical PSMA-targeting tracer brightly stains the extracellular receptor. IC50 was determined in a competitive binding assay using human LNCaP cells and EuK[$^{125}$I]I-BA as competitive radioligand. EuK(Ar)-Cy5-(Ar)MAS3 has the lowest affinity (345±31), while 4 out of 5 other tracers are in the same nanomolar range (113-175 nM). The only tracer with an improved IC$_{50}$ is EuK(SO3)-Cy5-MAS3 with an affinity of 19±6.

This demonstrates that the introduction of benzene (Ar) moieties did not increase the affinity while the introduction of an anionic sulfonate moiety (SO$_3$) on the C-terminus of the cyanine backbone increased the PSMA affinity compared to EuK-Cy5-MAS. Furthermore, the affinity of EuK—(SO3) Cy5-MAS3 was more than 9-fold higher than that of EuK-Cy5(SO3)-MAS3. Without wishing to be bound by any theory, this suggests that in interactions with the amphipathic entrance funnel of PSMA; the cyanine backbone of exemplary hybrid tracers allows hydrophobic interactions to be complemented with hydrogen bonding enabled by careful placement of an anionic moiety, such as the sulfonate moiety.

TABLE 4

Exemplary hybrid tracer PSMA affinity using human LNCaP cells and EuK[$^{125}$I]I-BA as a competitive radioligand; n ≥ 3

| Hybrid tracer | IC$_{50}$ (nM) |
|---|---|
| EuK-Cy5-MAS3 | 175.3 ± 61.6 |
| EuK(SO$_3$)-Cy5-MAS$_3$ | 19.2 ± 5.8 |
| EuK-Cy5-(SO$_3$)MAS$_3$ | 118.8 ± 117.4 |
| EuK(SO$_3$)-Cy5-(SO$_3$)MAS$_3$ | 18.3 ± 8.0 |
| EuK(Ar)-Cy5-MAS$_3$ | 113.1 ± 35.9 |
| EuK-Cy5-(Ar)MAS$_3$ | 164.4 ± 76.9 |
| EuK(Ar)-Cy5-(Ar)MAS$_3$ | 344.7 ± 30.9 |

Example 6: Exemplary Compounds In Vivo

The in vivo characteristics were investigated in male BALB/c nude mice using orthotopically transplanted PC346C cells. These mice were analysed in various ways, i.e., in vivo nuclear imaging (SPECT) in tumour-bearing mice, in vivo optical imaging (fluorescence imaging) in tumour-bearing mice, ex vivo biodistribution (percentage injected dose per gram (% ID/g)) in healthy and tumour-bearing mice and ex vivo fluorescence imaging.

Figure 4:
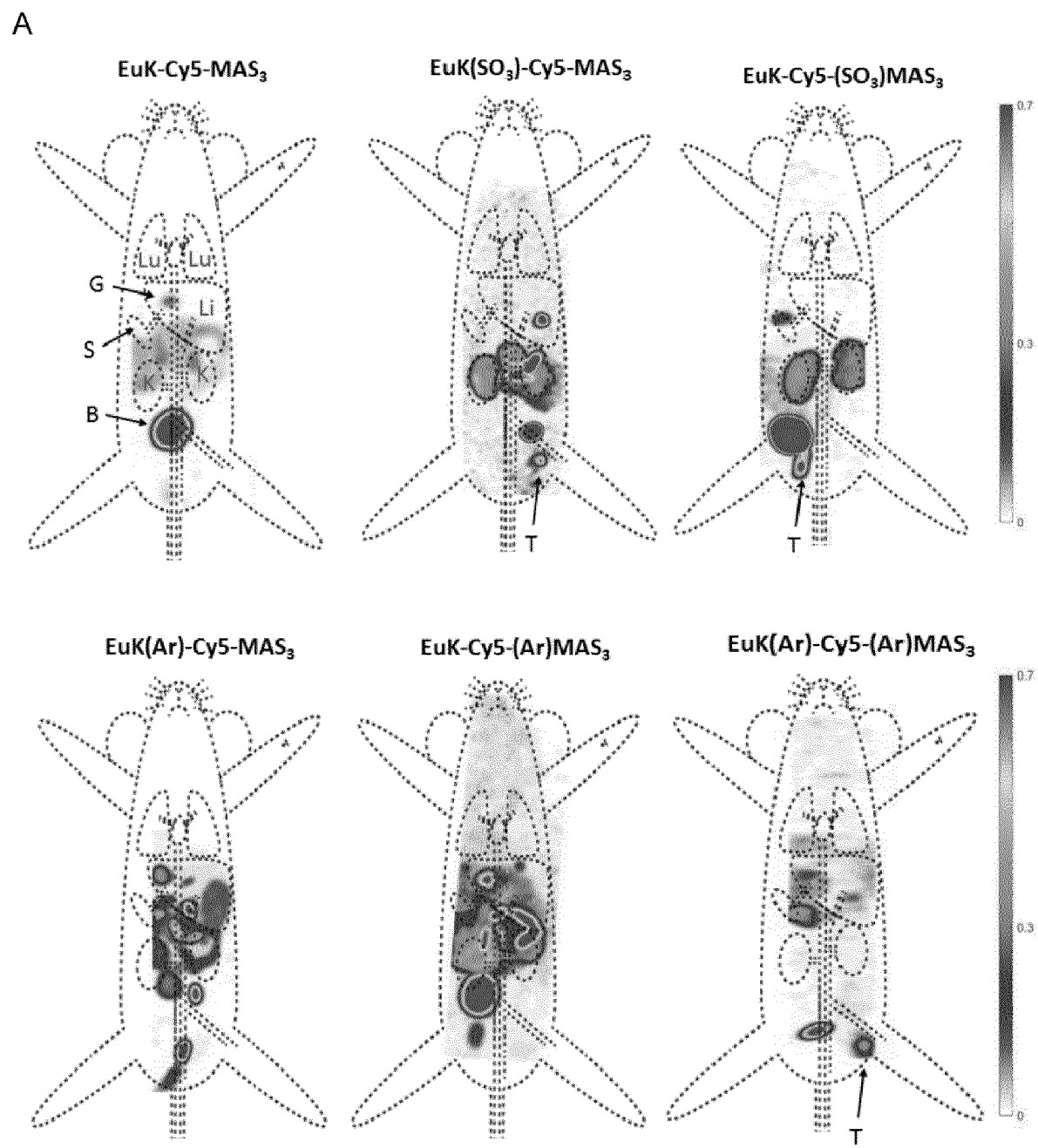
FIG. 4 provides a comparison of nuclear imaging and quantitative biodistribution of exemplary hybrid tracers, demonstrating tumour binding of exemplary hybrid tracers. A) In vivo SPECT imaging. Coronal SPECT imaging image of prostate tumour-bearing mice injected with either one of the PSMA hybrid tracer analogues. Organs are denoted as Lu (lungs), Li (liver), G (gallbladder), S (spleen), K (kidneys), B (bladder) and T (tumour). B) Comparison of biodistribution of the hybrid tracer matrix compared to the clinically approved tracer PSMA I&S, with C) providing the biodistribution of hybrid tracer EUK($SO_3$)—CY5-$MAS_3$. Biodistribution pattern at 2 h post injection of the different hybrid tracers from the matrix compared to the reference tracer PSMA I&S depicted as percentage of the injected dose per gram tissue (% ID/g).

SPECT imaging of the hybrid tracer matrix in tumour-bearing nude BALB/c mice resulted in clear nuclear imaging of the tumour with EuK(Ar)-Cy5-(Ar)MAS3, EuK(SO3)-Cy5-MAS3 and EuK-Cy5-(SO3)MAS3 (FIG. 4A). Upon analysing the ex vivo biodistribution it immediately becomes apparent that the tumour uptake of the hybrid tracers synthesised herein is similar or superior to the clinically approved PSMA I&S. Perhaps more importantly, a significant reduction in the renal and splenic accumulation was observed for all hybrid PSMA-analogues compared to both PSMA I&S and PSMA-11 analogues (kidney accumulation: range 10.8±9.79-21.8±14.2 ID/g compared to 186.0±23.0 for PSMA I&S and range 124.8±32.3-221.0±24.4 for PSMA-11 analogues). Prolonged renal tracer clearance may be a direct result of the renal tracer fraction, this significant reduction observed for the exemplary tracers of the invention indicates that these compounds have potential in surgical guidance applications. Furthermore, nonspecific accumulation appears to be quite low for all exemplary tracers of the invention, a further advantageous property.

Figure 5:
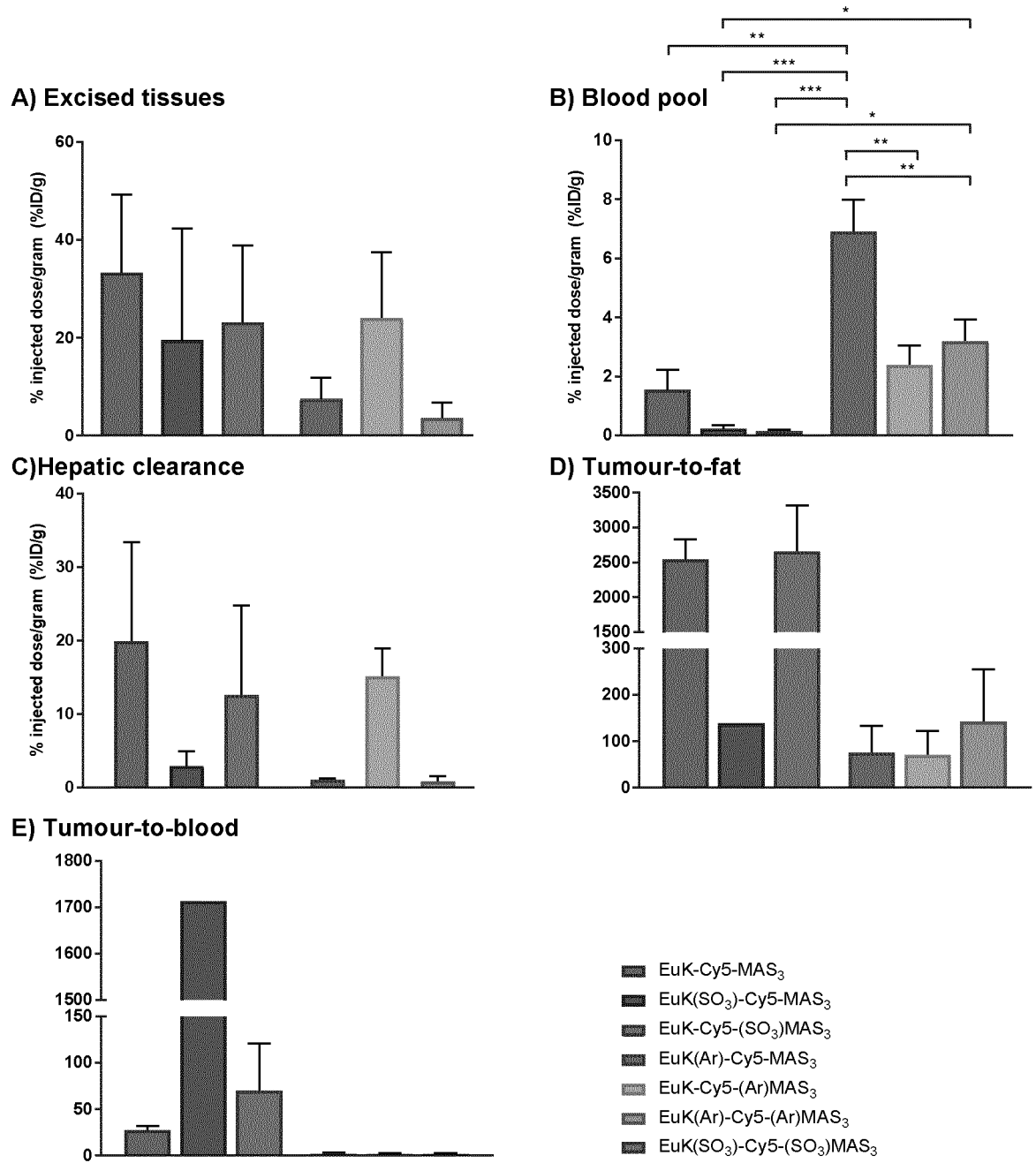
FIG. 5 illustrates biodistribution parameters and tumour uptake for exemplary hybrid tracers. Overview of A) the % Injected activity found in all excised organs percentage of the injected activity that remained at 2 h post tracer injection (all ns), B) the amount of radioactivity still present in the blood pool and C) no significant differences in hepatic clearance between the compounds. To highlight the visibility of the tumour over background tissue notorious for occluding signal within the area of the prostate, the D) tumour-to-fat and E) the tumour-to-blood ratio are provided for the individual hybrid tracers. Significance portrayed as: nothing (non-significant) *(p≤0.05) (p≤0.01) *(p≤0.001).

The tracer with the highest PPB has the highest blood retention (6.91±1.08 ID/g; EuK(Ar)-Cy5-MAS3), and the two tracers with c log D lower than −10 are almost entirely excreted from the blood (FIG. 5B). Interestingly, the hepatic clearance is lowest for the most lipophilic tracer (0.87±0.66; EuK(Ar)-Cy5-(Ar)MAS3) and one of the penultimate lipophilic tracers (0.94±0.13; EuK(Ar)-Cy5-MAS3) (FIG. 5C). Substituents on the EuK-bearing indole clearly reduces hepatic clearance significantly (19.93±13.44 EuK-Cy5-MAS3; 2.90±2.06 EuK(SO3-)-Cy5-MAS3; 1.10±0.14 EuK (Ar)-Cy5-MAS3; 0.87±0.66 EuK(Ar)-Cy5-(Ar)MAS3). When analysing the biodistribution data even further, it becomes clear that the correlation between PPB and clearance seems to be inversed as previously thought, since the % injected activity in all excised organs together diminishes as the PPB enlarges (FIG. 5A).

Figure 6:
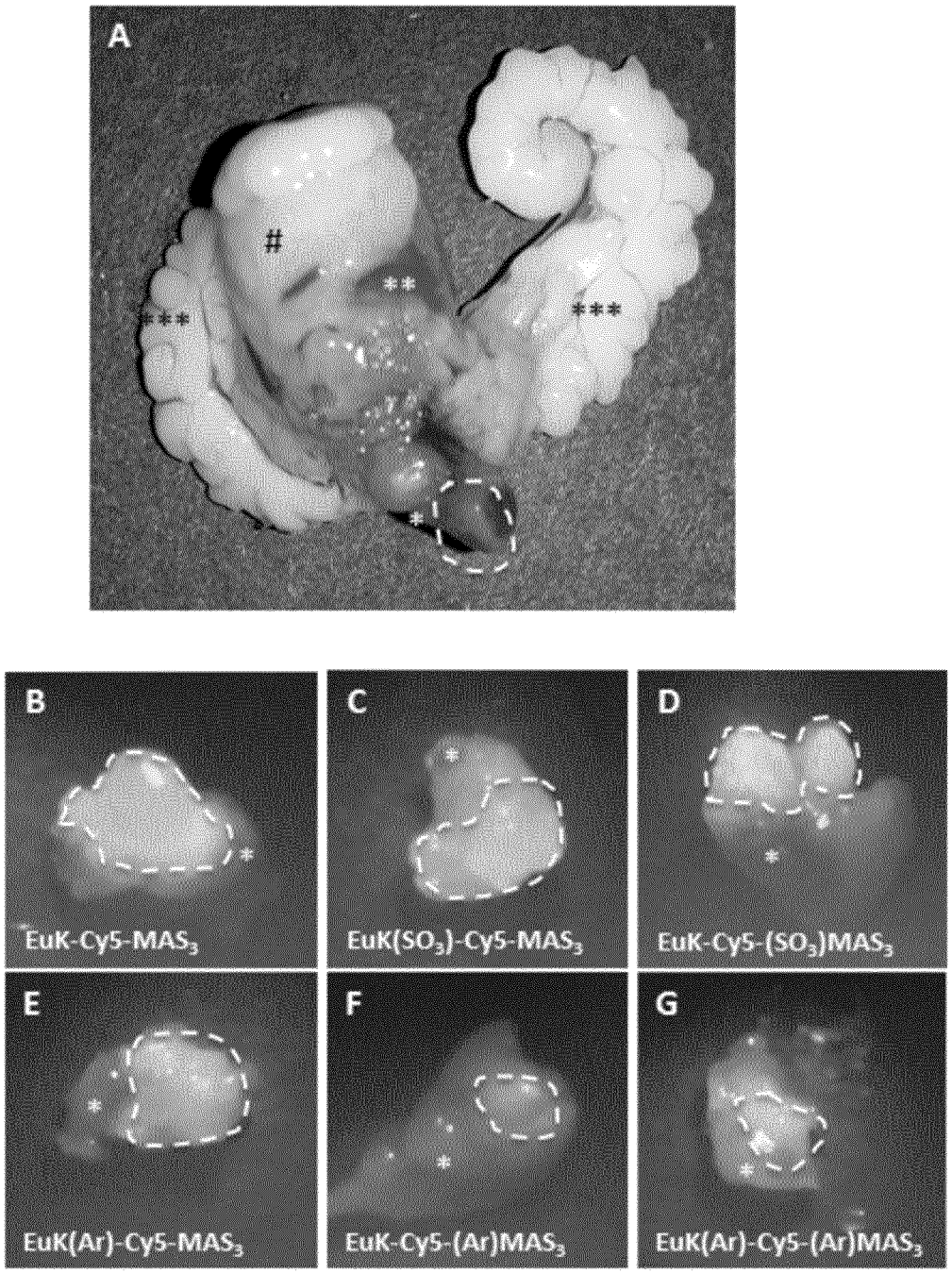
FIG. 6 demonstrates ex vivo fluorescence imaging of tumour containing prostate tissue of mice injected with one of the exemplary hybrid tracers. A) Photograph of the location of the tumour (within dotted line) in relation to healthy prostate tissue (*), the bladder (), the seminal vesicles (*) and fatty tissue within the abdomen (#). Fluorescence image of B) EuK-Cy5-$MAS_3$, C) EuK($SO_3$)-Cy5-$MAS_3$, D) EuK-Cy5-($SO_3$)$MAS_3$, E) EuK(Ar)-Cy5-$MAS_3$, F) EuK-Cy5-(Ar)$MAS_3$, G) EuK(Ar)-Cy5-(Ar)$MAS_3$ obtained with a clinical laproscope modified for Cy5 imaging.

As the prostate is surrounded by adipose tissue, an important consideration in designing hybrid tracers for prostate-specific surgery is the tumour-to-fat ratio (T/F). Furthermore, the tumour-to-blood ratio (T/B) gives a general interpretation of the signal-to-background ratio. It immediately becomes clear that increasing the lipophilicity does not assist with the T/F and T/B ratios for these exemplary hybrid tracers. Furthermore, the T/F ratio is best for EuK-Cy5-MAS3 (2542±287) and EuK-Cy5-(SO3)MAS3 (2658±659) (FIG. 5D), but they do not significantly differ from each other. The T/B ratio (FIG. 5E) is quite low for all compounds except EuK(SO3)-Cy5-MAS3 (1713). In addition, the ex vivo fluorescence imaging of tumour-containing prostate tissue shows a clear delineation of the prostate tissue for all hybrid tracers but EuK-Cy5-(Ar)MAS3 (FIG. 6).

The results indicate that the inclusion on the dye moiety of different functional groups and the positions of these functional groups have a direct influence on the tracer pharmacokinetics. Serum binding can be enhanced by introducing exemplary anionic (e.g. SO$_3^-$) or Ar groups. The different numbers and locations of SO$_3^-$ groups do not yield a different serum binding, but for Ar groups such effects are clearly observed. For example, a single Ar functionalization on the EuK side of the dye moiety yielded the highest serum binding, even compared to the tracer with an Ar unit on each side. A trend that seems to be in agreement with the blood pool values and increased blood, liver and salivary gland uptake observed in the biodistribution profile. While the high serum binding of the SO$_3^-$ does not appear to reflect the blood pool and in vivo intensities, which are in general much lower, the in vivo data does again illustrate that a single $SO_3^-$ functionalization on the EuK side of the dye yielded the highest tissue uptake. Hence having a non-symmetric dye moiety linker appears to be a key feature for in vivo tracer performance. Interestingly these trends are not that clearly observed in the renal retention and tumour uptake, which means that the tracer pharmacokinetics may be the most critical component during tracer selection. It follows that it is beneficial to provide a tracer that has a reduced background signal. In some examples, the lack of background signal seems to a decisive factor.

The invention claimed is:
1. A hybrid tracer of formula I or Ia:

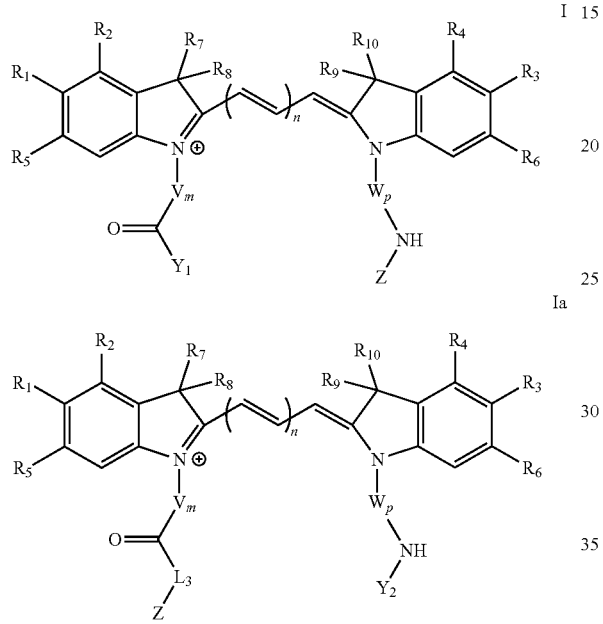

wherein:
$R_1$ is selected from sulfonate, carboxyl, phosphonate, and H and $R_2$ is H;
$R_3$ is selected from sulfonate, carboxyl, phosphonate, and H and $R_4$ is H;
wherein one of $R_1$ and $R_3$ is selected from sulfonate, carboxyl, phosphonate and the other of $R_1$ and $R_3$ is H;
each of $R_5$ and $R_6$ is H;
each of $R_7$, $R_8$, $R_9$ and $R_{10}$ is independently selected from sulfonate, carboxyl, phosphonate, $CH_3$, $CH_2CH_3$ and H;
each of
V is —$CH_2$— or —$CH_2CH_2O$—;
W is —$CH_2$— or —$CH_2CH_2O$—;
$Y_1$ is —EuK, —EuFA, —EuPG, or -$L_3$-EuE;
$Y_2$ is -$L_4$-EuK, -$L_4$-EuFA, -$L_4$-EuPG, or —EuE;
Z is a chelating moiety comprising a residue of bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino] pentyl]-N-hydroxybutandiamide (DFO), 4,11-bis (carboxymethyl)-1,4,8,11-tetraazabicyclo[6.6.2]-hexadecan (DO2A), N,N'-dipyridoxylethylendiamine-N,N'-diacetate-5,5'-bis(phosphat) (DPDP), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis (carboxymethyl)-1,4,8,11-tetraazabicyclo[6.6.2] hexadecane (TE2A), 1,4,8,11-tetraazacyclododecane-1,4,8, 11-tetraacetic acid (TETA), terpyridin-bis (methyleneamintetraacetic acid (TMT), 1,4,7,10-tetraazacyclo-tridecan-N,N',N",N"'-tetraacetic acid (TRITA), triethylenetetraaminehexaacetic acid (TTHA), N,N'-bis[(6-carboxy-2-pyridyl)methyl]-4,13-diaza-18-crown-6 ($H_2$macropa), or 4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide](THP); or Z is -$MAS_3$, -$MAG_3$, -DOTA-GA, -DOTA, or -DTPA, or a residue thereof;

$L_3$ is a linker of formula —NH—$R_{14}$—NH—, where $R_{14}$ is a substituted or unsubstituted alkyl, selected from a residue of lysine, a residue of ornithine or —NH—($C_4$-$C_7$alkyl)-NH—;
$L_4$ is a linker of formula —C(O)—$R_{15}$—C(O)—, where $R_{15}$ is a substituted or unsubstituted alkyl, selected from a residue of aspartic acid, a residue of glutamic acid or —C(O)—($C_4$-$C_7$alkyl)-C(O)—;
n is 2 or 3;
m is 4, 5, 6, 7 or 8; and
p is 3, 4, 5, 6, 7 or 8,
or a pharmaceutically acceptable salt thereof;
wherein —EuK is

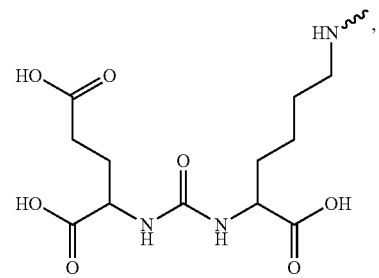

-EuFA is

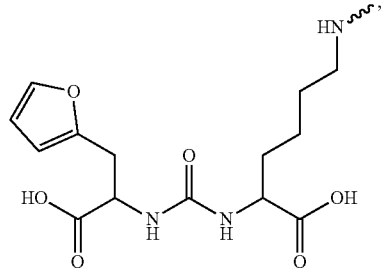

-EuPG is, and -EuE is

-DOTA is

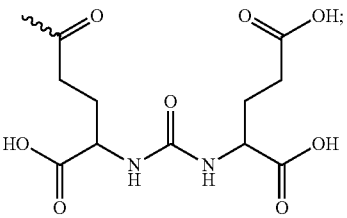

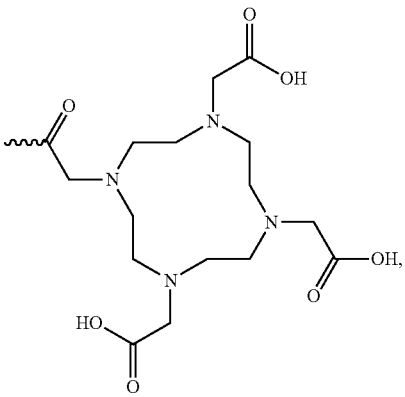

and
wherein -MAS$_3$ is and -DTPA is

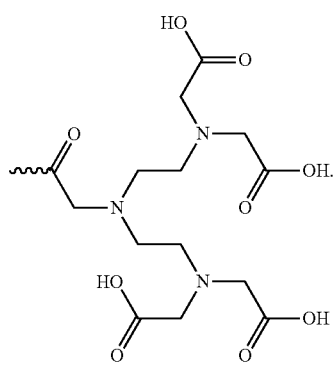

-MAG$_3$ is

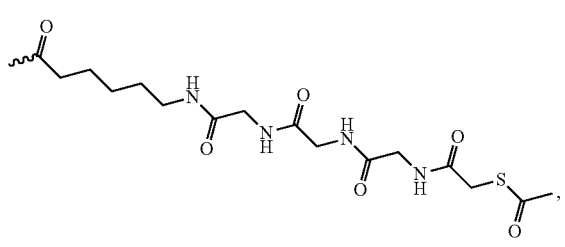

-DOTA-GA is

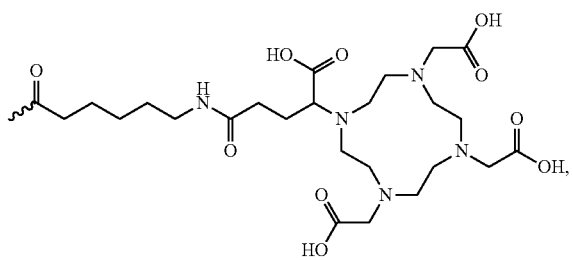

2. The hybrid tracer of claim 1, wherein at least one of the substituents R$_1$, R$_2$, R$_5$, R$_7$, R$_8$ of the first indole moiety differs from at least one of the substituents R$_3$, R$_4$, R$_6$, R$_9$, R$_{10}$ of the second indole moiety, thereby providing an asymmetric dye portion.

3. The hybrid tracer of claim 1:
wherein R$_1$ is selected from sulfonate and H; or
wherein R$_1$ is sulfonate; or
wherein R$_3$ is selected from sulfonate and H.

4. The hybrid tracer of claim 1, wherein each of R$_7$, R$_8$, R$_9$ and R$_{10}$ are —CH$_3$ or —H; optionally wherein each of R$_7$, R$_8$, R$_9$ and R$_{10}$ are —CH$_3$; and/or
wherein V is —CH$_2$— and/or W is —CH$_2$—; and/or
wherein m is 4, 5 or 6; further optionally wherein m is 5; and/or
wherein p is 3, 4, or 5; optionally wherein p is 4; and/or
wherein n is 2.

5. The hybrid tracer of claim 1, wherein Y$_1$ is —EuK; and/or
wherein Z is -MAS$_3$, -MAG$_3$, -DOTA-GA, -DOTA, or -DTPA; optionally Z is -MAS$_3$.

6. A hybrid tracer is selected from:
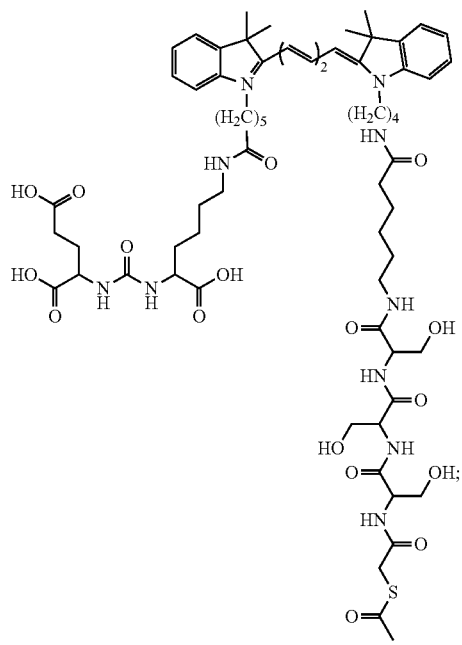
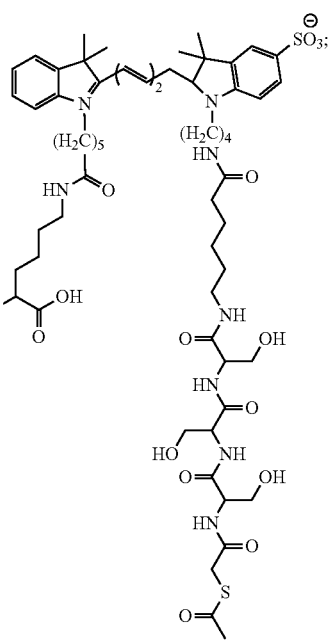
-continued
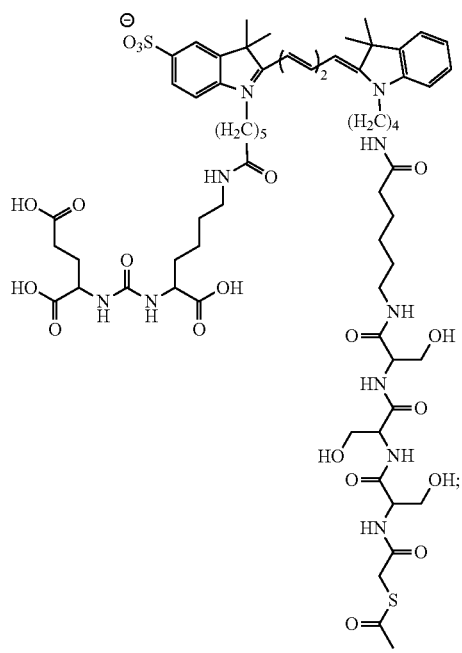

67
-continued
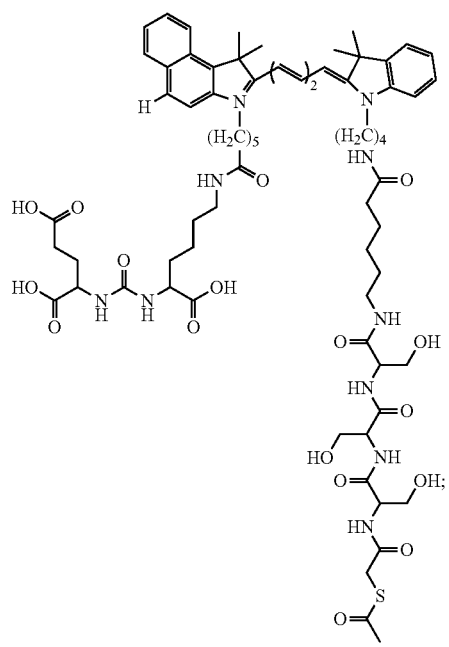
68
-continued
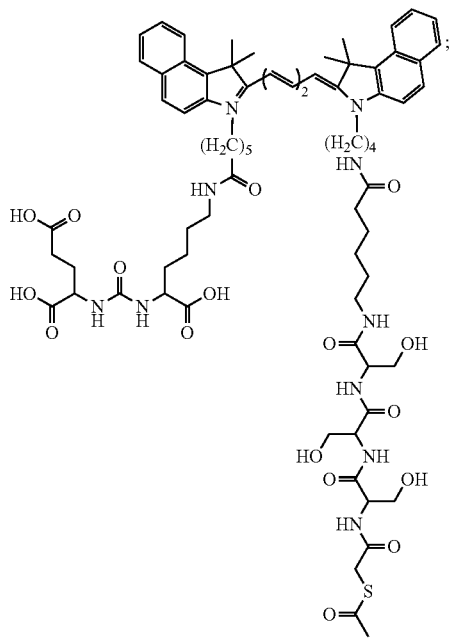

69
-continued
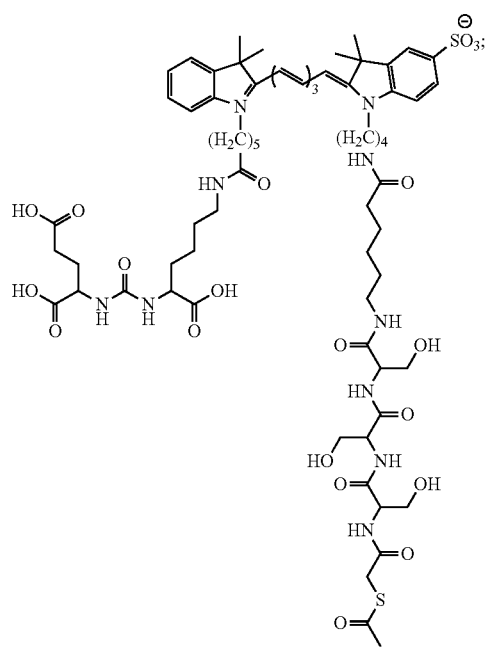
70
-continued
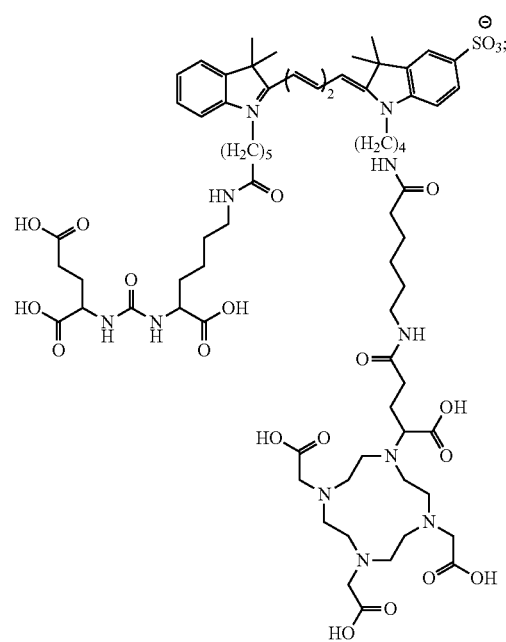
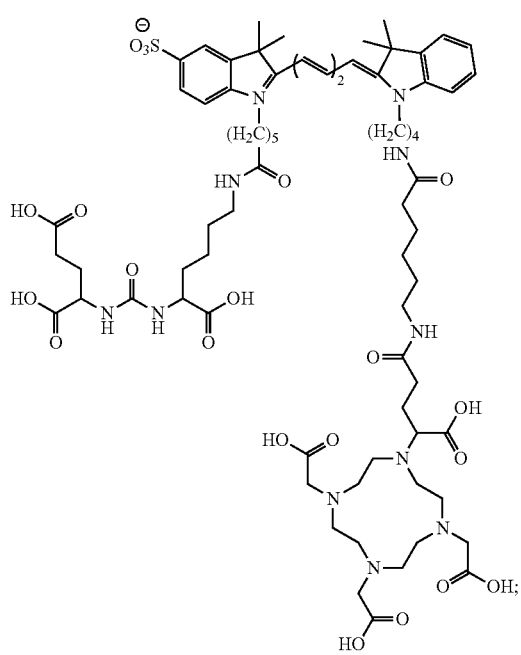
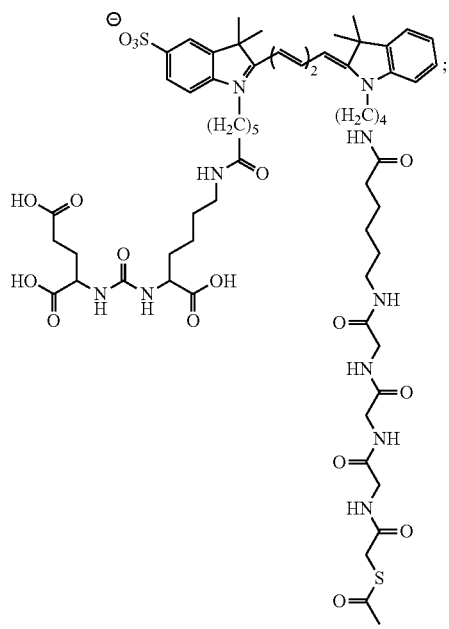

71
-continued
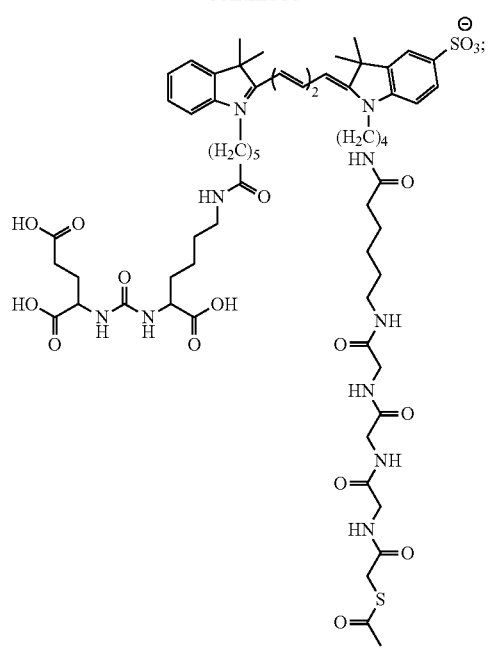
72
-continued
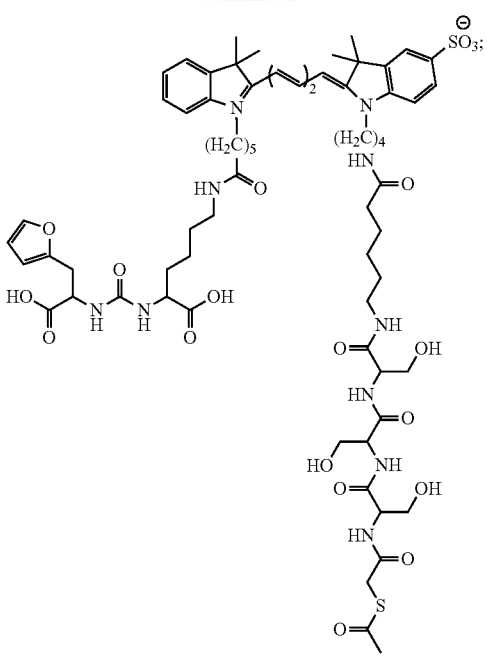
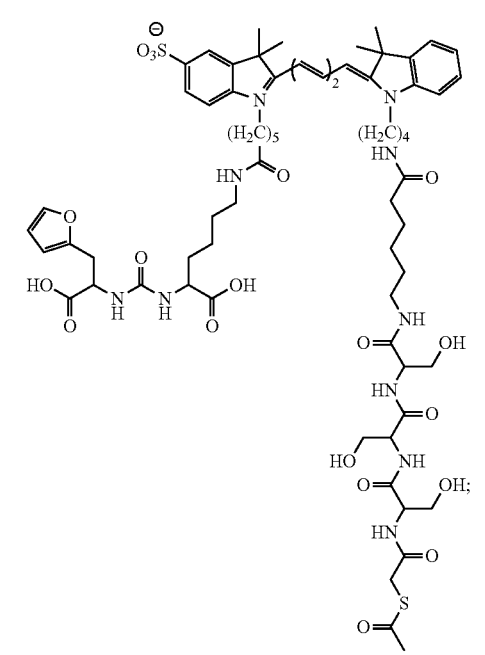
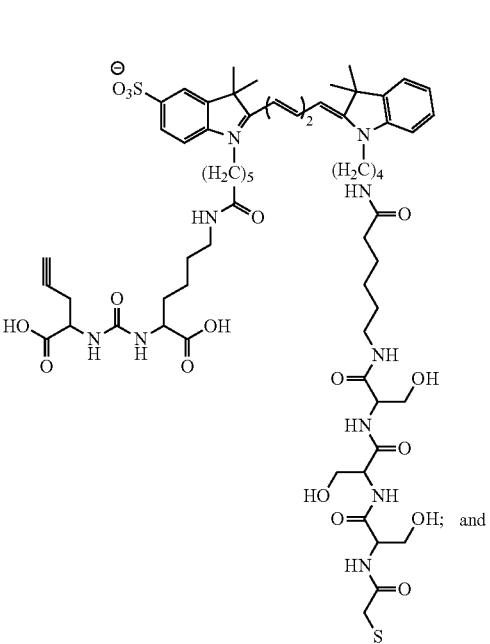
and

-continued

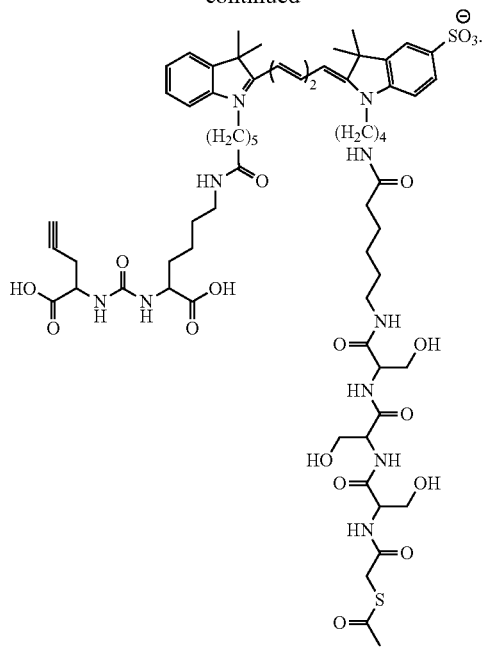

7. The hybrid tracer of claim 1, further comprising a chelated radiolabel, optionally selected from $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F.

8. A hybrid tracer of formula II or formula IIa, or a pharmaceutically acceptable salt thereof:

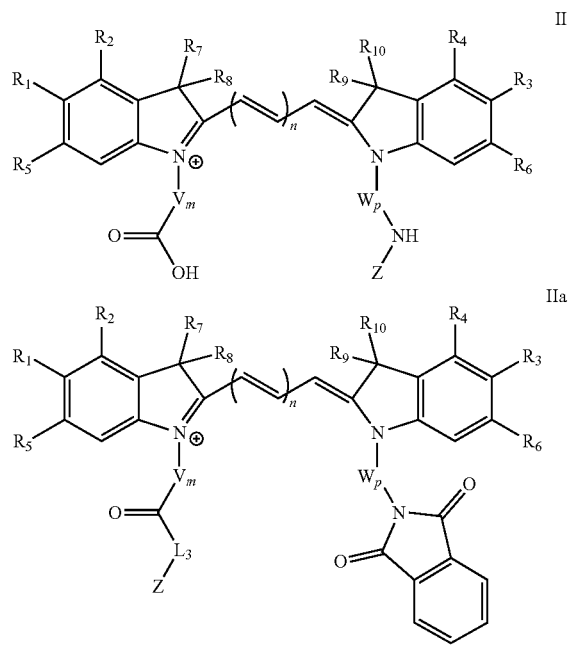

wherein:
$R_1$, $R_2$, $R_3$, $R_4$, $R_5$, $R_6$, $R_7$, $R_8$, $R_9$, $R_{10}$, V, W, Z, $L_3$, m, n and p are as defined in claim 1;
optionally wherein the hybrid tracer further comprises a chelated radiolabel selected from $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F.

9. A hybrid tracer of formula III or formula IIIa, or a pharmaceutically acceptable salt thereof:

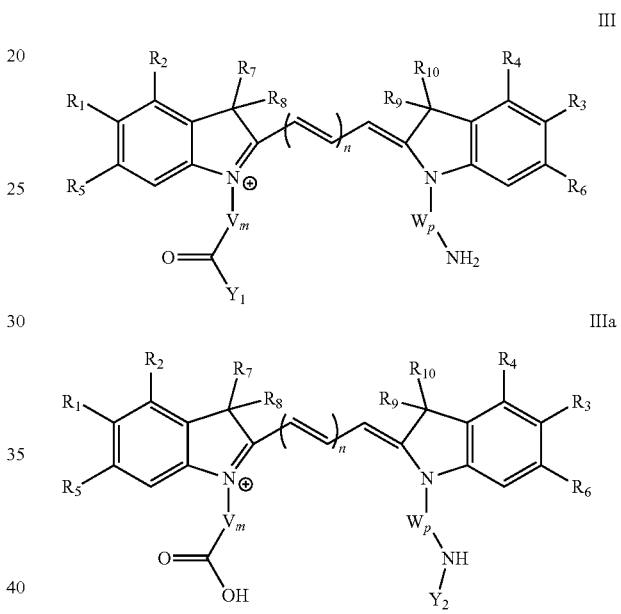

wherein:
$R_1$, $R_2$, $R_3$, $R_4$, $R_5$, $R_6$, $R_7$, $R_8$, $R_9$, $R_{10}$, V, W, $Y_1$, $Y_2$, m, n and p are as defined in claim 1.

10. A formulation, comprising the hybrid tracer of claim 1 and optionally a pharmaceutically acceptable carrier.

11. A method for imaging a tumour, comprising administering to a subject the hybrid tracer of claim 1, and after a predetermined time imaging the tumour.

12. The method of claim 11, wherein the tumour is a prostate cancer tumour, renal tumour, breast cancer tumour, glioma, colorectal adenocarcinoma, transitional cell carcinoma, pancreatic ductal adenocarcinoma, or gastric adenocarcinoma; optionally wherein the tumour is a prostate cancer tumour; and/or
  wherein the hybrid tracer comprises a chelated radiolabel and the imaging comprises positron emission spectroscopy (PET), single photon emission computed tomography (SPECT), scintigraphy, gamma-tracing/imaging, or beta-tracing; and/or
  wherein the imaging comprises fluorescence imaging, optionally wherein the imaging comprises fluorescence spectroscopy.

13. A method for the treatment of cancer, comprising administering to a patient an effective amount of the hybrid tracer of claim 1;

optionally wherein the cancer is prostate cancer, renal cancer, breast cancer, gliomas, colorectal adenocarcinoma, transitional cell carcinoma, pancreatic ductal adenocarcinoma, or gastric adenocarcinoma, optionally wherein the cancer is prostate cancer.

14. The method of claim 13, wherein the hybrid tracer comprises a chelated radiolabel.

15. A method for imaging a tumour, comprising administering to a subject the formulation of claim 10, and after a predetermined time imaging the tumour.

16. A method for the treatment of cancer, comprising administering to a patient an effective amount of the formulation of claim 10;

optionally wherein the cancer is prostate cancer, renal cancer, breast cancer, gliomas, colorectal adenocarcinoma, transitional cell carcinoma, pancreatic ductal adenocarcinoma, or gastric adenocarcinoma, optionally wherein the cancer is prostate cancer.

17. The method of claim 16, wherein the hybrid tracer comprises a chelated radiolabel.

* * * * *